US012697337B2

(12) United States Patent
Dai et al.

(10) Patent No.: US 12,697,337 B2
(45) Date of Patent: Aug. 4, 2026

(54) SOLID DISPERSIONS

(71) Applicant: InventisBio Co., Ltd., Shanghai (CN)

(72) Inventors: Xing Dai, Short Hills, NJ (US); Xiaomei Wang, Shanghai (CN); Yanqin Liu, Shanghai (CN); Yueheng Jiang, Shanghai (CN); Yaolin Wang, Shanghai (CN)

(73) Assignee: InventisBio Co., Ltd., Shanghai (CN)

( * ) Notice: Subject to any disclaimer, the term of this patent is extended or adjusted under 35 U.S.C. 154(b) by 390 days.

(21) Appl. No.: 18/281,051

(22) PCT Filed: Mar. 11, 2022

(86) PCT No.: PCT/CN2022/080270
§ 371 (c)(1),
(2) Date: Sep. 8, 2023

(87) PCT Pub. No.: WO2022/188849
PCT Pub. Date: Sep. 15, 2022

(65) Prior Publication Data

US 2024/0189313 A1 Jun. 13, 2024

(30) Foreign Application Priority Data

Mar. 11, 2021 (WO) ................ PCT/CN2021/080139

(51) Int. Cl.

| | |
|---|---|
| ***A61K 31/519*** | (2006.01) |
| ***A61K 9/00*** | (2006.01) |
| ***A61K 9/10*** | (2006.01) |
| ***A61K 9/16*** | (2006.01) |
| ***A61K 9/48*** | (2006.01) |
| ***A61K 45/06*** | (2006.01) |
| ***A61K 47/32*** | (2006.01) |
| ***A61K 47/34*** | (2017.01) |

(52) U.S. Cl.
CPC .......... *A61K 31/519* (2013.01); *A61K 9/0056* (2013.01); *A61K 9/10* (2013.01); *A61K 9/1682* (2013.01); *A61K 9/4866* (2013.01); *A61K 45/06* (2013.01); *A61K 47/32* (2013.01); *A61K 47/34* (2013.01)

(58) Field of Classification Search
CPC .................................................... A61K 31/519
See application file for complete search history.

(56) References Cited

U.S. PATENT DOCUMENTS

| | | | |
|---|---|---|---|
| 11,091,481 | B2 | 8/2021 | Dai |
| 11,241,437 | B2 | 2/2022 | Dai et al. |
| 11,865,115 | B2 | 1/2024 | Dai et al. |
| 12,110,289 | B2 | 10/2024 | Dai et al. |
| 12,246,020 | B2 | 3/2025 | Dai et al. |

FOREIGN PATENT DOCUMENTS

| | | |
|---|---|---|
| WO | 2018217651 | 11/2018 |
| WO | 2019051291 | 3/2019 |
| WO | 2019213516 | 11/2019 |
| WO | 2020233592 | 11/2020 |
| WO | 2021120045 | 6/2021 |

OTHER PUBLICATIONS

Mcmahon et al. (2000).*
Pinedo et al. (2000).*
Luo Y.J. et al., "Review and Prospect of Drug Solid Dispersion Preparation Technology", Chin.Pharm.J., vol. {0} 55, No. {0} 17, Sep. 30, 2020 (Sep. 30, 2020), pp. 1401-1408.
International Search Report for PCT/CN2022/080270 dated Jun. 6, 2022, 5 pages.
Written Opinion of the ISA for PCT/CN2022/080270 dated Jun. 6, 2022, 7 pages.

* cited by examiner

*Primary Examiner* — Paul V Ward
(74) *Attorney, Agent, or Firm* — NIXON & VANDERHYE, PC

(57) ABSTRACT

Provided herein are solid dispersions and pharmaceutical compositions of Compound 1. Also provided are methods of treating a disease or disorder such as a cancer or infectious disease that comprises administering to a subject in need thereof the solid dispersions or compositions described herein.

25 Claims, 19 Drawing Sheets

| Samples | SEM | |
|---|---|---|
| SDD-0A |  |  |
| SDD-13A |  |  |
| SDD-10A |  |  |

| Samples | SEM | |
|---|---|---|
| SDD-19A |  |  |

SOLID DISPERSIONS

CROSS-REFERENCE TO RELATED APPLICATIONS

This application is a U.S. National Phase of PCT Application No. PCT/CN2022/080270, filed Mar. 11, 2022, which claims the benefit of PCT Application No. PCT/CN2021/080139, filed Mar. 11, 2021, each of which is incorporated herein by reference in its entirety.

BACKGROUND

In various embodiments, the present disclosure generally relates to novel RAS inhibitors, compositions of the same, methods of preparing and methods of using the same, e.g., for inhibiting RAS and/or for treating a number of diseases or disorders, such as pancreatic, colorectal, and/or lung cancers.

Background

RAS proteins regulate key cellular pathway transmitting signal received from cellular membrane receptor to downstream molecules such as Raf, MEK, ERK and PI3K, which are crucial for cell proliferation and survival. RAS cycles between the inactive GDP-bound form and active GTP-bound form. RAS proteins have three gene isoforms: KRAS, NRAS and HRAS and share extensive homology (>90%) in the N-terminal domain (amino acid 1-165). RAS is frequently mutated cancers with KRAS accounted for ~80% of all RAS mutations. KRAS mutation occurs in approximately 60% of pancreatic cancer, 40% of colorectal cancer, 30% of lung cancer and 20% of endometrial carcinoma (F. McCormick, 2017, Clin Cancer Res 21: 1797-1801). The RAS hot-spot mutations occur at codons 12, 13 and 61, with 75% of KRAS mutations occurs at codon 12 (Glycine) (D. K. Simanshu, D. V. Nissley and F. McCormick, 2017, Cell, 170: 17-33).

There is a medical need for therapeutic treatments of cancer patients with RAS mutation such as KRAS G12C mutation.

BRIEF SUMMARY

The present disclosure generally relates to RAS inhibitors, such as KRAS inhibitors, in particular, Compound 1. Compound 1 as referred to in this disclosure has the following structure:

Compound 1

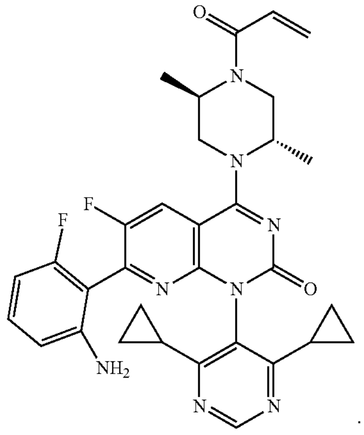 [SMILES: C=CC(=O)N1C[C@H](C)N(c2nc(=O)n(-c3c(C4CC4)ncnc3C3CC3)c3nc(-c4c(N)cccc4F)c(F)cc23)C[C@H]1C]

.

In various embodiments, the present disclosure is based in part, on the discovery that certain solid dispersions of Compound 1, in particular, amorphous solid dispersions of Compound 1, can be advantageously used for preparing pharmaceutical compositions, such as having better dissolution profile compared to crystalline forms of Compound 1.

Accordingly, various embodiments of the present disclosure are directed to various solid dispersions of Compound 1, preparation methods therefor, pharmaceutical compositions, and various uses thereof, such as for treating various diseases or disorders, such as cancer associated with KRAS G12C mutation, such as pancreatic, colorectal, and/or lung cancers.

In some embodiments, the present disclosure provides the following:

[1] A solid dispersion comprising Compound 1 in an amorphous form and a matrix polymer, wherein Compound 1 has the following formula:

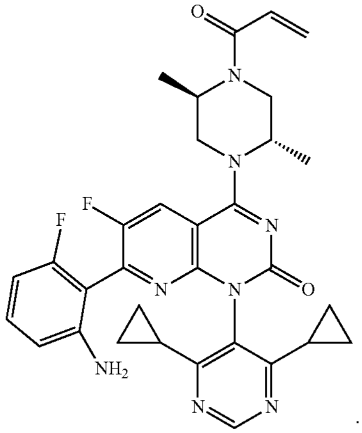

.

[2] The solid dispersion of [1], which is essentially free of Compound 1 in a crystalline form.

[3] The solid dispersion of [1], which does not include Compound 1 in a crystalline form in an amount detectable by XRPD.

[4] The solid dispersion of any one of [1]-[3], wherein the matrix polymer comprises one or more polymers selected from hydrophilic polymers, hydrophobic polymers, and amphiphilic polymers.

[5] The solid dispersion of any one of [1]-[3], wherein the matrix polymer comprises an acrylate based polymer, such as a polyacrylate or polymethacrylate, such as a cationic acrylate based copolymer.

[6] The solid dispersion of any one of [1]-[3], wherein the matrix polymer comprises a copolymer based on monomers comprising aminoalkyl acrylate and alkyl acrylate.

[7] The solid dispersion of any one of [1]-[3], wherein the matrix polymer comprises a copolymer based on monomers comprising aminoalkyl methacrylate and alkyl methacrylate.

[8] The solid dispersion of any one of [1]-[3], wherein the matrix polymer comprises a copolymer based on monomers comprising 2-dimethylaminoethyl methacrylate and an alkyl methacrylate.

[9] The solid dispersion of any one of [1]-[3], wherein the matrix polymer comprises a copolymer based on monomers comprising 2-dimethylaminoethyl methacrylate, butyl methacrylate, and methyl methacrylate.

[10] The solid dispersion of [9], wherein the copolymer is based on monomers comprising 2-dimethylaminoethyl methacrylate, butyl methacrylate, and methyl methacrylate with a ratio of about 2:1:1.

[11] The solid dispersion of any one of [6]-[10], wherein the copolymer is a random copolymer.

[12] The solid dispersion of any one of [1]-[3], wherein the matrix polymer is poly((2-dimethylaminoethyl)methacrylate, butyl methacrylate, methyl methacrylate) (2:1:1), e.g., Eudragit®E100.

[13] The solid dispersion of any one of [1]-[3], wherein the matrix polymer comprises an N-vinyl lactam polymer, such as one or more polymers selected from vinyl pyrrolidone polymers and vinyl caprolactam polymers.

[14] The solid dispersion of any one of [1]-[3], wherein the matrix polymer comprises one or more polymers selected from povidone, copovidone, and a graft copolymer of polyethylene glycol, polyvinyl acetate and polyvinylcaprolactam, such as Soluplus®.

[15] The solid dispersion of any one of [1]-[3], wherein the matrix polymer comprises a graft copolymer of polyethylene glycol 6000, polyvinyl acetate and polyvinylcaprolactam, with a weight average molecular weight ($M_w$) of about 90,000 g/mol to about 140,000 g/mol, such as about 118,000 g/mol.

[16] The solid dispersion of any one of [1]-[3], wherein the matrix polymer comprises a graft copolymer of polyethylene glycol 6000, polyvinyl acetate and polyvinylcaprolactam, with a weight ratio of about 13:30:57, wherein the graft copolymer has a weight average molecular weight ($M_w$) of about 118,000 g/mol.

[17] The solid dispersion of any one of [1]-[3], wherein the matrix polymer comprises one or more cellulose selected from hydroxypropylmethyl cellulose, hydroxypropylmethyl cellulose acetate succinate, hydroxypropyl methylcellulose phthalate (HPMCP), and hydroxypropyl cellulose.

[18] The solid dispersion of any one of [1]-[17], wherein the weight ratio of Compound 1 to the matrix polymer ranges from about 1:50 to 10:1, such as about 1:20, about 1:10, about 1:4, about 1:2, about 2:3, about 1:1, about 3:2, about 10:1, or any range between the recited values.

[19] The solid dispersion of any one of [1]-[18], wherein Compound 1 is present in the solid dispersion in an amount ranging from about 10-80% by weight, such as about 20%, about 30%, about 40%, about 50%, about 60%, about 70%, or any range between the recited values.

[20] A process for making a solid dispersion comprising:

(a) mixing Compound 1, a polymer, and a solvent to form a solution; and (b) spray-drying the solution of step (a), thereby obtaining the solid dispersion, wherein Compound 1 has the following formula:

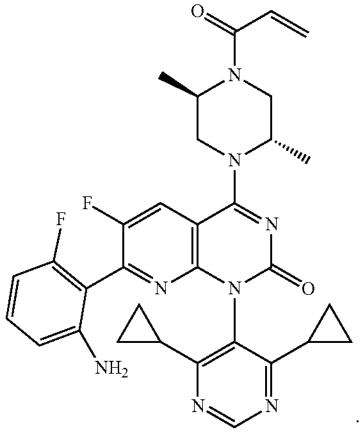 [SMILES: C=CC(=O)N1C[C@H](C)N(c2nc(=O)n(-c3c(C4CC4)ncnc3C3CC3)c3nc(-c4c(N)cccc4F)c(F)cc23)C[C@H]1C]

.

[21] The process of [20], wherein the solvent comprises acetone, dichloromethane, ethanol, methanol, water or a mixture thereof.

[22] The process of or [21], wherein the polymer is any of the polymers defined in [4]-[17].

[23] The process of any one of [20]-[22], wherein the weight ratio of Compound 1 to the polymer ranges from about 1:50 to 10:1, such as about 1:20, about 1:10, about 1:4, about 1:2, about 2:3, about 1:1, about 3:2, about 10:1, or any range between the recited values.

[24] The process of any one of [20]-[23], wherein the solid dispersion comprises Compound 1 in an amount ranging from about 10-80% by weight, such as about 20%, about 30%, about 40%, about 50%, about 60%, about 70%, or any range between the recited values.

[25] The solid dispersion prepared by the process according to any one of [20]-[24].

[26] The solid dispersion of [25], which is essentially free of Compound 1 in a crystalline form.

[27] The solid dispersion of [25], which does not include Compound 1 in a crystalline form in an amount detectable by XRPD.

[28] The solid dispersion of any one of [1]-[19] and [25]-[27], which is storage stable, for example, the solid dispersion is characterized in that, upon storage at 2-8° C., 25° C. and 60% relative humidity, or 40° C. and 75% relative humidity for one week or longer, such as up to 6 months or longer, the solid dispersion does not have Compound 1 in a crystalline form in an amount detectable by XRPD.

[29] A pharmaceutical composition comprising the solid dispersion of any one of [1]-[19] and [25]-[28].

[30] The pharmaceutical composition of [29], wherein the solid dispersion is present in an amount ranging from about 10-90% by weight, such as about 20%, about 30%, about 40%, about 50%, about 60%, about 70%, about 80%, or any range between the recited values.

[32] The pharmaceutical composition of or [30], wherein the solid dispersion is present in an amount ranging from about 50-70% by weight, such as about 50%, about 60%, about 70%, or any range between the recited values.

[32] The pharmaceutical composition of any one of [29]-[31], which is essentially free of Compound 1 in a crystalline form.

[33] The pharmaceutical composition of any one of [29]-[31], which does not include Compound 1 in a crystalline form in an amount detectable by XRPD.

[34] The pharmaceutical composition of any one of [29]-[31], further comprising one or more additional pharmaceutical excipients.

[35] The pharmaceutical composition of [34], wherein the one or more additional pharmaceutical excipients are selected from a diluent (e.g., microcrystalline cellulose, lactose, mannitol, etc.), a disintegrant (e.g., croscarmellose sodium, crospovidone, pregelatinized starch, etc.), a glidant (e.g., colloidal silica dioxide), a lubricant (e.g., sodium stearyl fumarate, magnesium stearate, hydrogenated castor oil, etc.), a surfactant (e.g., sodium lauryl sulfate, poloxamers, etc.), and a coating material.

[36] A method of preparing a pharmaceutical composition comprising mixing the solid dispersion according to any one of [1]-[19] and [25]-[28] with a pharmaceutical excipient.

[37] The method of [36], wherein the pharmaceutical excipient comprises one or more excipients selected from a diluent (e.g., microcrystalline cellulose, lactose, mannitol, etc.), a disintegrant (e.g., croscarmellose sodium, crospovidone, pregelatinized starch, etc.), a glidant (e.g., colloidal silica dioxide), a lubricant (e.g., sodium stearyl fumarate, magnesium stearate, hydrogenated castor oil, etc.), a surfactant (e.g., sodium lauryl sulfate, poloxamers, etc.), and a coating material.

[38] The method of [36] or [37], wherein the pharmaceutical composition comprises the solid dispersion in an amount ranging from about 10-90% by weight of, such as about 20%, about 30%, about 40%, about 50%, about 60%, about 70%, about 80%, or any range between the recited values.

[39] The method of [36] or [37], wherein the pharmaceutical composition comprises the solid dispersion in an amount ranging from about 50-70% by weight of, such as about 50%, about 60%, about 70%, or any range between the recited values.

[40] The pharmaceutical composition produced by the method according to any one of [36]-[39].

[41] The pharmaceutical composition of any one of [29]-[35] and [40], which is an oral dosage form, e.g., an oral solid dosage form.

[42] The pharmaceutical composition of any one of [29]-[35] and [40]-[41], which is in the form of a capsule, such as a hard gelatin capsule, a tablet, a strip, a caplet, a sachet, a lozenge, a suspension, or a powder for suspension.

[43] The pharmaceutical composition of any one of [29]-[35] and [40]-[42], which is storage stable.

[44] The pharmaceutical composition of any one of [29]-[35] and [40]-[43], characterized in that, upon storage at 2-8° C., 25° C. and 60% relative humidity, or 40° C. and 75% relative humidity for one week or longer, such as up to 6 months or longer, the pharmaceutical composition does not have Compound 1 in a crystalline form in an amount detectable by XRPD.

[45] A method of treating cancer in a subject, the method comprising administering to the subject a therapeutically effective amount of the solid dispersion of any one of [1]-[19] and [25]-[28] or the pharmaceutical composition of any one of [29]-[35] and [40]-[44].

[46] The method of [45], wherein the cancer is a hematologic malignancy, lung cancer (e.g., non-small cell lung cancer), pancreatic cancer, endometrial cancer, gall bladder cancer, thyroid cancer, bile duct cancer, and/or colorectal cancer.

[47] The method of [45] or [46], further comprising treating the subject with an additional therapy.

[48] The method of [47], wherein the additional therapy comprises administering to the subject a chemotherapeutic agent, therapeutic antibody, radiation, cell therapy, and/or immunotherapy.

[49] The method of any one of [45]-[48], wherein the subject has a G12C mutation of KRAS, HRAS and/or NRAS.

[50] A method of inhibiting KRAS G12C mutant protein in a cell of a subject, the method comprising administering to the subject an effective amount of the solid dispersion of any one of [1]-[19] and [25]-[28] or the pharmaceutical composition of any one of [29]-[35] and [40]-[44].

[51] A method of synthesizing Compound 1, comprising:

a) reacting compound 1-8 or a salt thereof with

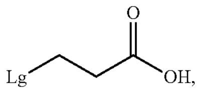

or an activated form thereof (e.g., acyl halide or anhydride) under an amide forming condition to form a compound of Formula I-Lg, wherein Lg is a leaving group (e.g., a halide or an oxygen-containing leaving group such as tosylate), 1-8

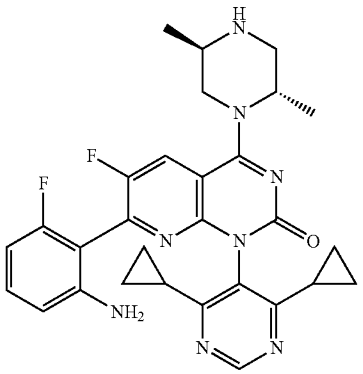

I-Lg

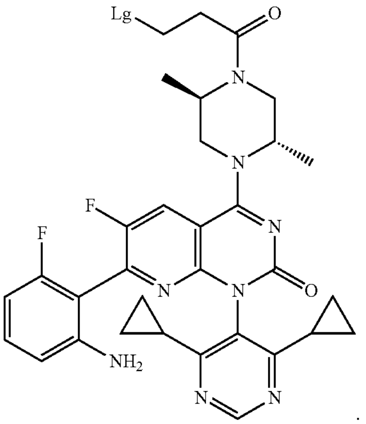

b) converting the compound of Formula I-Lg under an elimination condition to form Compound 1:

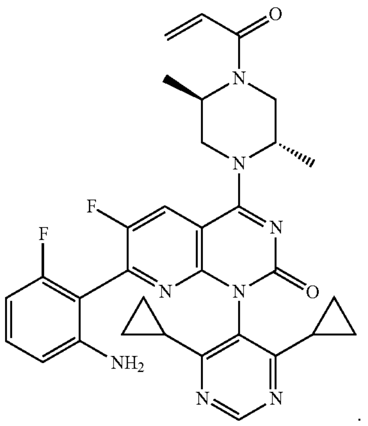 [SMILES: C=CC(=O)N1C[C@H](C)N(c2nc(=O)n(-c3c(C4CC4)ncnc3C3CC3)c3nc(-c4c(N)cccc4F)c(F)cc23)C[C@H]1C]

[52] The method of [51], wherein step a) comprises reacting compound 1-8 with

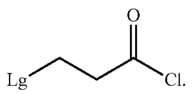

[53] The method of [51] or [52], wherein Lg is a halide, preferably, Cl.

[54] The method of any one of [51]-[53], wherein the converting step b) comprises treating the compound of Formula I-Lg with a base.

[55] The method of [54], wherein the base is an amine base, such as a tertiary amine base, e.g., DBU (1,8-Diazabicyclo[5.4.0]undec-7-ene).

[56] The method of any one of [51]-[55], wherein the compound 1-8 is prepared from deprotection of a compound of Formula I-P1:

I-P1

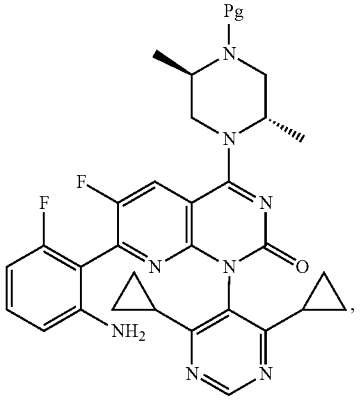

wherein Pg is a nitrogen protecting group, such as an acid deprotectable nitrogen protecting group, e.g., Boc (tert-butyloxycarbonyl).

[57] The method of [56], wherein the compound of Formula I-P1 is prepared from a process comprising coupling of a compound of Formula I-P2 with a compound of Formula I-P3:

I-P2

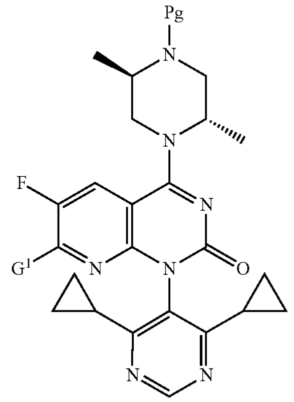

I-P3

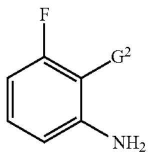

wherein Pg is defined above, $G^1$ is a leaving group, such as a halide or an oxygen-containing leaving group, and $G^2$ is a boronic acid, boronic ester, metal, or a residue such that the compound of Formula I-P3 is suitable for cross-coupling with the compound of Formula I-P2.

[58] The method of [57], wherein $G^1$ is Cl, and $G^2$ is $B(OH)_2$ or

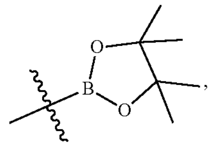 [SMILES: *B1OC(C)(C)C(C)(C)O1]

wherein the coupling of compounds of Formula I-P2 and I-P3 is mediated by a palladium catalyst.

[59] The method of or [58], wherein the compound of Formula I-P2 is prepared from reacting a compound of Formula I-P4 with a compound of Formula I-P5:

I-P4

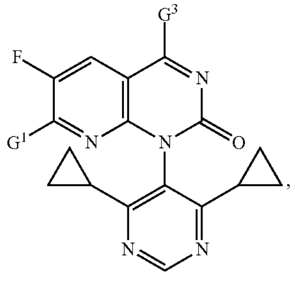

-continued

I-P5

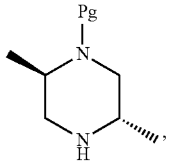

wherein $G^1$ and Pg are defined above, and $G^3$ is a leaving group, such as a halide.

[60] The method of [59], wherein $G^1$ and $G^3$ in Formula I-P4 are both Cl.

[61] The method of or [60], wherein the reacting of the compounds of Formula I-P4 and Formula I-P5 is conducted in the presence of a base, such as a tertiary amine base, e.g., DIPEA (diisopropyl ethyl amine).

[62] The method of [51], substantially the same as those described in Example 2 herein.

[63] A compound of Formula I-P1, I-P2, I-P4, or I-Lg, as defined herein, or a salt thereof.

[65] A compound selected from Compounds 1-6, 1-7, 1-8, and 1-9, or a salt thereof.

It is to be understood that both the foregoing summary and the following detailed description are exemplary and explanatory only, and are not restrictive of the invention herein.

BRIEF DESCRIPTION OF THE DRAWINGS/FIGURES

FIG. 1A shows a representative X-ray powder diffraction (XRPD) spectrum of crystalline form A of Compound 1. FIG. 1B shows a representative thermogravimetric analysis (TGA) and differential scanning calorimetry (DSC) analysis of crystalline form A of Compound 1.

FIG. 2A shows a representative X-ray powder diffraction (XRPD) spectrum of crystalline form B of Compound 1. FIG. 2B shows a representative thermogravimetric analysis (TGA) and differential scanning calorimetry (DSC) analysis of crystalline form B of Compound 1. FIG. 2C presents a representative Dynamic moisture sorption analysis (DVS) of form B of Compound 1. FIG. 2D presents XRPD spectra showing that Form B remain unchanged after DVS study.

DETAILED DESCRIPTION

Figure 1A:
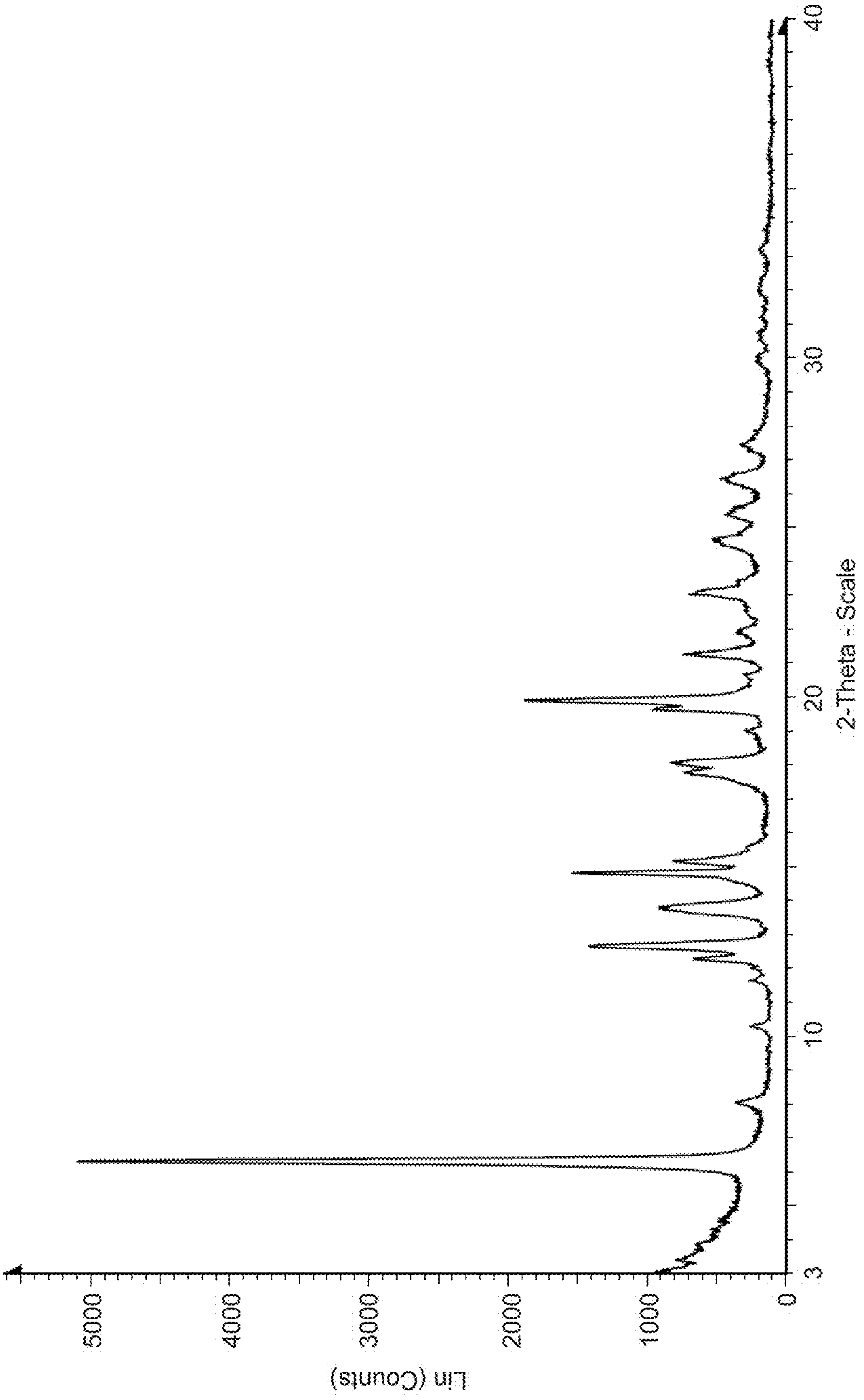

The present disclosure generally relates to RAS inhibitors, such as KRAS inhibitors, in particular, Compound 1. Compound 1 as referred to in this disclosure has the following structure:

Compound 1

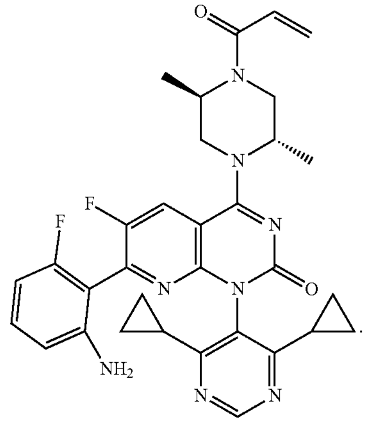

Compound 1 has a measured pKa of around 1 and typically exists in a free base form. Unless otherwise explicitly stated to the contrary, Compound 1 herein should be understood as existing in its free base form as opposed to a salt formed with an acid or base. The synthesis and utility of Compound 1 has been described in Applicant's previous applications, such as International Application Nos. PCT/CN2020/091274, filed May 20, 2020, published as WO2020/233592, PCT/CN2020/137276, filed Dec. 17, 2020, and PCT/CN2019/126230, filed Dec. 18, 2019, the contents of each of which are herein incorporated by reference in their entireties. As described therein, Compound 1 was shown to be a potent KRAS G12C inhibitor and was also found to be effective in treating various cancers in in vivo mouse models. PCT/CN2020/137276 and PCT/CN2019/126230 also describe various isolated forms, substantially pure forms, and/or solid forms of Compound 1 and their preparation methods. In particular, PCT/CN2020/137276 and PCT/CN2019/126230 identified several crystalline forms of Compound 1, Form A, B, C, and D, among which, Form B was identified as a more stable crystalline form.

As discussed in more detail below, in various embodiments, the present disclosure provides solid dispersions of Compound 1, preparation methods therefor, pharmaceutical compositions comprising the solid dispersions of Compound 1, and uses thereof, such as for treating various diseases or disorders, such as cancer associated with KRAS G12C mutation.

The solid dispersions herein, in particular amorphous solid dispersions of Compound 1, can be advantageously used for preparing pharmaceutical compositions, which can for example have a better dissolution profile compared to a crystalline form of Compound 1. As detailed herein, various amorphous solid dispersions of Compound 1 were found to have a much improved dissolution profile compared to crystalline Form B of Compound 1, when tested in a Fasted State Simulated Intestinal Fluid ("FaSSIF"). Additionally, various amorphous solid dispersions of Compound 1 and pharmaceutical compositions comprising such amorphous solid dispersions were found to be storage stable, for example, with no identifiable transition to crystalline forms under typical storage conditions.

Solid Dispersion of Compound 1

Some embodiments of the present disclosure are directed to a solid dispersion of Compound 1. Typically, the solid dispersion comprises Compound 1 and a pharmaceutically acceptable carrier, such as a pharmaceutically acceptable polymer.

The solid dispersion herein typically comprises Compound 1 in an amorphous form. For example, in some embodiments, Compound 1 in the solid dispersion can be in an amorphous form substantially free of any crystalline form. In some embodiments, the solid dispersion can be essentially free (e.g., less than 10%, less than 5%, less than 2%, etc.) of Compound 1 in a crystalline form. In some embodiments, the solid dispersion does not include Compound 1 in a crystalline form in an amount detectable by XRPD. The solid dispersion herein is preferably an amorphous solid dispersion, such as a stable amorphous solid dispersion.

Typically, the solid dispersion herein (e.g., an amorphous solid dispersion) comprises Compound 1 in an amorphous form and a matrix polymer.

Useful polymers suitable for use as matrix polymers for the solid dispersions herein are not particularly limited, so long as they are pharmaceutically acceptable. Preferably, the matrix polymer is a pharmaceutically acceptable polymer that once coprocessed with Compound 1, functions to maintain Compound 1 in amorphous form. While specific polymers are discussed herein as being suitable for use in the dispersions formable by the present disclosure, blends of such polymers may also be suitable. Thus, the term "matrix polymer" is intended to include blends of polymers in addition to a single species of polymer.

In some embodiments, the matrix polymer can be a hydrophilic polymer, a hydrophobic polymer, an amphiphilic polymer, or any combinations thereof. In some embodiments, the matrix polymer can be selected from cellulose esters and cellulose ethers, polyalkylene oxides, polyacrylates and polymethacrylates, homopolymers and copolymers of N-vinyl lactams, polyacrylamides, vinyl acetate polymers, graft copolymers of polyethylene glycol, polyvinyl caprolactam and polyvinyl acetate, polyvinyl acetate phthalate, oligo- and polysaccharides, and mixtures of two or more thereof.

In some particular embodiments, the matrix polymer can comprise an acrylate based polymer, such as a polyacrylate or polymethacrylate. As used herein, an "acrylate based polymer" should be understood as encompassing homopolymers and copolymers of acrylates, including polyacrylate or polymethacrylate. In some embodiments, the matrix polymer can comprise a cationic acrylate based copolymer, such as amino methacrylate copolymer, basic butylated methacrylate copolymer. In some embodiments, the matrix polymer can comprise a copolymer based on monomers comprising aminoalkyl acrylate and alkyl acrylate. In some embodiments, the matrix polymer can comprise a copolymer based on monomers comprising aminoalkyl methacrylate and alkyl methacrylate. In some embodiments, the matrix polymer can comprise a copolymer based on monomers comprising 2-dimethylaminoethyl methacrylate and an alkyl methacrylate. In some embodiments, the matrix polymer can comprise a copolymer based on monomers comprising 2-dimethylaminoethyl methacrylate, butyl methacrylate, and methyl methacrylate. In some embodiments, the matrix polymer can comprise a copolymer based on monomers comprising 2-dimethylaminoethyl methacrylate, butyl methacrylate, and methyl methacrylate with a ratio of about 2:1:1. The acrylate based copolymers are typically random copolymers. In any of the embodiments described herein, unless otherwise specified or contrary from context, the matrix polymer can be a copolymer of 2-dimethylaminoethyl methacrylate, butyl methacrylate, and methyl methacrylate, such as poly((2-dimethylaminoethyl)methacrylate, butyl methacrylate, methyl methacrylate) (2:1:1) (e.g. Eudragit®E100), which is commercially available, e.g., from Evonik. Unless otherwise specified, when applicable, the polymers referred to herein by generic or product names should be understood as encompassing the respective polymers that conform to the respective specification or acceptance criteria of one or more of the current pharmacopeias of U.S., Japan, China, and Europe, e.g., the specification as set forth in the latest editions of USP-NF monograph, Pharmacopoeia Europaea, Japanese Pharmacopoeia, or Chinese Pharmacopoeia as of the filing date of this application. For commercially available polymers referred to herein, it should be understood that such polymers include those conforming to the applicable specifications from the commercial sources as of the filing date of this application. For example, Eudragit®E100 should be understood as including any of the copolymers of poly((2-dimethylaminoethyl)methacrylate, butyl methacrylate, methyl methacrylate) (2:1:1) that conforms to the applicable specifications from the commercial sources (e.g., Evonik) as of the filing date of this application.

In some particular embodiments, the matrix polymer can comprise an N-vinyl lactam polymer, such as one or more polymers selected from vinyl pyrrolidone polymers and vinyl caprolactam polymers. For example, in some embodiments, the matrix polymer can comprise one or more polymers selected from povidone, copovidone, and a graft copolymer of polyethylene glycol, polyvinyl acetate and polyvinylcaprolactam, such as Soluplus®. In some embodiments, the matrix polymer can comprise povidone, such as PVP K30 or Kollidon® 30. In some embodiments, the matrix polymer can comprise copovidone, such as PVP-VA 64 or Kollidon VA64.

In some particular embodiments, the matrix polymer can comprise a graft copolymer of polyethylene glycol 6000, polyvinyl acetate and polyvinylcaprolactam, with a weight average molecular weight ($M_w$) of about 90,000 g/mol to about 140,000 g/mol, such as about 118,000 g/mol. In some embodiments, the matrix polymer comprises a graft copolymer of polyethylene glycol 6000, polyvinyl acetate and polyvinylcaprolactam, with a weight ratio of about 13:30:57, wherein the graft copolymer has a weight average molecular weight ($M_w$) of about 118,000 g/mol. In some embodiments, the matrix polymer can be a graft copolymer of polyethylene glycol, polyvinyl acetate and polyvinylcaprolactam, e.g., Soluplus®.

In some embodiments, the matrix polymer can comprise a cellulose, such as cellulose esters or ethers. For example, in some embodiments, the matrix polymer comprises one or more cellulose selected from hydroxypropylmethyl cellulose, hydroxypropylmethyl cellulose acetate succinate, hydroxypropyl methylcellulose phthalate (HPMCP) and hydroxypropyl cellulose (HPC). In some embodiments, the matrix polymer can comprise hydroxypropylmethyl cellulose (HPMC), e.g., HPMC E3 LV. In some embodiments, the matrix polymer can comprise hydroxypropylmethyl cellulose acetate succinate (HPMC-AS), such as the M, H, or L grade of HPMC-AS. In some embodiments, the matrix polymer can comprise hydroxypropyl cellulose, e.g., HPC-SSL. In some embodiments, the matrix polymer can comprise hydroxypropylmethyl cellulose phthalate (HPMCP), such as HP-55 or HP-50 grade.

In some specific embodiments, the solid dispersion herein can comprise Compound 1 in an amorphous form, which is dispersed (e.g., homogeneously dispersed) in a polymer selected from Kollidon VA64, Kollidon® 30, HPMCAS-MG, HPMCAS-HG, Poloxamer 188, Soluplus, HPMC E3 LV, Eudragit®E100, and Hydroxypropyl cellulose HPC-SSL. In some embodiments, Compound 1 in the solid dispersion can be in an amorphous form substantially free of any crystalline form. In some embodiments, the solid dispersion can be essentially free (e.g., less than 10%, less than 5%, less than 2%, etc.) of Compound 1 in a crystalline form. In some embodiments, the solid dispersion does not include Compound 1 in a crystalline form in an amount detectable by XRPD. In some embodiments, the solid dispersion is an amorphous solid dispersion. In some embodiments, the solid dispersion is a stable amorphous solid dispersion.

Typically, the weight ratio of Compound 1 to the matrix polymer in the solid dispersion ranges from about 1:50 to 10:1, such as about 1:20, about 1:10, about 1:4, about 1:2, about 2:3, about 1:1, about 3:2, about 10:1, or any range between the recited values. In some embodiments, the solid dispersion can comprise Compound 1 in an amount ranging from about 10-80% by weight, such as about 20%, about 30%, about 40%, about 50%, about 60%, about 70%, or any range between the recited values. In some embodiments, the solid dispersion can comprise the matrix polymer in an amount ranging from about 20-90% by weight, such as about 20%, about 30%, about 40%, about 50%, about 60%, about 70%, or about 80%, about 90%, any range between the recited values. Typically, the solid dispersion can comprise Compound 1 in an amount of about 20-60% by weight and the matrix polymer in an amount of about 40-80% by weight. In some embodiments, the solid dispersion can comprise Compound 1 in an amount of about 30-50% by weight and the matrix polymer in an amount of about 50-70% by weight.

In some exemplary embodiments, the solid dispersion herein comprises, consists essentially of, or consists of Compound 1 in an amorphous form dispersed (e.g., homogeneously dispersed) in a copolymer of 2-dimethylaminoethyl methacrylate, butyl methacrylate, and methyl methacrylate, such as poly((2-dimethylaminoethyl)methacrylate, butyl methacrylate, methyl methacrylate) (2:1:1), e.g., Eudragit®E100, wherein Compound 1 is in an amount of about 10% to about 80% by weight, such as about 20%, about 30%, about 40%, about 50%, about 60%, about 70%, or any range between the recited values, preferably about 20-60% by weight or about 35-45% by weight. In some embodiments, the weight ratio of Compound 1 to the copolymer of 2-dimethylaminoethyl methacrylate, butyl methacrylate, and methyl methacrylate, such as poly((2-dimethylaminoethyl)methacrylate, butyl methacrylate, methyl methacrylate) (2:1:1) (e.g., Eudragit®E100) ranges from about 1:20 to about 5:1, such as about 1:10, about 1:4, about 1:2, about 2:3, about 1:1, about 3:2, about 2:1, about 5:1 or any range between the recited values, preferably, about 1:4 to about 2:1. In some embodiments, the solid dispersion comprises about 30-50% by weight of Compound 1 and about 50-70% by weight of the copolymer of 2-dimethylaminoethyl methacrylate, butyl methacrylate, and methyl methacrylate, such as poly((2-dimethylaminoethyl)methacrylate, butyl methacrylate, methyl methacrylate) (2:1:1) (e.g., Eudragit®E100). In some embodiments, the solid dispersion is essentially free (e.g., less than 10%, less than 5%, less than 2%, etc.) of Compound 1 in a crystalline form. In some embodiments, the solid dispersion does not include Compound 1 in a crystalline form in an amount detectable by XRPD. In some embodiments, the solid dispersion is an amorphous solid dispersion. In some embodiments, the solid dispersion is a spray dried amorphous solid dispersion. In some embodiments, the solid dispersion is a stable amorphous solid dispersion. In some embodiments, the solid dispersion can be characterized by having one or more (e.g., two or more) of the following characteristics: 1) being an amorphous solid, 2) having a drug load of about 36.0% to about 44.0%, and 3) having an impurity level of 0.29% by weight or less for the impurity having a relative retention time to Compound 1 (RRT) at 1.03; an impurity level of 0.34% by weight or less for the impurity having a RRT at 1.15; an impurity level of 0.21% by weight or less for the impurity having a RRT at 1.66; an impurity level of 0.15% by weight or less for unspecified impurity; and a total impurity of less than 2.0% by weight. In some embodiments, the solid dispersion conforms to the specification shown in Table 17.

In some exemplary embodiments, the solid dispersion herein comprises, consists essentially of, or consists of Compound 1 in an amorphous form dispersed (e.g., homogeneously dispersed) in a graft copolymer of polyethylene glycol, polyvinyl acetate and polyvinylcaprolactam (e.g., Soluplus®), wherein Compound 1 is in an amount of about 10% to about 80% by weight, such as about 20%, about 30%, about 40%, about 50%, about 60%, about 70%, or any range between the recited values, preferably about 20-60% by weight or about 35-45% by weight. In some embodiments, the weight ratio of Compound 1 to the graft copolymer of polyethylene glycol, polyvinyl acetate and polyvinylcaprolactam (e.g., Soluplus®) ranges from about 1:20 to about 5:1, such as about 1:10, about 1:4, about 1:2, about 2:3, about 1:1, about 3:2, about 2:1, about 5:1 or any range between the recited values, preferably, about 1:4 to about 2:1. In some embodiments, the solid dispersion comprises about 30-50% by weight of Compound 1 and about 50-70% by weight of the graft copolymer of polyethylene glycol, polyvinyl acetate and polyvinylcaprolactam (e.g., Soluplus®). In some embodiments, the solid dispersion is essentially free (e.g., less than 10%, less than 5%, less than 2%, etc.) of Compound 1 in a crystalline form. In some embodiments, the solid dispersion does not include Compound 1 in a crystalline form in an amount detectable by XRPD. In some embodiments, the solid dispersion is an amorphous solid dispersion. In some embodiments, the solid dispersion is a spray dried amorphous solid dispersion. In some embodiments, the solid dispersion is a stable amorphous solid dispersion.

In some exemplary embodiments, the solid dispersion herein comprises, consists essentially of, or consists of Compound 1 in an amorphous form dispersed (e.g., homogeneously dispersed) in HPMC, e.g., HPMC E3 LV, wherein Compound 1 is in an amount of about 10% to about 80% by weight, such as about 20%, about 30%, about 40%, about 50%, about 60%, about 70%, or any range between the recited values, preferably about 20-60% by weight or about 35-45% by weight. In some embodiments, the weight ratio of Compound 1 to HPMC (e.g., HPMC E3 LV) ranges from about 1:20 to about 5:1, such as about 1:10, about 1:4, about 1:2, about 2:3, about 1:1, about 3:2, about 2:1, about 5:1 or any range between the recited values, preferably, about 1:4 to about 2:1. In some embodiments, the solid dispersion comprises about 30-50% by weight of Compound 1 and about 50-70% by weight of HPMC (HPMC E3 LV). In some embodiments, the solid dispersion is essentially free (e.g., less than 10%, less than 5%, less than 2%, etc.) of Compound 1 in a crystalline form. In some embodiments, the solid dispersion does not include Compound 1 in a crystalline form in an amount detectable by XRPD. In some embodiments, the solid dispersion is an amorphous solid dispersion. In some embodiments, the solid dispersion is a spray dried amorphous solid dispersion. In some embodiments, the solid dispersion is a stable amorphous solid dispersion.

In some exemplary embodiments, the solid dispersion herein comprises, consists essentially of, or consists of Compound 1 in an amorphous form dispersed (e.g., homogeneously dispersed) in hydroxypropyl cellulose, HPC-SSL, wherein Compound 1 is in an amount of about 10% to about 80% by weight, such as about 20%, about 30%, about 40%, about 50%, about 60%, about 70%, or any range between the recited values, preferably about 20-60% by weight or about 35-45% by weight. In some embodiments, the weight ratio of Compound 1 to hydroxypropyl cellulose (e.g., HPC-SSL) ranges from about 1:20 to about 5:1, such as about 1:10, about 1:4, about 1:2, about 2:3, about 1:1, about 3:2, about 2:1, about 5:1 or any range between the recited values, preferably, about 1:4 to about 2:1. In some embodiments, the solid dispersion comprises about 30-50% by weight of Compound 1 and about 50-70% by weight of hydroxypropyl cellulose (e.g., HPC-SSL). In some embodiments, the solid dispersion is essentially free (e.g., less than 10%, less than 5%, less than 2%, etc.) of Compound 1 in a crystalline form. In some embodiments, the solid dispersion does not include Compound 1 in a crystalline form in an amount detectable by XRPD. In some embodiments, the solid dispersion is an amorphous solid dispersion. In some embodiments, the solid dispersion is a spray dried amorphous solid dispersion. In some embodiments, the solid dispersion is a stable amorphous solid dispersion.

In any of the embodiments described herein, the solid dispersion herein can be characterized as being storage stable, for example, the solid dispersion can be characterized in that, upon storage at 2-8° C., 25° C. and 60% relative humidity, or 40° C. and 75% relative humidity for one week or longer, such as up to 6 months or longer, the solid dispersion does not have Compound 1 in a crystalline form in an amount detectable by XRPD. Typically, a storage stable solid dispersion herein can also be characterized as having no significant changes in terms of the amount of related substance of Compound 1 and/or the assay amount of Compound 1, after being stored at 25° C. and 60% relative humidity or 40° C. and 75% relative humidity for one week or longer, such as up to 6 months or longer.

The solid dispersion herein can be prepared by those skilled in the art in view of the present disclosure.

Processes of Preparing Solid Dispersion of Compound 1

Some embodiments of the present disclosure are also directed to methods of preparing a solid dispersion of Compound 1. Typically, the method comprises (a) mixing Compound 1, a polymer (e.g., described herein) in a solvent to form a solution, and (b) removing the solvent to provide the solid dispersion. The solvent can be removed through any known means, including but not limited to spray drying, evaporation, freeze drying, etc. In some embodiments, the method can also comprise a solventless process. For example, in some embodiments, the method can comprise mixing Compound 1 and a polymer (e.g., described herein) to form a mixture, followed by hot melt extrusion of the mixture to provide the solid dispersion.

In some preferred embodiments, the present disclosure provides a method of preparing a solid dispersion, the method comprises: (a) mixing Compound 1, a polymer, and a solvent to form a solution; and (b) spray-drying the solution of step (a), thereby obtaining the solid dispersion.

Starting Compound 1 for Preparing Solid Dispersions

The starting Compound 1 (e.g., the Compound 1 used to form the solution in step (a) above) useful for the methods of preparation herein is not particularly limited, although it is typically in a substantially pure form. For example, typically, the starting Compound 1 can have a purity of greater than 70%, preferably greater than 90% (e.g., greater than 95%, greater than 97%, greater than 98%, greater than 98.5%), by weight, by HPLC area, or both. In some embodiments, the starting Compound 1 can be characterized by a purity by weight and/or by HPLC area of about 70%, about 75%, about 80%, about 85%, about 90%, about 95%, about 97%, about 99%, or any ranges between the specified values. For example, in some embodiments, the starting Compound 1 can be characterized by a purity by HPLC area of about 70%, about 75%, about 80%, about 85%, about 90%, about 95%, about 97%, about 99%, or any ranges between the specified values. The substantially pure Compound 1 can be in a solid form (e.g., a crystalline form described herein, amorphous form, or a combination thereof) or in a solution, suspension, or another form. In some embodiments, the substantially pure Compound 1 can be in crystalline Form B.

In some embodiments, the starting Compound 1 for the methods of preparation herein can be in a solid form, such as an amorphous form, a crystalline form, or a combination thereof. In some embodiments, the starting Compound 1 can be an amorphous form. In some embodiments, the starting Compound 1 can be in a crystalline form (e.g., in crystalline form A or B). As used herein, when Compound 1 is said to exist or be in one particular solid form (e.g., a crystalline form), it should be understood that in some embodiments, it can exist predominantly in that particular form. However, in some embodiments, Compound 1 can also exist in the particular form, in a mixture with one or more other solid forms, including amorphous form. For example, when Compound 1 is said to exist or be in Form B, Compound 1 can exist predominantly in Form B, such as more than 80% by weight, more than 90% by weight, or more than 95% by weight of Compound 1 are in Form B, or no other solid form can be identified, for example, by XRPD; or Compound 1 can exist in Form B, in a mixture with one or more solid forms such as an amorphous form. Similarly, when Compound 1 is said to exist or be in an amorphous form, Compound 1 can exist predominantly in an amorphous form, such as more than 80% by weight, more than 90% by weight, or more than 95% by weight of Compound 1 are in an amorphous form, or no other solid form can be identified, for example, by XRPD; or Compound 1 can exist in an amorphous form, in a mixture with one or more solid forms such as a crystalline form. In any of the embodiments described herein, unless otherwise specified or contrary from context, Compound 1 can exist predominantly in an amorphous form, such as more than 80% by weight, more than 90% by weight, or more than 95% by weight of Compound 1 is in an amorphous form, or no other solid form such as crystalline form(s) of Compound 1 can be identified, for example, by XRPD.

Figure 1B:
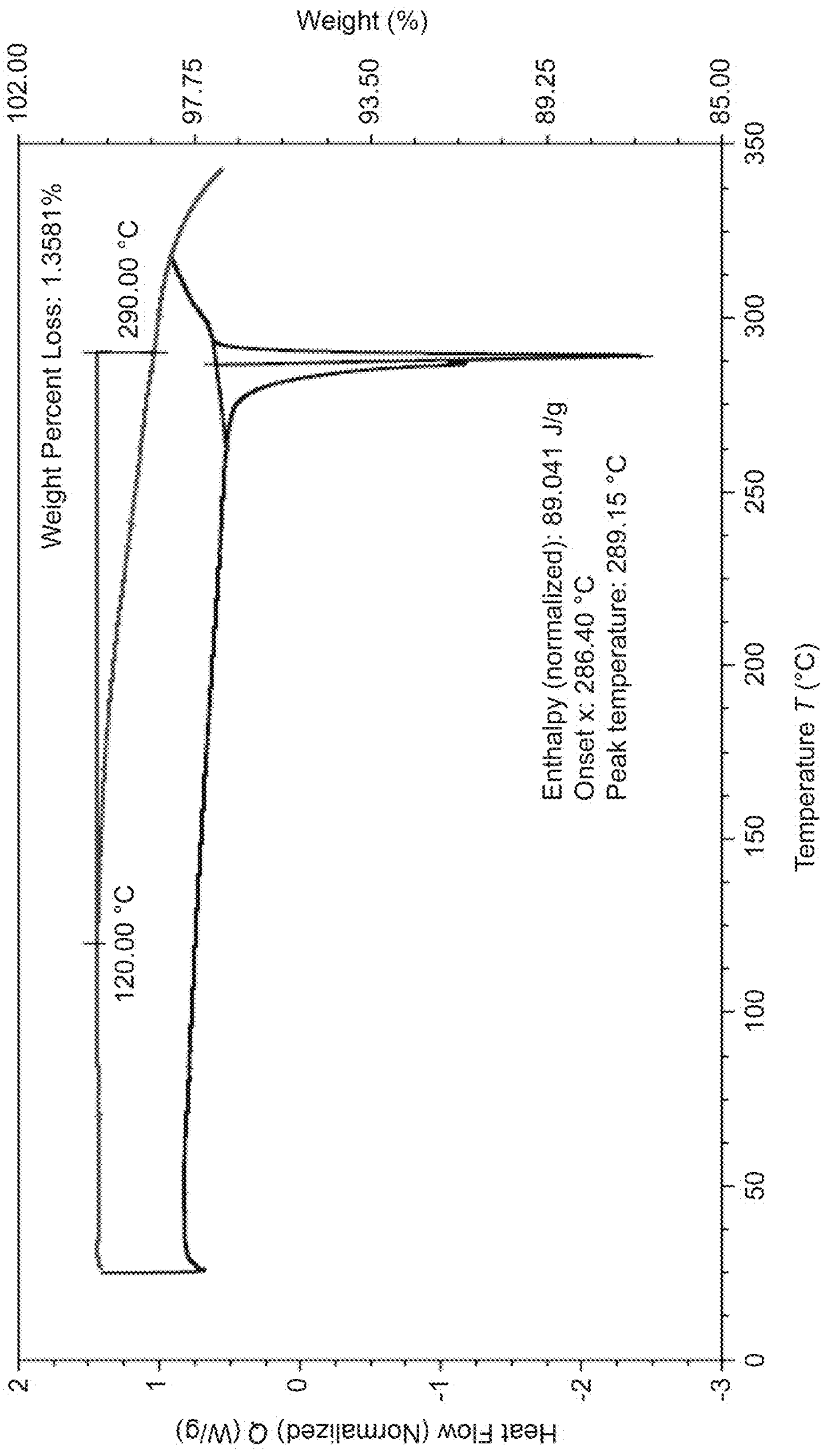

In some embodiments, the starting Compound 1 is in a crystalline Form A. Characteristics of Form A include any of those described herein. In some embodiments, crystalline Form A can be characterized by (1) an X-ray powder diffraction (XRPD) pattern having one or more (e.g., 1, 2, 3, or 4) of the following peaks: 6.2, 12.6, 14.8, and 19.9 degrees 2 theta, ±0.2°; (2) an X-ray powder diffraction (XRPD) pattern having one or more (e.g., 4 or more, 6 or more, or all) of the following peaks: 6.2, 12.6, 13.8, 14.8, 15.1, 18.0, 19.6 and 19.9 degrees 2 theta, ±0.2°; (3) an XRPD pattern substantially the same as shown in FIG. 1A; (4) a Differential Scanning calorimetry (DSC) pattern substantially the same as shown in FIG. 1B; or any combination thereof (e.g., (1) and (4), (2) and (4), (1), (2) and (4), or (3) and (4)). In some embodiments, the crystalline Form A can be characterized by an XRPD pattern having the major peaks (e.g., peaks with relative intensity of 20% or above, 30% or above, 40% or above, 50% or above, 60% or above, 70% or above, 80% or above, or 90% or above) of FIG. 1A or as shown in Table 1, degrees 2 theta, ±0.2°. In some embodiments, the crystalline Form A can be characterized by an XRPD pattern having all of the following peaks: 6.2, 12.6, 14.8, and 19.9 degrees 2 theta, ±0.2°. In some embodiments, the crystalline Form A can be characterized by an XRPD pattern having none of the following peaks: 7.3, 14.2, 15.7, and 16.3 degrees 2 theta, ±0.2°. In some embodiments, the crystalline Form A can be characterized by an XRPD pattern that does not have two or more, three or more, or all of the following peaks: 7.3, 14.2, 15.7, and 16.3 degrees 2 theta, ±0.2°. In some embodiments, the crystalline Form A can be characterized by an XRPD pattern having none of the following peaks: 14.5, 15.6, 20.2, and 38.6 degrees 2 theta, ±0.2°. In some embodiments, the crystalline Form A can be characterized by an XRPD pattern that does not have two or more, three or more, or all of the following peaks: 14.5, 15.6, 20.2, and 38.6 degrees 2 theta, ±0.2°. In some embodiments, the crystalline Form A can also be characterized by a DSC pattern having an endothermic peak with an onset temperature of about 286.4° C. and/or peak temperature at about 289.2° C. In some embodiments, the crystalline Form A is substantially the same as the crystalline Form A obtained in Example 3 of this application.

The starting Compound 1 in crystalline Form A can be prepared by methods described herein. For example, in some embodiments, Compound 1 in crystalline Form A can be prepared by a method comprising slurring Compound 1 in a solvent, such as ethyl acetate (EA or EtOAc), or by a method comprising 1) dissolving Compound 2 in an appropriate solvent, such as acetone, THF, 2-butanone and/or dichloromethane (DCM), and then 2) adding anti-solvent, such as n-heptane, to precipitate Compound 1. Exemplified procedures for preparing Compound 1 in Form A are shown in Example 3 of this application, see also PCT/CN2020/137276 and PCT/CN2019/126230.

Figure 2A:
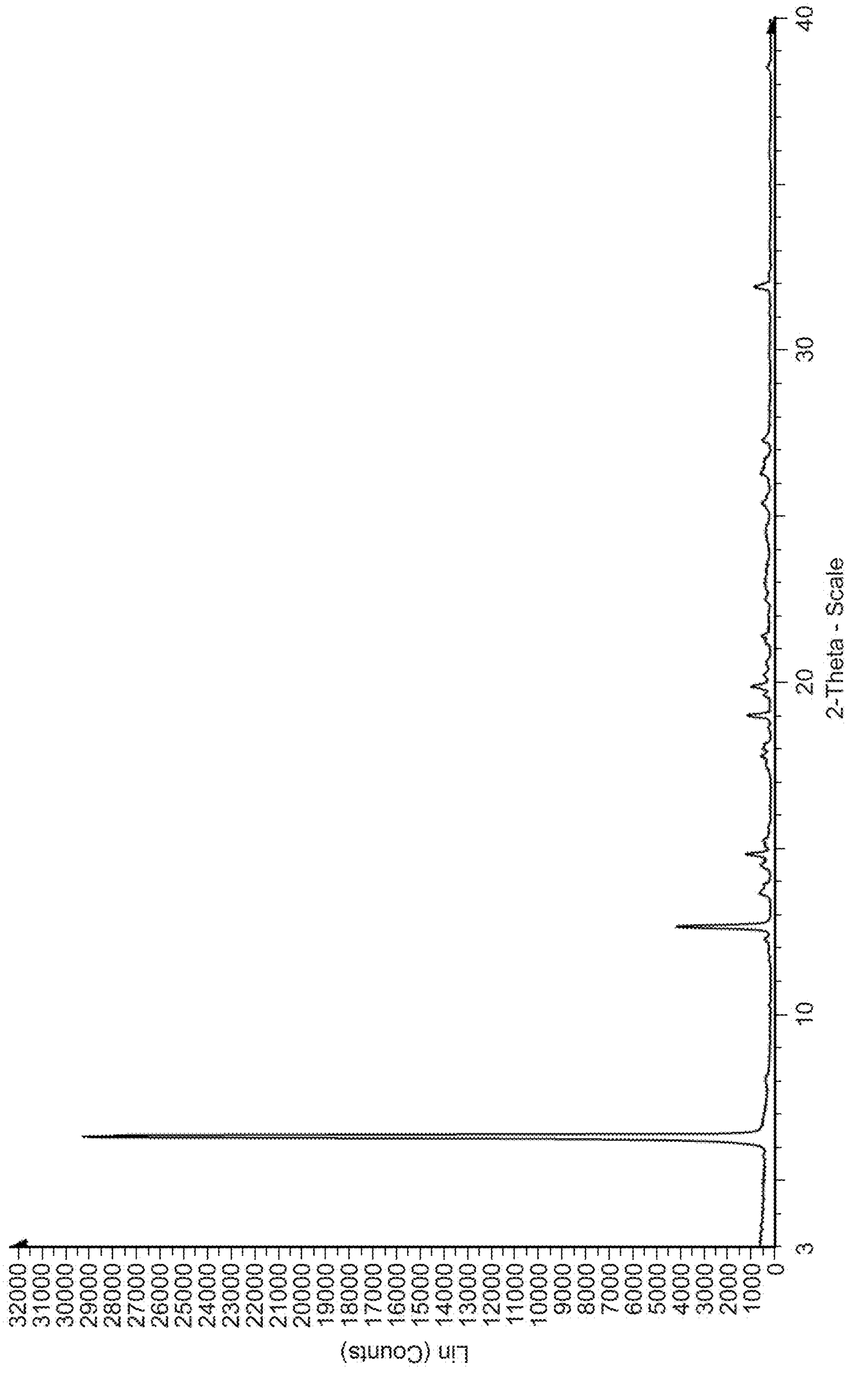
Figure 2B:
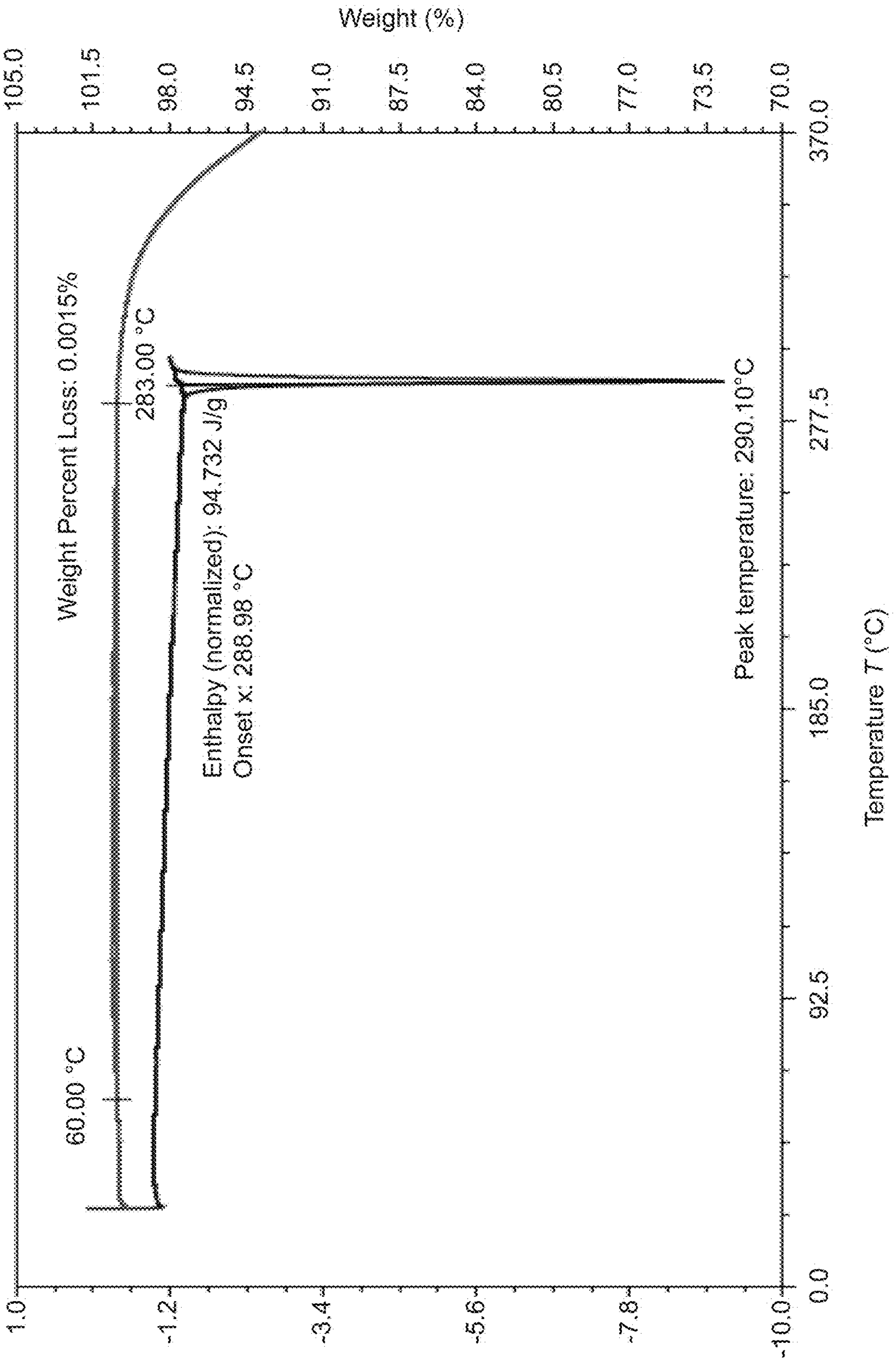

In some embodiments, the starting Compound 1 is in a crystalline Form B. Characteristics of Form B include any of those described herein. In some embodiments, crystalline Form B can be characterized by (1) an X-ray powder diffraction (XRPD) pattern having one or more (e.g., 1, 2, 3, 4, or 5) of the following peaks: 6.2, 12.6, 14.8, 19.0, and 19.8 degrees 2 theta, ±0.2°; (2) an X-ray powder diffraction (XRPD) pattern having one or more (e.g., 4 or more, 6 or more, 8 or more, or all) of the following peaks: 6.2, 12.6, 13.6, 14.5, 14.8, 17.8, 19.0, 19.8, 21.4, 26.3, 31.9 and 38.6 degrees 2 theta, ±0.2°; (3) an XRPD pattern substantially the same as shown in FIG. 2A; (4) a Differential Scanning calorimetry (DSC) pattern substantially the same as shown in FIG. 2B; or any combination thereof (e.g., (1) and (4), (2) and (4), (1), (2) and (4), or (3) and (4)). In some embodiments, the crystalline Form B can be characterized by an XRPD pattern having the major peaks (e.g., peaks with relative intensity of 20% or above, 30% or above, 40% or above, 50% or above, 60% or above, 70% or above, 80% or above, or 90% or above) of FIG. 2A or as shown in Table 2, degrees 2 theta, ±0.2°. In some embodiments, the crystalline Form B can be characterized by an XRPD pattern having all of the following peaks: 6.2, 12.6, 14.8, 19.0, and 19.8 degrees 2 theta, ±0.2°. In some embodiments, the crystalline Form B can be characterized by an XRPD pattern having at least one (e.g., 1, 2, 3, 4, 5, or 6) of the following peaks: 14.5, 17.8, 21.4, 26.3, 31.9 and 38.6 degrees 2 theta, ±0.2°. In some embodiments, the crystalline Form B can be characterized by an XRPD pattern having all of the following peaks: 6.2, 12.6, 14.8, 19.0, and 19.8 degrees 2 theta, ±0.2° and at least one (e.g., 1, 2, 3, 4, 5, or 6) of the following peaks: 14.5, 17.8, 21.4, 26.3, 31.9 and 38.6 degrees 2 theta, ±0.2°. In some embodiments, the crystalline Form B can be characterized by an XRPD pattern that has all of the following peaks: 6.2, 12.6, 14.8, 19.0, and 19.8 degrees 2 theta, ±0.2°; has two or more, three or more, or all of the following peaks: 14.5, 15.6, 20.2, and 38.6 degrees 2 theta, ±0.2°; and does not have either or both peaks at 7.3 and 14.2 degrees 2 theta, ±0.2°. In some embodiments, the crystalline Form B can also be characterized by a DSC pattern having an endothermic peak with an onset temperature of about 289.0° C. and/or peak temperature at about 290.1° C. In some embodiments, the crystalline Form B is substantially the same as the crystalline Form B obtained in Example 2 or 3 of this application.

The starting Compound 1 in crystalline Form B can be prepared by methods described herein. For example, in some embodiments, Compound 1 in crystalline Form B can be prepared by a method comprising 1) dissolving Compound 1 in a first solvent, e.g., at room temperature, such as methanol, to form a solution; and then 2) adding an anti-solvent, such as water, to the solution to precipitate Compound 1. In some embodiments, the method further comprises stirring the mixture of Compound 1 in the first solvent and the anti-solvent, e.g., at room temperature, for a period of time (e.g., 1-24 hours), to form a suspension; and optionally filtering and drying the precipitated Compound 1. In some embodiments, Compound 1 in crystalline Form B can be prepared from a different crystalline form. For example, in some embodiments, Compound 1 in crystalline Form B can be prepared by a method comprising 1) suspending Compound 1 (e.g., in Form A) in a solvent, such as methanol, to form a suspension; and 2) stirring the suspension at room temperature (RT) or under heat, such as at 50° C., for a period of time, such as 1 day, 3 days, etc. to form Compound 1 in crystalline Form B. The concentration of the suspension with the solvent can range from 15-100 mg/mL, such as about 100 mg/mL. Exemplified procedures for preparing Compound 1 in Form B are shown in Examples 2 and 3 of this application, see also PCT/CN2020/137276 and PCT/CN2019/126230.

Figure 6A:
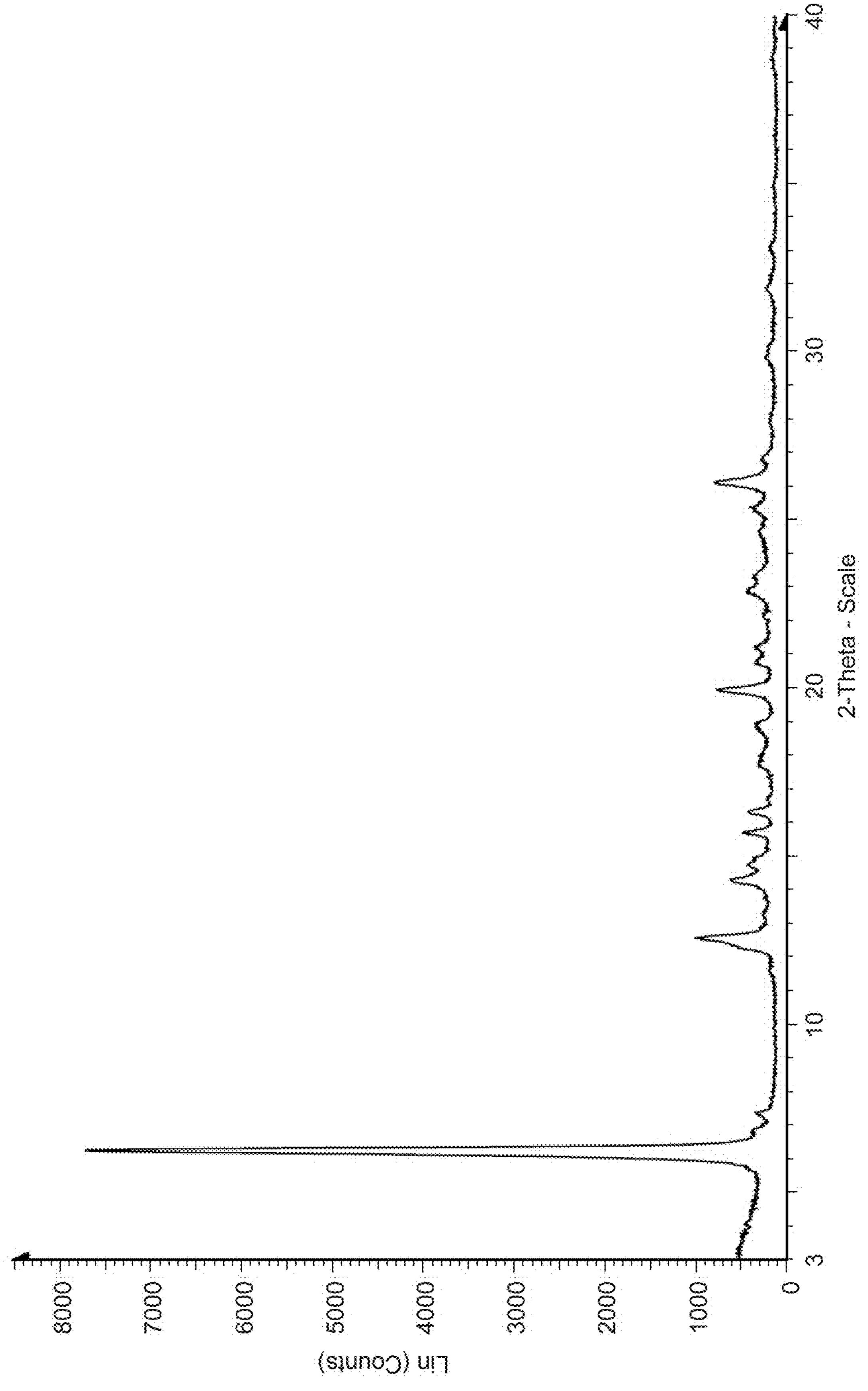
FIG. 6A shows a representative X-ray powder diffraction (XRPD) spectrum of crystalline form C of Compound 1.
Figure 6B:
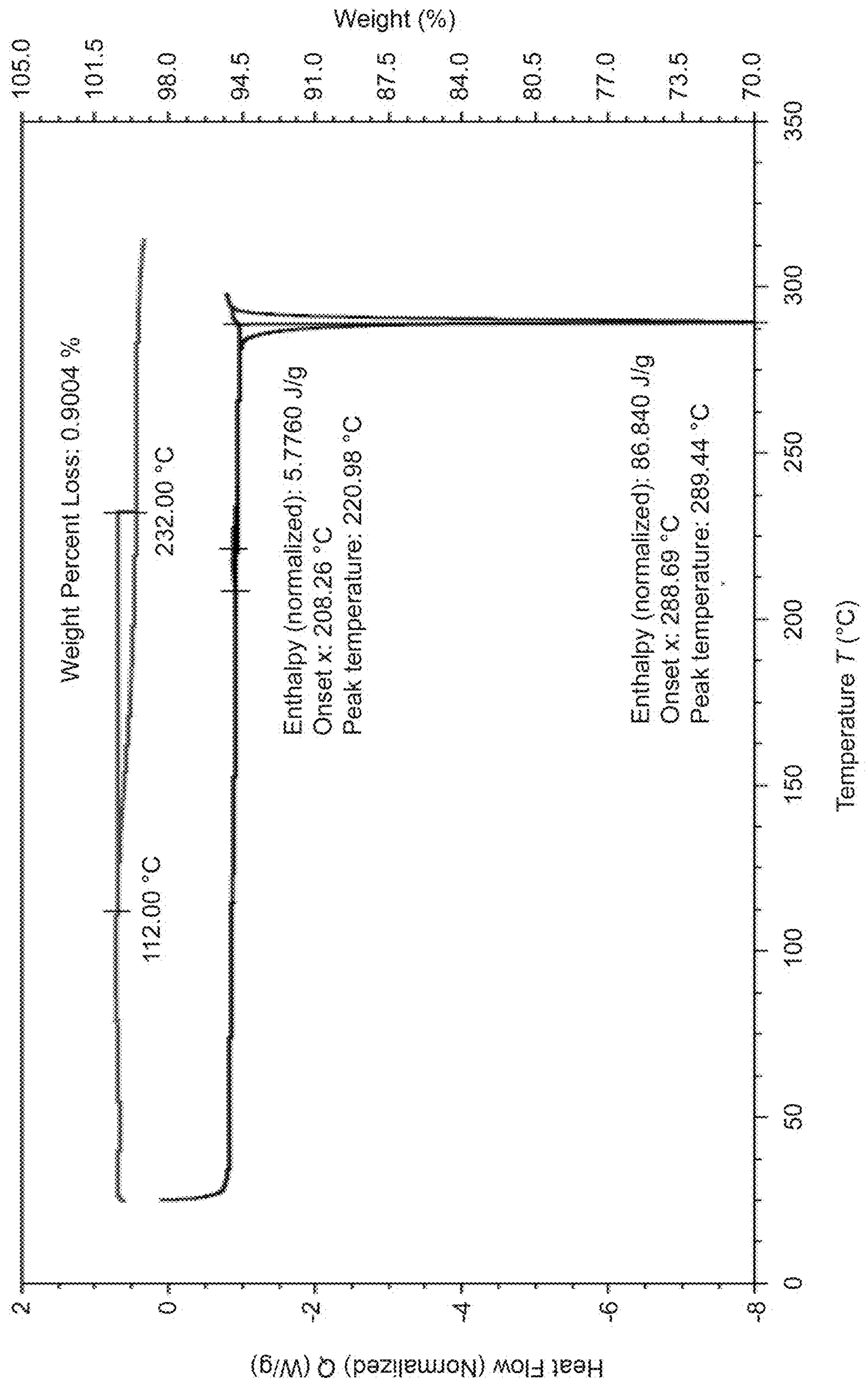
FIG. 6B shows a representative thermogravimetric analysis (TGA) and differential scanning calorimetry (DSC) analysis of crystalline form C of Compound 1.

In some embodiments, the starting Compound 1 is in a crystalline Form C. Characteristics of Form C include any of those described herein. In some embodiments, crystalline Form C can be characterized by (1) an X-ray powder diffraction (XRPD) pattern having one or more (e.g., 1, 2, or 3) of the following peaks: 6.2, 12.5, and 19.9 degrees 2 theta, ±0.2°; (2) an X-ray powder diffraction (XRPD) pattern having one or more (e.g., 4 or more, 8 or more, or all) of the following peaks: 6.2, 6.8, 7.3, 12.5, 14.2, 14.7, 15.7, 16.3, 19.9, 21.2, 22.9 and 26.1 degrees 2 theta, ±0.2°; (3) an XRPD pattern substantially the same as shown in FIG. 6A; (4) a Differential Scanning calorimetry (DSC) pattern substantially the same as shown in FIG. 6B; or any combination thereof (e.g., (1) and (4), (2) and (4), (1), (2) and (4), or (3) and (4)). In some embodiments, the crystalline Form C can be characterized by an XRPD pattern having the major peaks (e.g., peaks with relative intensity of 20% or above, 30% or above, 40% or above, 50% or above, 60% or above, 70% or above, 80% or above, or 90% or above) of FIG. 6A, degrees 2 theta, ±0.2°. In some embodiments, the crystalline Form C can be characterized by an XRPD pattern having all of the following peaks: 6.2, 12.5, and 19.9 degrees 2 theta, ±0.2°. In some embodiments, the crystalline Form C can be characterized by an XRPD pattern having at least one (e.g., 1, 2, 3, 4, 5, 6, 7, 8, or all) of the following peaks: 7.3, 14.2, 14.7, 15.7, 16.3, 19.9, 21.2, 22.9 and 26.1 degrees 2 theta, ±0.2°. In some embodiments, the crystalline Form C can be characterized by an XRPD pattern having all of the following peaks: 6.2, 12.5, and 19.9 degrees 2 theta, ±0.2° and at least one (e.g., 1, 2, 3, or 4) of the following peaks: 7.3, 14.2, 20.8, and 26.1 degrees 2 theta, ±0.2°. In some embodiments, the crystalline Form C can be characterized by an XRPD pattern that has all of the following peaks: 6.2, 12.5, and 19.9 degrees 2 theta, ±0.2°; and has either or both peaks at 7.3 and 14.2 degrees 2 theta, ±0.2°. In some embodiments, the crystalline Form C can also be characterized by a DSC pattern having an endothermic peak with an onset temperature of about 288.7° C. and/or peak temperature at about 289.4° C. In some embodiments, the crystalline Form C is substantially the same as the crystalline Form C obtained in Example 6 of PCT/CN2020/137276. The Compound 1 in crystalline Form C can be prepared by methods described in PCT/CN2020/137276 and PCT/CN2019/126230.

Figure 7A:
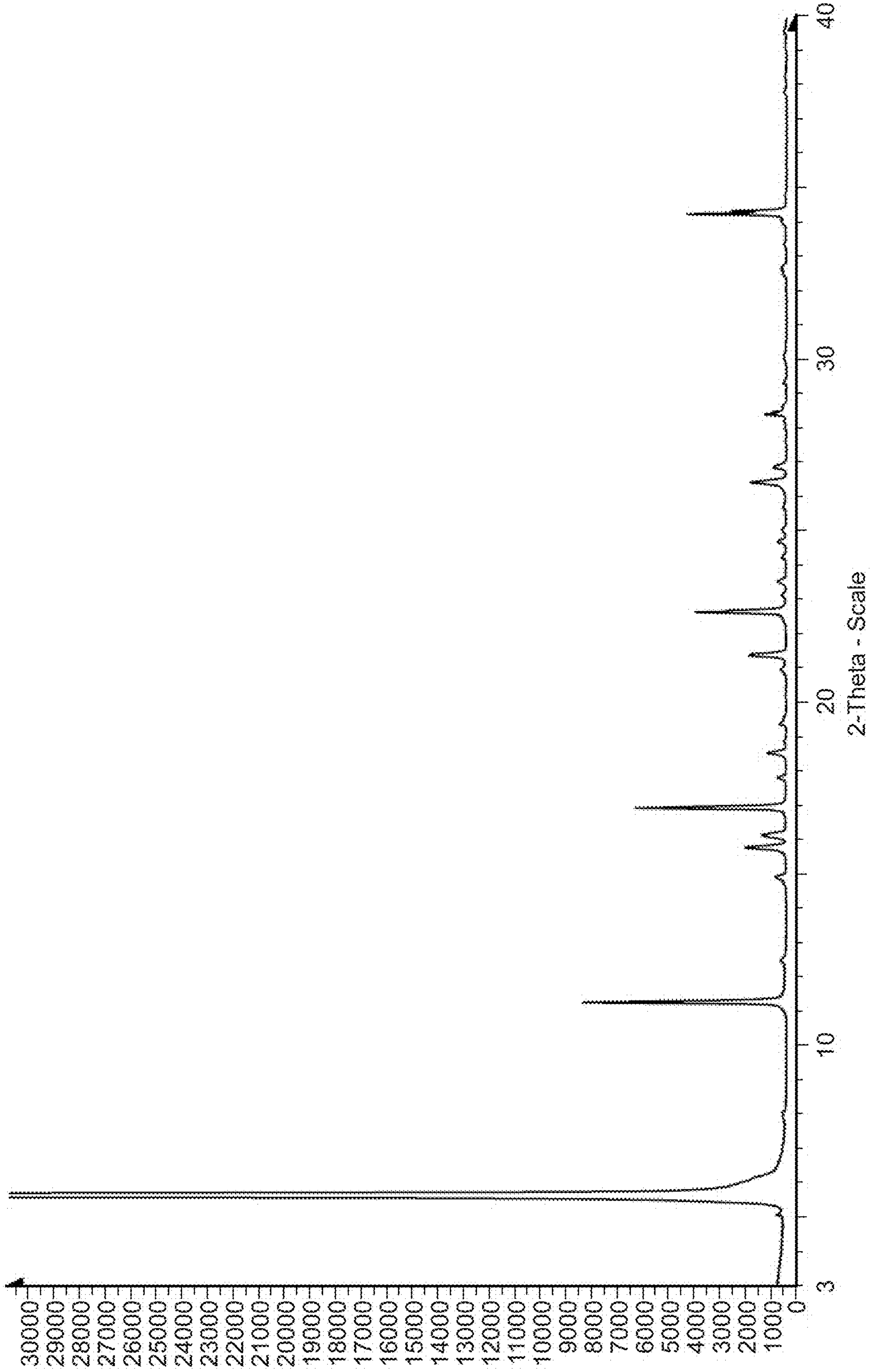
FIG. 7A shows a representative X-ray powder diffraction (XRPD) spectrum of crystalline form D of Compound 1.
Figure 7B:
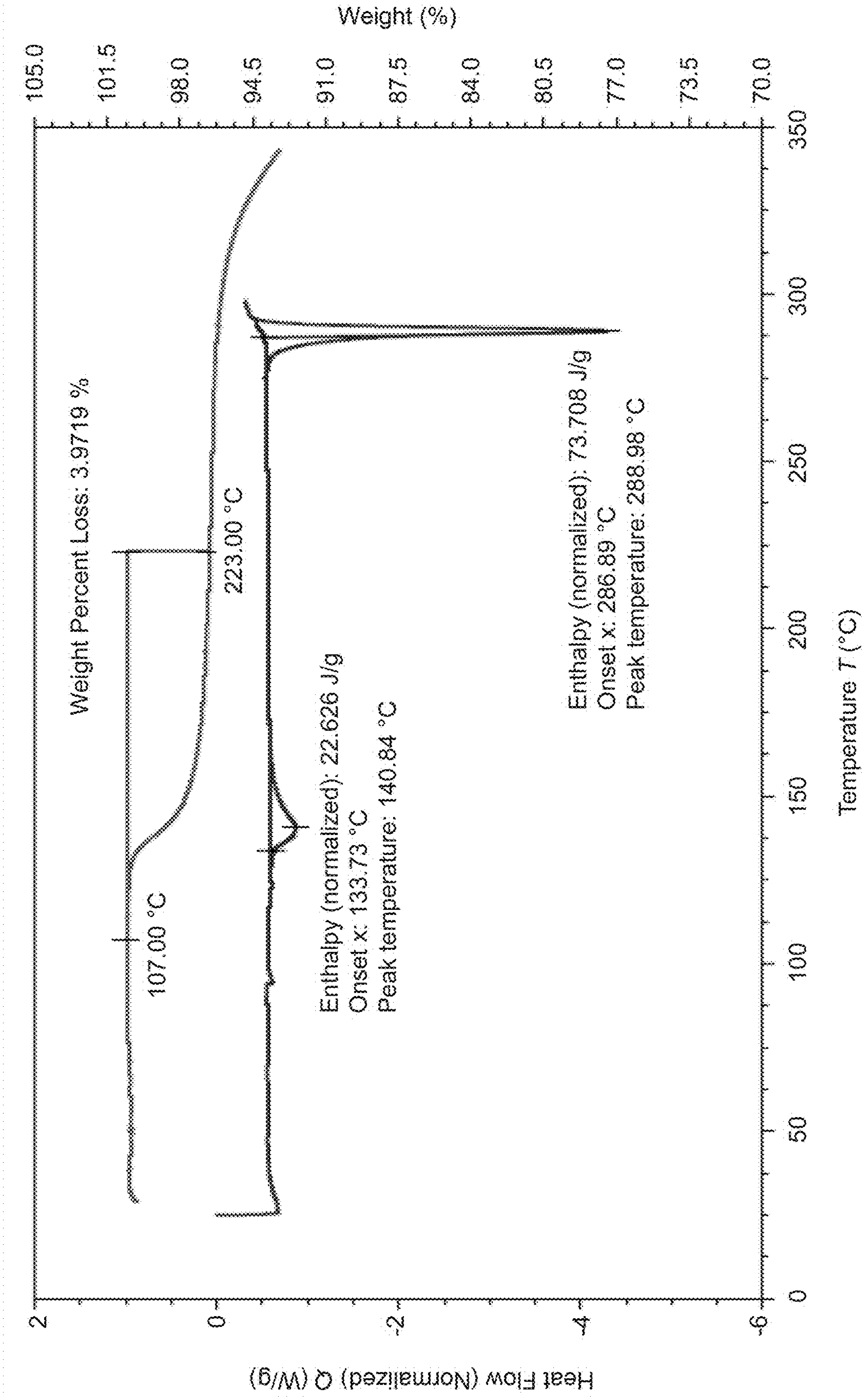
FIG. 7B shows a representative thermogravimetric analysis (TGA) and differential scanning calorimetry (DSC) analysis of crystalline form D of Compound 1.

In some embodiments, the starting Compound 1 is in a crystalline Form D. Characteristics of Form D include any of those described herein. In some embodiments, crystalline Form D can be characterized by (1) an X-ray powder diffraction (XRPD) pattern having one or more (e.g., 1, 2, 3, or 4) of the following peaks: 5.6, 11.2, 16.9, and 22.6 degrees 2 theta, ±0.2°; (2) an X-ray powder diffraction (XRPD) pattern having one or more (e.g., 2 or more, 4 or more, 6 or more, or all) of the following peaks: 5.6, 11.2, 15.8, 16.1, 16.9, 21.4, 22.6 and 34.3 degrees 2 theta, ±0.2°; (3) an XRPD pattern substantially the same as shown in FIG. 7A; (4) a Differential Scanning calorimetry (DSC) pattern substantially the same as shown in FIG. 7B; or any combination thereof (e.g., (1) and (4), (2) and (4), (1), (2) and (4), or (3) and (4)). In some embodiments, the crystalline Form D can be characterized by an XRPD pattern having the major peaks (e.g., peaks with relative intensity of 20% or above, 30% or above, 40% or above, 50% or above, 60% or above, 70% or above, 80% or above, or 90% or above) of FIG. 7A, degrees 2 theta, ±0.2°. In some embodiments, the crystalline Form D can be characterized by an XRPD pattern having all of the following peaks: 5.6, 11.2, 16.9, and 22.6 degrees 2 theta, ±0.2°. In some embodiments, the crystalline Form D can be characterized by an XRPD pattern having at least one (e.g., 1, 2, 3, 4, 5, 6, 7, or 8) of the following peaks: 5.6, 11.2, 15.8, 16.1, 16.9, 21.4, 22.6 and 34.3 degrees 2 theta, ±0.2°. In some embodiments, the crystalline Form D can also be characterized by a DSC pattern having an endothermic peak with an onset temperature of about 286.9° C. and/or peak temperature at about 289.0° C. and an endothermic peak with an onset temperature of about 133.7° C. and/or peak temperature at about 140.8° C. In some embodiments, the crystalline Form D is substantially the same as the crystalline Form D obtained in Example 6 of PCT/CN2020/137276.

The starting Compound 1 in crystalline Form D can be prepared by methods described in PCT/CN2020/137276. For example, in some embodiments, Compound 1 in crystalline Form D can be prepared by a method comprising 1) dissolving Compound 1 in a first solvent, such as isopropanol or isobutanol, to form a first solution, e.g., saturated solution; and then 2) dissolving Compound 1 in a second solvent, such as 2-butanone, acetone, or THF, to form a second solution, e.g., saturated solution; 3) mixing the first and second solution; and 4) precipitating Compound 1 through slow evaporation of solvents. In some embodiments, the first and second solvent can be isopropanol and 2-butanone, isopropanol and THF, isopropanol and acetone, or isobutanol and THF. Exemplified procedures for preparing Compound 1 in Form D are shown in PCT/CN2020/137276 and PCT/CN2019/126230.

In some embodiments, the starting Compound 1 can be in an amorphous form. Amorphous form of Compound 1 can be prepared by various methods described herein, for example, by spray drying a solution of Compound 1, such as a solution of Compound 1 in a solvent selected from acetone, dichloromethane, methanol, or any combination thereof.

The starting Compound 1 in various solid forms are also novel compositions of the present disclosure. In addition, the present disclosure also provides novel solid forms of starting Compound 1 that can be produced by any of the applicable methods described in the Examples section herein. In some embodiments, the present disclosure is also directed to any products produced by any of the methods herein, and methods of using such products.

Compound 1 can be synthesized by various methods, for example, those described in International Application Nos. PCT/CN2020/091274, filed May 20, 2020, published as WO2020/233592, and PCT/CN2020/137276, filed Dec. 17, 2020.

In some embodiments, the present disclosure also provides a new synthetic method and synthetic intermediates for preparing Compound 1. Typically, the synthetic method can include a) reacting compound 1-8 or a salt thereof with

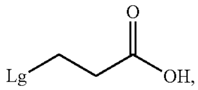
, or an activated form thereof (e.g., acyl halide or anhydride) under an amide forming condition to form a compound of Formula I-Lg, wherein Lg is a leaving group (e.g., a halide or an oxygen-containing leaving group such as tosylate), and b) converting the compound of Formula I-Lg under an elimination condition to form Compound 1:

1-8

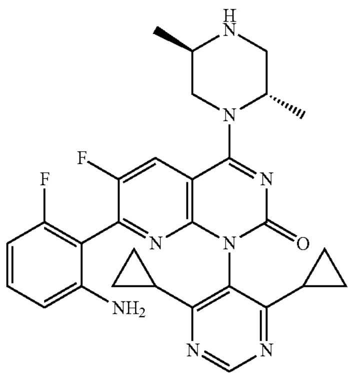

I-Lg

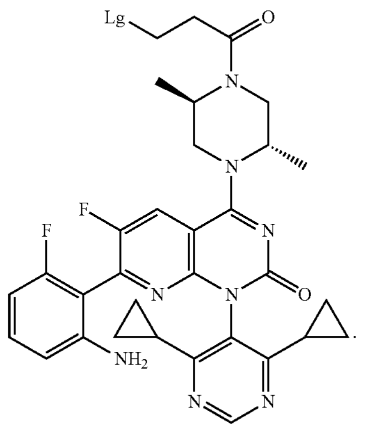

Suitable amide forming conditions are not particularly limited and include any of those known in the art and those exemplified herein. Typically, the synthetic method comprises reacting of compound 1-8 with an acyl chloride

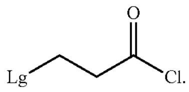

The Lg in Formula I-Lg and the acyl chloride is typically Cl. Conversion of the compound of Formula I-Lg into Compound 1 can be carried out via any suitable elimination conditions. Typically, such elimination is conducted in the presence of a base, such as a tertiary amine base, e.g., DBU (1,8-Diazabicyclo[5.4.0]undec-7-ene).

The compound 1-8 can be prepared by various methods, an exemplified procedure is also described herein. In some embodiments, the compound 1-8 can be prepared from deprotection of a compound of Formula I-P1:

I-P1

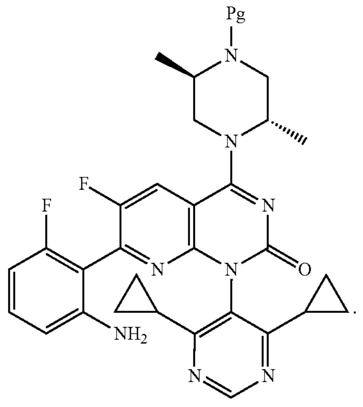

Any suitable nitrogen protecting group can be used as Pg in Formula I-P1, which includes those described in *Protective Groups in Organic Synthesis*, T. W. Greene and P. G. M. Wuts, $3^{rd}$ edition, John Wiley & Sons, 1999, incorporated by reference herein. Exemplary nitrogen protecting groups include, but not limited to, those forming carbamates, such as Carbobenzyloxy (Cbz) group, p-Methoxybenzyl carbonyl (Moz or MeOZ) group, tert-Butyloxycarbonyl (BOC) group, Troc, 9-Fluorenylmethyloxycarbonyl (Fmoc) group, etc., those forming an amide, such as acetyl, benzoyl, etc., those forming a benzylic amine, such as benzyl, p-methoxybenzyl, 3,4-dimethoxybenzyl, etc., those forming a sulfonamide, such as tosyl, Nosyl, etc., and others such as p-methoxyphenyl. In some embodiments, Pg in Formula I-P1 is a nitrogen protecting group that can be deprotected by an acid, such as trifluoroacetic acid (TFA), for example, in some embodiments, Pg is a Boc group.

Compounds of I-PI can be prepared by various methods, an exemplified procedure is also described herein. In some embodiments, the compound of Formula I-PI can be prepared by coupling of a compound of Formula I-P2 with a compound of Formula I-P3:

I-P2

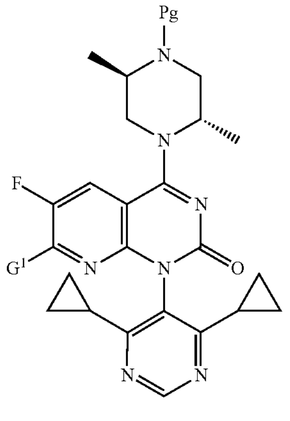

I-P3

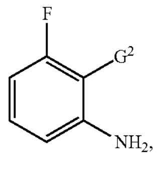

wherein Pg is defined herein, and $G^1$ and $G^2$ can be any suitable pair of coupling partners, e.g., for a palladium catalyzed cross-coupling reaction. For example, in some embodiments, $G^1$ is a leaving group, such as a halide or an oxygen-containing leaving group, and $G^2$ is a boronic acid, boronic ester, metal, or a residue such that the compound of Formula I-P3 is suitable for cross-coupling with the compound of Formula I-P2. In some embodiments, $G^1$ is Cl, and $G^2$ is $B(OH)_2$ or

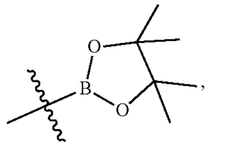 [SMILES: *B1OC(C)(C)C(C)(C)O1]

wherein the coupling of compounds of Formula I-P2 and I-P3 is mediated by a palladium catalyst. Suitable conditions for coupling of compounds of Formula I-P2 and I-P3 include any of those known in the art for analogous coupling reactions.

Compounds of I-P2 can also be prepared by various methods, an exemplified procedure is also described herein. In some embodiments, the compound of Formula I-P2 can be prepared by reacting a compound of Formula I-P4 with a compound of Formula I-P5:

I-P4

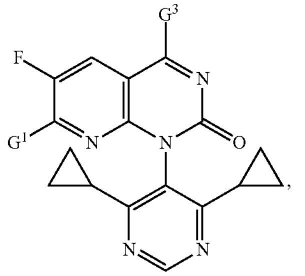

I-P5

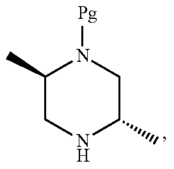

wherein $G^1$ and Pg are defined herein, and $G^3$ is a leaving group, such as a halide. In some embodiments, $G^1$ and $G^3$ in Formula I-P4 are both Cl. The reacting of the compounds of Formula I-P4 and Formula I-P5 is typically conducted in the presence of a base, such as a tertiary amine base, e.g., DIPEA (diisopropyl ethyl amine). An exemplified procedure is described herein in the Examples section.

In some embodiments, the present disclosure also provides a method of synthesizing Compound 1, which is substantially the same as the method described in the Examples section herein.

In some embodiments, the present disclosure also provides a synthetic intermediate selected from a compound of any of the Formulae I-P1, I-P2, I-P4, or I-Lg, as defined herein, or a salt thereof.

In some embodiments, the present disclosure also provides a synthetic intermediate selected from Compounds 1-6, 1-7, 1-8, and 1-9, or a salt thereof.

Solutions Comprising Compound 1 and a Polymer

As discussed above, the methods of preparing solid dispersions herein typically include forming a solution of Compound 1 and the polymer in the solvent, e.g., for subsequent spray drying.

Suitable polymers are not particular limited and can be any of the polymers described herein as suitable for use as matrix polymers. For example, in some embodiments, the polymer can be a hydrophilic polymer, a hydrophobic polymer, an amphiphilic polymer, or any combinations thereof. In some embodiments, the polymer can be selected from cellulose esters and cellulose ethers, polyalkylene oxides, polyacrylates and polymethacrylates, homopolymers and copolymers of N-vinyl lactams, polyacrylamides, vinyl acetate polymers, graft copolymers of polyethylene glycol, polyvinyl caprolactam and polyvinyl acetate, polyvinyl acetate phthalate, oligo- and polysaccharides, and mixtures of two or more thereof. In some embodiments, the polymer can be any of those shown in [4]-[17] of the Summary section. In some particular embodiments, the polymer can be a copolymer of 2-dimethylaminoethyl methacrylate, butyl methacrylate, and methyl methacrylate, such as poly((2-dimethylaminoethyl)methacrylate, butyl methacrylate, methyl methacrylate) (2:1:1) (e.g., Eudragit®E100). In some particular embodiments, the polymer can be a graft copolymer of polyethylene glycol 6000, polyvinyl acetate and polyvinylcaprolactam, with a weight average molecular weight ($M_w$) of about 90,000 g/mol to about 140,000 g/mol, such as about 118,000 g/mol. In some embodiments, the polymer can be a graft copolymer of polyethylene glycol 6000, polyvinyl acetate and polyvinylcaprolactam, with a weight ratio of about 13:30:57, wherein the graft copolymer has a weight average molecular weight ($M_w$) of about 118,000 g/mol. In some embodiments, the polymer can be a graft copolymer of polyethylene glycol, polyvinyl acetate and polyvinylcaprolactam (e.g., Soluplus®). In some embodiments, the polymer can be hydroxypropyl cellulose, e.g., HPC-SSL. In some specific embodiments, the polymer can be selected from Kollidon VA64, Kollidon® 30, HPMCAS-MG, HPMCAS-HG, Poloxamer 188, Soluplus, HPMC E3 LV, hydroxypropylmethyl cellulose Phthalate (HPMCP), Eudragit®E100, and Hydroxypropyl cellulose HPC-SSL.

Various solvents are suitable to prepare the solution comprising Compound 1 and the polymer. For example, solvents suitable for spray drying can be any organic compound in which Compound 1 and the polymer are mutually soluble. Preferably, the solvent is also volatile with a boiling point of 150° C. or less. In addition, the solvent should preferably have relatively low toxicity and be removed from the dispersion to a level that is acceptable according to the International Committee on Harmonization (ICH) guidelines. Removal of solvent to this level may require a processing step such as tray-drying or agitated drying or any other secondary drying subsequent to the spray-drying process. Examples of solvents include alcohols such as methanol, ethanol, n-propanol, isopropanol, and butanol; ketones such as acetone, methyl ethyl ketone and methyl isobutyl ketone; esters such as ethyl acetate and propyl acetate; and various other solvents such as dichloromethane, acetonitrile, toluene, and 1,1,1-trichloroethane. Mixtures of solvents can also be used, as can mixtures with water as long as the polymer and Compound 1 are sufficiently soluble to make the spray-drying process practicable.

In some preferred embodiments, the solvent comprises acetone, dichloromethane ethanol, methanol, water or a mixture thereof. In some specific embodiments, the solvent can be a mixture of acetone and methanol. In some embodiments, the solvent can be a mixture of dichloromethane and methanol, such as in a volume ratio of dichloromethane to methanol ranging from about 1:1 to about 9:1, such as about 1:1 or about 9:1. In some embodiments, the solvent can be acetone. In some embodiments, the solvent can be methanol. In some embodiments, the solvent can be dichloromethane.

The solution can include Compound 1 in various concentrations. For example, in some embodiments, the solution can include Compound 1 at a concentration of about 5 mg/mL to about 150 mg/mL, such as about 10 mg/mL, about 20 mg/mL, about 50 mg/mL, about 100 mg/mL, about 150 mg/mL, or any range between the recited values. As detailed in the Example section, a solution having Compound 1 at a concentration as high as 50 mg/mL or 100 mg/mL can be successfully spray dried to provide desired solid dispersions.

Typically, the weight ratio of Compound 1 to the polymer in the solution ranges from about 1:50 to 10:1, such as about 1:20, about 1:10, about 1:4, about 1:2, about 2:3, about 1:1, about 3:2, about 10:1, or any range between the recited values. In some embodiments, the solution can comprise Compound 1 in an amount such that the solid dispersion prepared can have Compound 1 in an amount ranging from about 10-80% by weight, such as about 20%, about 30%, about 40%, about 50%, about 60%, about 70%, or any range between the recited values. In some embodiments, the solution can comprise the polymer in an amount ranging from about 20-90% by weight, such as about 20%, about 30%, about 40%, about 50%, about 60%, about 70%, or about 80%, about 90%, any range between the recited values. Typically, the solution can comprise Compound 1 in an amount of about 20-60% by weight and the polymer in an amount of about 40-80% by weight. In some embodiments, the solution can comprise Compound 1 in an amount of about 30-50% by weight and the polymer in an amount of about 50-70% by weight. It should be understood that unless otherwise specified or obviously contrary from context, the percentage weight referred to herein is based on dry weight. As such, when calculating the weight percentage of a solute, e.g., Compound 1 or polymer, in a solution, the solvent should not be considered.

In some exemplary embodiments, the solution herein comprises, consists essentially of, or consists of Compound 1 and a copolymer of 2-dimethylaminoethyl methacrylate, butyl methacrylate, and methyl methacrylate, such as poly ((2-dimethylaminoethyl)methacrylate, butyl methacrylate, methyl methacrylate) (2:1:1) (e.g., Eudragit®E100) in a solvent selected from acetone, dichloromethane, methanol, or any combination thereof, wherein Compound 1 is in a concentration of about 5 mg/mL to about 150 mg/mL (e.g., about 10 mg/mL, about 20 mg/mL, about 50 mg/mL, about 100 mg/mL, about 150 mg/mL, or any range between the recited values, such as about 10-50 or 10-100 mg/mL), and wherein the weight ratio of Compound 1 to the copolymer of 2-dimethylaminoethyl methacrylate, butyl methacrylate, and methyl methacrylate, such as poly((2-dimethylaminoethyl)methacrylate, butyl methacrylate, methyl methacrylate) (2:1:1) (e.g., Eudragit®E100) ranges from about 1:20 to about 5:1, such as about 1:10, about 1:4, about 1:2, about 2:3, about 1:1, about 3:2, about 2:1, about 5:1 or any range between the recited values, preferably, about 1:4 to about 2:1. In some embodiments, the solution comprises the Compound 1 in an amount such that the solid dispersion prepared can have Compound 1 in an amount of about 10% to about 80% by weight, such as about 20%, about 30%, about 40%, about 50%, about 60%, about 70%, or any range between the recited values, preferably about 20-60% by weight or about 35-45% by weight. In some embodiments, the solution comprises the Compound 1 in an amount such that the solid dispersion prepared can have about 30-50% by weight of Compound 1 and about 50-70% by weight of the copolymer of 2-dimethylaminoethyl methacrylate, butyl methacrylate, and methyl methacrylate, such as poly((2-dimethylaminoethyl)methacrylate, butyl methacrylate, methyl methacrylate) (2:1:1) (e.g., Eudragit®E100). In some embodiments, the solvent can be a mixture of acetone and methanol. In some embodiments, the solvent can be a mixture of dichloromethane and methanol, such as in a volume ratio of dichloromethane to methanol ranging from about 1:1 to about 9:1, such as about 1:1 or about 9:1. In some embodiments, the solvent can be acetone. In some embodiments, the solvent can be methanol. In some embodiments, the solvent can be dichloromethane.

In some exemplary embodiments, the solution herein comprises, consists essentially of, or consists of Compound 1 and a graft copolymer of polyethylene glycol, polyvinyl acetate and polyvinylcaprolactam (e.g., Soluplus®) in a solvent selected from acetone, dichloromethane, methanol, or any combination thereof, wherein Compound 1 is in a concentration of about 5 mg/mL to about 150 mg/mL (e.g., about 10 mg/mL, about 20 mg/mL, about 50 mg/mL, about 100 mg/mL, about 150 mg/mL, or any range between the recited values, such as about 10-50 or 10-100 mg/mL), and wherein the weight ratio of Compound 1 to the graft copolymer of polyethylene glycol, polyvinyl acetate and polyvinylcaprolactam (e.g., Soluplus®) ranges from about 1:20 to about 5:1, such as about 1:10, about 1:4, about 1:2, about 2:3, about 1:1, about 3:2, about 2:1, about 5:1 or any range between the recited values, preferably, about 1:4 to about 2:1. In some embodiments, the solution comprises the Compound 1 in an amount such that the solid dispersion prepared can have Compound 1 in an amount of about 10% to about 80% by weight, such as about 20%, about 30%, about 40%, about 50%, about 60%, about 70%, or any range between the recited values, preferably about 20-60% by weight or about 35-45% by weight. In some embodiments, the solution comprises the Compound 1 in an amount such that the solid dispersion prepared can have about 30-50% by weight of Compound 1 and about 50-70% by weight of the graft copolymer of polyethylene glycol, polyvinyl acetate and polyvinylcaprolactam (e.g., Soluplus®). In some embodiments, the solvent can be a mixture of acetone and methanol. In some embodiments, the solvent can be a mixture of dichloromethane and methanol, such as in a volume ratio of dichloromethane to methanol ranging from about 1:1 to about 9:1, such as about 1:1 or about 9:1. In some embodiments, the solvent can be acetone. In some embodiments, the solvent can be methanol. In some embodiments, the solvent can be dichloromethane.

In some exemplary embodiments, the solution herein comprises, consists essentially of, or consists of Compound 1 and HPMC (e.g., HPMC E3 LV) in a solvent selected from acetone, dichloromethane, methanol, or any combination thereof, wherein Compound 1 is in a concentration of about 5 mg/mL to about 100 mg/mL (e.g., about 10 mg/mL, about 20 mg/mL, about 50 mg/mL, about 100 mg/mL, or any range between the recited values, such as about 10-50 mg/mL), and wherein the weight ratio of Compound 1 to HPMC (e.g., HPMC E3 LV) ranges from about 1:20 to about 5:1, such as about 1:10, about 1:4, about 1:2, about 2:3, about 1:1, about 3:2, about 2:1, about 5:1 or any range between the recited values, preferably, about 1:4 to about 2:1. In some embodiments, the solution comprises the Compound 1 in an amount such that the solid dispersion prepared can have Compound 1 in an amount of about 10% to about 80% by weight, such as about 20%, about 30%, about 40%, about 50%, about 60%, about 70%, or any range between the recited values, preferably about 20-60% by weight or about 35-45% by weight. In some embodiments, the solution comprises the Compound 1 in an amount such that the solid dispersion prepared can have about 30-50% by weight of Compound 1 and about 50-70% by weight of HPMC (e.g., HPMC E3 LV). In some embodiments, the solvent can be a mixture of acetone and methanol. In some embodiments, the solvent can be a mixture of dichloromethane and methanol, such as in a volume ratio of dichloromethane to methanol ranging from about 1:1 to about 9:1, such as about 1:1 or about 9:1. In some embodiments, the solvent can be acetone. In some embodiments, the solvent can be methanol. In some embodiments, the solvent can be dichloromethane.

In some exemplary embodiments, the solution herein comprises, consists essentially of, or consists of Compound 1 and hydroxypropyl cellulose (e.g., HPC-SSL) in a solvent selected from acetone, dichloromethane, methanol, or any combination thereof, wherein Compound 1 is in a concentration of about 5 mg/mL to about 100 mg/mL (e.g., about 10 mg/mL, about 20 mg/mL, about 50 mg/mL, about 100 mg/mL, or any range between the recited values, such as about 10-50 mg/mL), and wherein the weight ratio of Compound 1 to hydroxypropyl cellulose (e.g., HPC-SSL) ranges from about 1:20 to about 5:1, such as about 1:10, about 1:4, about 1:2, about 2:3, about 1:1, about 3:2, about 2:1, about 5:1 or any range between the recited values, preferably, about 1:4 to about 2:1. In some embodiments, the solution comprises the Compound 1 in an amount such that the solid dispersion prepared can have Compound 1 in an amount of about 10% to about 80% by weight, such as about 20%, about 30%, about 40%, about 50%, about 60%, about 70%, or any range between the recited values, preferably about 20-60% by weight or about 35-45% by weight. In some embodiments, the solution comprises the Compound 1 in an amount such that the solid dispersion prepared can have about 30-50% by weight of Compound 1 and about 50-70% by weight of hydroxypropyl cellulose (such as HPC-SSL). In some embodiments, the solvent can be a mixture of acetone and methanol. In some embodiments, the solvent can be a mixture of dichloromethane and methanol, such as in a volume ratio of dichloromethane to methanol ranging from about 1:1 to about 9:1, such as about 1:1 or about 9:1. In some embodiments, the solvent can be acetone. In some embodiments, the solvent can be methanol. In some embodiments, the solvent can be dichloromethane.

It should be noted that the solution comprising Compound 1 and the polymer are also novel compositions of the present disclosure. For example, any of the solutions prepared herein in the Examples section before the spray drying step are novel compositions of the present disclosure.

Spray Drying

The methods of preparing solid dispersions herein typically include spray drying the solution comprising Compound 1 and the polymer as described herein. In the spray-drying process, the solvent of the solution comprising Compound 1 and the polymers is rapidly removed by evaporation in the spray-drying apparatus, resulting in the formation of a homogeneous or substantially homogeneous solid dispersion, typically amorphous solid dispersion. In such homogeneous or substantially homogeneous dispersions, Compound 1 is dispersed as homogeneously as possible throughout the polymer and can be thought of as a solid solution of Compound 1 dispersed in the polymer.

The term spray drying is used conventionally and broadly refers to processes involving breaking up liquid mixtures into small droplets (atomization) and rapidly removing solvent from the mixture in a spray-drying apparatus where there is a strong driving force for evaporation of solvent from the droplets. Such a strong driving force for solvent evaporation is generally provided by maintaining the partial pressure of solvent in the spray-drying apparatus well below the vapor pressure of the solvent at the temperature of the drying droplets. This is accomplished for example by either (1) maintaining the pressure in the spray-drying apparatus at a partial vacuum (e.g., 0.01 to 0.50 atm); (2) mixing the liquid droplets with a warm drying gas; or (3) both (1) and (2). In addition, in some cases, at least a portion of the heat required for evaporation of solvent may be provided by heating the spray solution.

Spray drying processes suitable for preparing the solid dispersions herein are not particularly limited. In a typical spray drying process, the solution comprising Compound 1 and the polymer is atomized through a pressure nozzle or a two-fluid nozzle. Generally, an appropriately sized and designed nozzle is one that will produce droplets within a desired size range when the spray solution is pumped through the nozzle at the desired rate.

As described in the Examples section, in some embodiments, the solvent was evaporated using a BUCHI B290 Spray Dryer with the following operating parameters: 0.7 mm nozzle; Aspirator, 100%; Pump, 40-50%; Q-flow, 40-50 mm. The inlet temperature was set according to the solvent system and an outlet temperature is maintained between about 50-60° C.

In some embodiments, the spray-drying process can be performed under the following operating parameters: 0.7 mm nozzle; Aspirator, 100%; Pump, 40-50%; Q-flow, 40-50 mm, inlet temperature, about 86-90° C., outlet temperature, about 52-57 or 50-58° C.

In some embodiments, the spray-drying process can be performed under the following operating parameters: nozzle size, 1.0 mm; nozzle type, Two-fluid nozzle; circulation gas flow, 100 kg/h; inlet temperature, 95.0-105.0° C.; outlet temperature, 50.0-60.0° C.; atomization gas flow rate, 70-90 NL/min; B1R62 atomization pressure, 3.0±0.5 bar; B1P62 gun atomization pressure, 1.2±0.2 bar, condenser outlet temperature, −5 (−10-0)° C., e.g., using GEA PSD-1 spray drier. In some embodiments, the spray rate can be about 80-100 g/min.

In some embodiments, the spray-drying process can be performed under the following operating parameters using solvent system of dichloromethane and methanol at a volume ratio of 1:1: nozzle size, 2.0 mm; nozzle type, Two-fluid nozzle; circulation gas flow, 500 kg/h; inlet temperature, 100.0-110.0° C.; outlet temperature, 50.0-60.0° C.; atomization gas flow rate, 50.0-70.0 kg/h; atomization pressure, 345±5.0 KPa; condenser outlet temperature, −23 (−25-0)° C., e.g., using GEA PSD-3 spray drier. In some embodiments, the spray rate can be about 20-30 kg/h.

In some embodiments, the spray-drying process can be performed under the following operating parameters using solvent system of dichloromethane and methanol at a volume ratio of 9:1 (dichloromethane to methanol): nozzle size, 74/17; nozzle type, pressure nozzle; circulation gas flow, 500 kg/h; inlet temperature, 75.0-90.0° C.; outlet temperature, 35.0-50.0° C.; nozzle pressure, 3.0-7.0 MPa; condenser outlet temperature, −23 (−25-0)° C., e.g., using GEA PSD-3 spray drier. In some embodiments, the spray rate can be about 30-45 kg/h.

In certain embodiments, the spray dried powder can be further processed through a secondary drying step. The secondary drying is performed for a sufficient period of time to meet product specifications. For example, in some embodiments, secondary drying occurs at about 30° C., 35° C., 40° C., 45° C., or 50° C. In certain embodiments, the drying time is at least about 1, 2, 3, 5, 6, 7, 8, 9, or 10 hours. In certain embodiments, the drying time is about 6 hours. In some embodiments, the secondary drying is performed under vacuum, for example at a pressure of about −80 kPa or below.

The solid dispersions produced by any of the methods described herein are novel compositions of the present disclosure. For example, in some embodiments, the present disclosure provides a solid dispersion prepared according to any of the methods described in the Examples section herein. In some embodiments, the present disclosure provides a spray dried solid dispersion shown in the Examples section, SDD-1 to SDD-20, SDD-10A, SDD-13A, and SDD-19A.

In some exemplary embodiments, the present disclosure provides a solid dispersion, which is obtained by a process comprising spray drying a solution comprising, consisting essentially of, or consisting of Compound 1 and a copolymer of 2-dimethylaminoethyl methacrylate, butyl methacrylate, and methyl methacrylate, such as poly((2-dimethylaminoethyl)methacrylate, butyl methacrylate, methyl methacrylate) (2:1:1) (e.g., Eudragit®E100) in a solvent selected from acetone, dichloromethane, methanol, or any combination thereof, wherein Compound 1 is in a concentration of about 5 mg/mL to about 150 mg/mL (e.g., about 10 mg/mL, about 20 mg/mL, about 50 mg/mL, about 100 mg/mL, about 150 mg/mL, or any range between the recited values, such as about 10-50 or 10-100 mg/mL), and wherein the weight ratio of Compound 1 to the copolymer of 2-dimethylaminoethyl methacrylate, butyl methacrylate, and methyl methacrylate, such as poly((2-dimethylaminoethyl)methacrylate, butyl methacrylate, methyl methacrylate) (2:1:1) (e.g., Eudragit®E100) ranges from about 1:20 to about 5:1, such as about 1:10, about 1:4, about 1:2, about 2:3, about 1:1, about 3:2, about 2:1, about 5:1 or any range between the recited values, preferably, about 1:4 to about 2:1. In some embodiments, the solution comprises the Compound 1 in an amount such that the solid dispersion prepared can have Compound 1 in an amount of about 10% to about 80% by weight, such as about 20%, about 30%, about 40%, about 50%, about 60%, about 70%, or any range between the recited values, preferably about 20-60% by weight or about 35-45% by weight. In some embodiments, the solution comprises the Compound 1 in an amount such that the solid dispersion prepared can have about 30-50% by weight of Compound 1 and about 50-70% by weight of the copolymer of 2-dimethylaminoethyl methacrylate, butyl methacrylate, and methyl methacrylate, such as poly((2-dimethylaminoethyl)methacrylate, butyl methacrylate, methyl methacrylate) (2:1:1) (e.g., Eudragit®E100). In some embodiments, the solvent can be a mixture of acetone and methanol. In some embodiments, the solvent can be a mixture of dichloromethane and methanol, such as in a volume ratio of dichloromethane to methanol ranging from about 1:1 to about 9:1, such as about 1:1 or about 9:1. In some embodiments, the solvent can be acetone. In some embodiments, the solvent can be methanol. In some embodiments, the solvent can be dichloromethane. In some embodiments, the solid dispersion can be characterized by having one or more (e.g., two or more) of the following characteristics: 1) being an amorphous solid, 2) having a drug load of about 36.0% to about 44.0%, and 3) having an impurity level of 0.29% by weight or less for the impurity having a relative retention time to Compound 1 (RRT) at 1.03; an impurity level of 0.34% by weight or less for the impurity having a RRT at 1.15; an impurity level of 0.21% by weight or less for the impurity having a RRT at 1.66; an impurity level of 0.15% by weight or less for unspecified impurity; and a total impurity of less than 2.0% by weight. In some embodiments, the solid dispersion conforms to the specification shown in Table 17.

In some exemplary embodiments, the present disclosure provides a solid dispersion, which is obtained by a process comprising spray drying a solution comprising, consisting essentially of, or consisting of Compound 1 and a graft copolymer of polyethylene glycol, polyvinyl acetate and polyvinylcaprolactam (e.g., Soluplus®) in a solvent selected from acetone, dichloromethane, methanol, or any combination thereof, wherein Compound 1 is in a concentration of about 5 mg/mL to about 100 mg/mL (e.g., about 10 mg/mL, about 20 mg/mL, about 50 mg/mL, about 100 mg/mL, or any range between the recited values, such as about 10-50 mg/mL), and wherein the weight ratio of Compound 1 to the graft copolymer of polyethylene glycol, polyvinyl acetate and polyvinylcaprolactam (e.g., Soluplus®) ranges from about 1:20 to about 5:1, such as about 1:10, about 1:4, about 1:2, about 2:3, about 1:1, about 3:2, about 2:1, about 5:1 or any range between the recited values, preferably, about 1:4 to about 2:1. In some embodiments, the solution comprises the Compound 1 in an amount such that the solid dispersion prepared can have Compound 1 in an amount of about 10% to about 80% by weight, such as about 20%, about 30%, about 40%, about 50%, about 60%, about 70%, or any range between the recited values, preferably about 20-60% by weight or about 35-45% by weight. In some embodiments, the solution comprises the Compound 1 in an amount such that the solid dispersion prepared can have about 30-50% by weight of Compound 1 and about 50-70% by weight of the graft copolymer of polyethylene glycol, polyvinyl acetate and polyvinylcaprolactam (e.g., Soluplus®). In some specific embodiments, the solvent can be a mixture of acetone and methanol. In some embodiments, the solvent can be a mixture of dichloromethane and methanol, such as in a volume ratio of dichloromethane to methanol ranging from about 1:1 to about 9:1, such as about 1:1 or about 9:1. In some embodiments, the solvent can be acetone. In some embodiments, the solvent can be methanol. In some embodiments, the solvent can be dichloromethane.

In some exemplary embodiments, the present disclosure provides a solid dispersion, which is obtained by a process comprising spray drying a solution comprising, consisting essentially of, or consisting of Compound 1 and HPMC (e.g. HPMC E3 LV) in a solvent selected from acetone, dichloromethane, methanol, or any combination thereof, wherein Compound 1 is in a concentration of about 5 mg/mL to about 100 mg/mL (e.g., about 10 mg/mL, about 20 mg/mL, about 50 mg/mL, about 100 mg/mL, or any range between the recited values, such as about 10-50 mg/mL), and wherein the weight ratio of Compound 1 to HPMC (e.g., HPMC E3 LV) ranges from about 1:20 to about 5:1, such as about 1:10, about 1:4, about 1:2, about 2:3, about 1:1, about 3:2, about 2:1, about 5:1 or any range between the recited values, preferably, about 1:4 to about 2:1. In some embodiments, the solution comprises the Compound 1 in an amount such that the solid dispersion prepared can have Compound 1 in an amount of about 10% to about 80% by weight, such as about 20%, about 30%, about 40%, about 50%, about 60%, about 70%, or any range between the recited values, preferably about 20-60% by weight or about 35-45% by weight. In some embodiments, the solution comprises the Compound 1 in an amount such that the solid dispersion prepared can have about 30-50% by weight of Compound 1 and about 50-70% by weight of HPMC (e.g., HPMC E3 LV). In some embodiments, the solvent can be a mixture of acetone and methanol. In some embodiments, the solvent can be a mixture of dichloromethane and methanol, such as in a volume ratio of dichloromethane to methanol ranging from about 1:1 to about 9:1, such as about 1:1 or about 9:1. In some embodiments, the solvent can be acetone. In some embodiments, the solvent can be methanol. In some embodiments, the solvent can be dichloromethane.

In some exemplary embodiments, the present disclosure provides a solid dispersion, which is obtained by a process comprising spray drying a solution comprising, consisting essentially of, or consisting of Compound 1 and hydroxypropyl cellulose (such as HPC-SSL) in a solvent selected from acetone, dichloromethane, methanol, or any combination thereof, wherein Compound 1 is in a concentration of about 5 mg/mL to about 100 mg/mL (e.g., about 10 mg/mL, about 20 mg/mL, about 50 mg/mL, about 100 mg/mL, or any range between the recited values, such as about 10-50 mg/mL), and wherein the weight ratio of Compound 1 to hydroxypropyl cellulose (such as HPC-SSL) ranges from about 1:20 to about 5:1, such as about 1:10, about 1:4, about 1:2, about 2:3, about 1:1, about 3:2, about 2:1, about 5:1 or any range between the recited values, preferably, about 1:4 to about 2:1. In some embodiments, the solution comprises the Compound 1 in an amount such that the solid dispersion prepared can have Compound 1 in an amount of about 10% to about 80% by weight, such as about 20%, about 30%, about 40%, about 50%, about 60%, about 70%, or any range between the recited values, preferably about 20-60% by weight or about 35-45% by weight. In some embodiments, the solution comprises the Compound 1 in an amount such that the solid dispersion prepared can have about 30-50% by weight of Compound 1 and about 50-70% by weight of hydroxypropyl cellulose (e.g., HPC-SSL). In some embodiments, the solvent can be a mixture of acetone and methanol. In some embodiments, the solvent can be a mixture of dichloromethane and methanol, such as in a volume ratio of dichloromethane to methanol ranging from about 1:1 to about 9:1, such as about 1:1 or about 9:1. In some embodiments, the solvent can be acetone. In some embodiments, the solvent can be methanol. In some embodiments, the solvent can be dichloromethane.

Typically, the solid dispersion prepared by the process herein can be characterized as an amorphous solid dispersion. In some embodiments, the solid dispersion prepared by the process herein (e.g., through spray drying) is essentially free of Compound 1 in a crystalline form. In some embodiments, the solid dispersion prepared by the process herein (e.g., through spray drying) does not include Compound 1 in a crystalline form in an amount detectable by XRPD. In some embodiments, the solid dispersion prepared by the process herein (e.g., through spray drying) is storage stable, for example, the solid dispersion is characterized in that, upon storage at 2-8° C., 25° C. and 60% relative humidity, or 40° C. and 75% relative humidity for one week or longer, such as up to 6 months or longer, the solid dispersion does not have Compound 1 in a crystalline form in an amount detectable by XRPD.

Pharmaceutical Compositions

In various embodiments, the present disclosure also provides pharmaceutical compositions comprising Compound 1 and optionally a pharmaceutically acceptable excipient. Typically, the pharmaceutical composition comprises Compound 1 in a solid dispersion described herein. However, in some embodiments, the pharmaceutical composition can also comprise the starting Compound 1 as described herein, e.g., an amorphous form of Compound 1, such as a spray dried amorphous Compound 1 (e.g., SDD-0 or SDD-0A). Non-limiting suitable excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. See also Remington's The Science and Practice of Pharmacy, 21st Edition, A. R. Gennaro (Lippincott, Williams & Wilkins, Baltimore, Md., 2005; incorporated herein by reference), which discloses various excipients used in formulating pharmaceutical compositions and known techniques for the preparation thereof.

In some embodiments, the present disclosure provides a pharmaceutical composition comprising a solid dispersion of the present disclosure (e.g., any of those described herein, such as any of those described in [1]-[19] and [25]-[28] of the Summary section), such as an amorphous solid dispersion or a stable amorphous solid dispersion as described herein. Typically, the pharmaceutical composition comprises the solid dispersion in an amount ranging from about 10-90% by weight, such as about 20%, about 30%, about 40%, about 50%, about 60%, about 70%, about 80%, or any range between the recited values. In some embodiments, the pharmaceutical composition comprises the solid dispersion in an amount ranging from about 50-70% by weight, such as about 50%, about 60%, about 70%, or any range between the recited values. In some embodiments, the pharmaceutical composition can have the ingredients (and relative amounts) the same or substantially the same as those shown in any of Tables 18, 21, 22A, and 22B herein. Typically, the pharmaceutical composition comprising Compound 1 in amorphous form. In some embodiments, the pharmaceutical composition is essentially free of Compound 1 in a crystalline form. In some embodiments, the pharmaceutical composition does not include Compound 1 in a crystalline form in an amount detectable by XRPD. The pharmaceutical composition herein is typically storage stable. In some embodiments, the pharmaceutical composition herein can be characterized in that, upon storage at 2-8° C., 25° C. and 60% relative humidity, or 40° C. and 75% relative humidity for one week or longer, such as up to 6 months or longer, the pharmaceutical composition does not have Compound 1 in a crystalline form in an amount detectable by XRPD. Typically, a storage stable pharmaceutical composition herein can also be characterized as having no significant changes in terms of the amount of related substance of Compound 1 and/or the assay amount of Compound 1, after being stored at 25° C. and 60% relative humidity or 40° C. and 75% relative humidity for one week or longer, such as up to 6 months or longer.

In some embodiments, the solid dispersion such as amorphous solid dispersion of the present disclosure can be combined with one or more optional excipients to formulate the dispersion into suitable dosage formulations, such as tablets, capsules (e.g., hard gelatin capsules), strips, caplets, suspensions, powders for suspensions, cream, transdermal patches, depots, and the like.

Generally, excipients such as fillers, matrix materials, complexing agents, solubilizers, lubricants, glidants, antioxidants, and so forth may be used for customary purposes and in typical amounts without adversely affecting the properties of the compositions. See for example, Remington's The Science and Practice of Pharmacy, 21st Edition, A. R. Gennaro (Lippincott, Williams & Wilkins, Baltimore, Md., 2005; incorporated herein by reference).

In some embodiments, the pharmaceutical composition herein can comprise the solid dispersion such as amorphous solid dispersion described herein, and one or more additional pharmaceutical excipients selected from a diluent (e.g., microcrystalline cellulose, lactose, mannitol, etc.), a disintegrant (e.g., croscarmellose sodium, crospovidone, pregelatinized starch, etc.), a glidant (e.g., colloidal silica dioxide), a lubricant (e.g., sodium stearyl fumarate, magnesium stearate, hydrogenated castor oil, etc.), a surfactant (e.g., sodium lauryl sulfate, poloxamers, etc.), and a coating material.

Typically, the pharmaceutical composition can comprise a diluent such as microcrystalline cellulose, lactose, and/or mannitol.

Typically, the pharmaceutical composition can also comprise a disintegrant such as croscarmellose sodium, crospovidone, and/or pregelatinized starch.

A glidant such as colloidal silica dioxide can also be typically included in the pharmaceutical composition.

The pharmaceutical composition also generally includes a lubricant, such as sodium stearyl fumarate, magnesium stearate, and/or hydrogenated castor oil. In some embodiments, the pharmaceutical composition can comprise sodium stearyl fumarate.

The pharmaceutical composition can optionally include a surfactant. When included, the surfactant can be for example selected from sodium lauryl sulfate, poloxamers, and the alike.

The pharmaceutical composition can also be optionally coated, such as a film coat, e.g., Opadry® Complete Film Coating.

Typically, the pharmaceutical composition comprises Compound 1 in an effective amount. In certain embodiments, the effective amount is a therapeutically effective amount (e.g., amount effective for treating a cancer comprising a G12C mutation of KRAS, HRAS and/or NRAS, e.g., a KRAS G12C mutation, in a subject in need thereof). As used herein, a therapeutically effective amount of a compound of the present disclosure is an amount effective to treat a disease or disorder as described herein, which can depend on the recipient of the treatment, the disease or disorder being treated and the severity thereof, the composition containing the compound, the time of administration, the route of administration, the duration of treatment, the compound potency (e.g., for inhibiting KRAS G12C), its rate of clearance and whether or not another drug is co-administered.

Pharmaceutical compositions described herein can be prepared by any method known in the art of pharmacology. In general, such preparatory methods include bringing Compound 1 (e.g., the solid dispersion described herein) into association with a carrier or excipient, and/or one or more other accessory ingredients, and then, if necessary and/or desirable, shaping, and/or packaging the product into a desired single- or multi-dose unit. For example, in some embodiments, the present disclosure provides a method of preparing a pharmaceutical composition, which comprises mixing the solid dispersion described herein (e.g., any of those described in [1]-[19] and [25]-[28] of the Summary section herein) with a pharmaceutical excipient (e.g., described herein). In some embodiments, the pharmaceutical excipient comprises one or more excipients selected from a diluent (e.g., microcrystalline cellulose, lactose, mannitol, etc.), a disintegrant (e.g., croscarmellose sodium, crospovidone, pregelatinized starch, etc.), a glidant (e.g., colloidal silica dioxide), a lubricant (e.g., sodium stearyl fumarate, magnesium stearate, hydrogenated castor oil, etc.), a surfactant (e.g., sodium lauryl sulfate, poloxamers, etc.), and a coating material. The relative amounts of the solid dispersion and the pharmaceutical excipients include any of those described herein. Typically, the process used in the methods of preparing the pharmaceutical composition herein is selected such that it does not significantly affect the solid state of Compound 1. For example, typically, the process does not convert an amorphous form of Compound 1, e.g., in a solid dispersion herein, into a crystalline form in an amount detectable by XRPD.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient.

Relative amounts of Compound 1, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) Compound 1.

The pharmaceutical composition can be formulated for any routes of administration, for example, oral administration. Typically, the pharmaceutical composition is a solid dosage form. However, in some embodiments, other dosage forms such as liquid, suspension, or semi-solid dosage forms can also be used.

In some embodiments, the pharmaceutical composition comprising the solid dispersion herein is an oral dosage form, in particular, an oral solid dosage form. Solid dosage forms for oral administration include for example capsules, tablets, pills, powders, and granules. In such oral dosage forms, such as oral solid dosage forms, the solid dispersion of the present disclosure (e.g., any of those described herein, such as any of those described in [1]-[19] and [25]-[28] of the Summary section) can be mixed with a pharmaceutically acceptable excipient, such as one or more excipients selected from a diluent (e.g., microcrystalline cellulose, lactose, mannitol, etc.), a disintegrant (e.g., croscarmellose sodium, crospovidone, pregelatinized starch, etc.), a glidant (e.g., colloidal silica dioxide), a lubricant (e.g., sodium stearyl fumarate, magnesium stearate, hydrogenated castor oil, etc.), a surfactant (e.g., sodium lauryl sulfate, poloxamers, etc.), and a coating material. Methods for preparing such solid dosage forms are known in the art. For example, as exemplified herein in the Example section, a tablet formulation can be prepared by a process that includes roller compaction and tablet compression. A capsule formulation can be prepared by a process that includes direct mixing the solid dispersion with other pharmaceutically acceptable excipients followed by encapsulation. In some embodiments, a capsule formulation can also be prepared from a process that includes roller compaction a mixture of the solid dispersion with other pharmaceutically acceptable excipients to generate roller compaction granules, which is followed by encapsulation. Typically, a wet granulation is not used for preparing granules from the solid dispersion herein. The solid dosage forms such as tablets or capsules can typically comprise the solid dispersion in an amount ranging from about 10-90% by weight, such as about 20%, about 30%, about 40%, about 50%, about 60%, about 70%, or any range between the recited values. In some embodiments, the solid dosage forms such as tablets or capsules can comprise the solid dispersion in an amount ranging from about 50-70% by weight, such as about 50%, about 60%, about 70%, or any range between the recited values. In some embodiments, the solid dosage forms such as tablets or capsules can have the ingredients (and relative amounts) the same or substantially the same as those shown in any of Tables 18, 21, 22A, and 22B herein. Typically, the solid dosage forms such as tablets or capsules can comprise comprising Compound 1 in amorphous form. In some embodiments, the solid dosage forms such as tablets or capsules can be essentially free of Compound 1 in a crystalline form. In some embodiments, the solid dosage forms such as tablets or capsules do not include Compound 1 in a crystalline form in an amount detectable by)(RFD. The solid dosage forms herein are typically storage stable. In some embodiments, the solid dosage forms can be characterized in that, upon storage at 2-8° C., 25° C. and 60% relative humidity, or 40° C. and 75% relative humidity for one week or longer, such as up to 6 months or longer, the pharmaceutical composition does not have Compound 1 in a crystalline form in an amount detectable by XRPD.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Although the descriptions of pharmaceutical compositions provided herein are mainly directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. For veterinary use, Compound 1 can be administered as a suitably acceptable formulation in accordance with normal veterinary practice. The veterinarian can readily determine the dosing regimen and route of administration that is most appropriate for a particular animal.

Compound 1, such as in the solid dispersion described herein, is typically formulated in unit dosage form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of Compound 1; the specific composition employed; the age, body weight, general health, sex, and diet of the subject; the time of administration, route of administration, and rate of excretion of Compound 1; the duration of the treatment; drugs used in combination or coincidental with Compound 1; and like factors known in the medical arts.

In some embodiments, all the necessary components for the treatment of KRAS-related disorder using Compound 1 either alone or in combination with another agent or intervention traditionally used for the treatment of such disease can be packaged into a kit. Specifically, in some embodiments, the present invention provides a kit for use in the therapeutic intervention of the disease comprising a packaged set of medicaments that include Compound 1 as well as other components for preparing deliverable forms of said medicaments, and/or devices for delivering such medicaments, and/or any agents that are used in combination therapy with Compound 1, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet.

Methods of Treatment

Compound 1, solid dispersions of Compound 1 and pharmaceutical compositions described herein are useful in treating and/or preventing diseases or disorders that are associated with RAS, e.g., KRAS G12C.

In some embodiments, the present disclosure provides a method of inhibiting RAS-mediated cell signaling comprising contacting a cell with an effective amount of Compound 1. Inhibition of RAS-mediated signal transduction can be assessed and demonstrated by a wide variety of ways known in the art. Non-limiting examples include a showing of (a) a decrease in GTPase activity of RAS; (b) a decrease in GTP binding affinity or an increase in GDP binding affinity; (c) an increase in $K_{off}$ of GTP or a decrease in $K_{off}$ of GDP; (d) a decrease in the levels of signaling transduction molecules downstream in the RAS pathway, such as a decrease in pMEK, pERK, or pAKT levels; and/or (e) a decrease in binding of RAS complex to downstream signaling molecules including but not limited to Raf. Kits and commercially available assays can be utilized for determining one or more of the above.

In some embodiments, the present disclosure provides a method of inhibiting KRAS, HRAS, and/or NRAS G12C in a cell, the method comprising contacting the cell with an effective amount of Compound 1.

In some embodiments, the present disclosure provides a method of treating a disease or disorder, e.g., a cancer associated with G12C mutation of KRAS, HRAS and/or NRAS, such as a cancer associated with KRAS G12C, in a subject in need thereof. In some embodiments, the method comprises administering to the subject a therapeutically effective amount of Compound 1 or solid dispersion herein (e.g., any of those described in [1]-[19] and [25]-[28] in the Summary section), or a pharmaceutical composition herein (e.g., any of those described in [29]-[35] and [40]-[44] in the Summary section).

In some embodiments, a method for treatment of cancer is provided, the method comprising administering to a subject in need thereof an effective amount of Compound 1 or solid dispersion herein (e.g., any of those described in [1]-[19] and [25]-[28] in the Summary section), or a pharmaceutical composition herein (e.g., any of those described in [29]-[35] and [40]-[44] in the Summary section). In some embodiments, the cancer comprises a G12C mutation of KRAS, HRAS and/or NRAS, e.g., a KRAS G12C mutation. Determining whether a tumor or cancer comprises a G12C mutation of KRAS, HRAS and/or NRAS is known in the art, for example, as described in US2018/0334454. In various embodiments, the cancer can be pancreatic cancer, endometrial cancer, colorectal cancer or lung cancer (e.g., non-small cell lung cancer). In some embodiments, the cancer is a hematological cancer (e.g., described herein). In some embodiments, the cancer is MYH associated polyposis. In some embodiments, the cancer is gall bladder cancer, thyroid cancer, or bile duct cancer. Non-limiting examples of cancer also include acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplasia syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer.

In some embodiments the present disclosure provides a method of treating a disease or disorder (e.g., a cancer described herein) in a subject in need thereof, wherein the method comprises determining if the subject has a G12C mutation of KRAS, HRAS and/or NRAS, e.g., KRAS G12C mutation, and if the subject is determined to have the KRAS, HRAS and/or NRAS G12C mutation, e.g., KRAS G12C mutation, then administering to the subject a therapeutically effective dose of Compound 1 or solid dispersion herein (e.g., any of those described in [1]-[19] and [25]-[28] in the Summary section), or a pharmaceutical composition herein (e.g., any of those described in [29]-[35] and [40]-[44] in the Summary section).

G12C mutation of KRAS, HRAS and/or NRAS has also been identified in hematological malignancies (e.g., cancers that affect blood, bone marrow and/or lymph nodes). Accordingly, certain embodiments are directed to a method of treating hematological malignancy in a subject in need thereof, the method typically comprises administration of a compound of the present disclosure (e.g., in the form of a pharmaceutical composition) to the subject. Such malignancies include, but are not limited to leukemias and lymphomas, such as Acute lymphoblastic leukemia (ALL), Acute myelogenous leukemia (AML), Chronic lymphocytic leukemia (CLL), small lymphocytic lymphoma (SLL), Chronic myelogenous leukemia (CIVIL), Acute monocytic leukemia (AMoL) and/or other leukemias. In some embodiments, the hematological malignancy can also include lymphomas such as Hodgkins lymphoma or non-Hodgkins lymphoma, plasma cell malignancies such as multiple myeloma, mantle cell lymphoma, and Waldenstrom's macroglubunemia.

Compound 1 can be used as a monotherapy or in a combination therapy. In some embodiments, the combination therapy includes treating the subject with a chemotherapeutic agent, therapeutic antibody, radiation, cell therapy, or immunotherapy. In some embodiments, compounds of the present disclosure can also be co-administered with an additional pharmaceutically active compound, either concurrently or sequentially in any order, to a subject in need thereof (e.g., a subject having a cancer associated with KRAS G12C mutation as described herein). In some embodiments, the additional pharmaceutically active compound can be a chemotherapeutic agent, a therapeutic antibody, etc. Any of the known chemotherapeutics can be used in combination with the compounds of the present disclosure. In some embodiments, compounds of the present disclosure can also be used in combination with a radiation therapy, hormone therapy, cell therapy, surgery and immunotherapy, which therapies are well known to those skilled in the art.

The administering herein is not limited to any particular route of administration. For example, in some embodiments, the administering can be orally, nasally, transdermally, pulmonary, inhalationally, buccally, sublingually, intraperintoneally, subcutaneously, intramuscularly, intravenously, rectally, intrapleurally, intrathecally or parenterally. In some embodiments, the administering is orally.

Dosing regimen including doses can vary and can be adjusted, which can depend on various factors known in the medical arts.

Definitions

As used herein, the singular form "a", "an", and "the", includes plural references unless it is expressly stated or is unambiguously clear from the context that such is not intended.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Headings and subheadings are used for convenience and/or formal compliance only, do not limit the subject technology, and are not referred to in connection with the interpretation of the description of the subject technology. Features described under one heading or one subheading of the subject disclosure may be combined, in various embodiments, with features described under other headings or subheadings. Further it is not necessarily the case that all features under a single heading or a single subheading are used together in embodiments.

As used herein, the term "about" modifying an amount related to the invention refers to variation in the numerical quantity that can occur, for example, through routine testing and handling; through inadvertent error in such testing and handling; through differences in the manufacture, source, or purity of ingredients employed in the invention; and the like. As used herein, "about" a specific value also includes the specific value, for example, about 10% includes 10%. Whether or not modified by the term "about", the claims include equivalents of the recited quantities. In one embodiment, the term "about" means within 20% of the reported numerical value.

Unless otherwise specified, the term "solid dispersion", as used herein, refers to a solid state which comprises at least two constituents, wherein one constituent is dispersed, typically homogenously or substantially homogeneously dispersed, into the other constituent or constituents. It includes solid or glassy solutions, i.e., the dispersion of the constituents is in such a way that the composition is chemically and physically homogenous in nature. In one embodiment, the first constituent is an active pharmaceutical ingredient (API), and the second constituent is a matrix that comprises a polymer, wherein the API is dispersed substantially uniformly within the matrix (the polymer). In one embodiment, the API is Compound 1. The API may be present in an amorphous state or in fine crystalline dispersed form. Also, the API may be available as a mixture of amorphous and crystalline forms. Without limitation, solid dispersions may be physically classified as a eutectic mixture, a solid solution, a glass solution or suspension, an amorphous precipitate in a glassy or crystalline carrier, a complex, a complexed formation or a combination of the different systems. In addition, solid dispersions may be prepared using various techniques known to those skilled in the art, such as by co-dissolving the API and polymer in a solvent then spray-drying, spray-congealing, solvent evaporation, freeze-drying, curing or microwaving, co-precipitation, mechanical admixture at an elevated but non-melting temperature, wet granulation, extrusion-spheronization, melt fusion, hot melt extrusion and the like. In one embodiment, the solid dispersion is obtained by spray-drying (spray-dried solid dispersion).

As used herein, unless otherwise specified or contrary from context, an "amorphous solid dispersion" of a drug substance is a homogeneous or substantially homogenous mixture of a drug substance (e.g., Compound 1) that is dispersed into a polymer which has substantially no crystalline content. A "stable amorphous solid dispersion" of a drug substance is an amorphous solid dispersion containing a drug whose structure and properties remain (i.e. retains its physical stability (e.g., remains in an amorphous state) and/or chemical stability) or can be caused to remain essentially unchanged for a period of time sufficient to allow use of the drug for the intended purpose (e.g., use in an in vivo study in an animal model or therapeutic administration to a subject). Various analytical techniques for measuring stability are available in the art including X-ray Powder Diffraction, high performance liquid chromatography, and Differential Scanning calorimetry. In some embodiments, a "stable" amorphous solid dispersion is a formulation with no significant changes observed when stored at 25° C. and 60% relative humidity or 40° C. and 75% relative humidity for one week or longer, such as up to 6 months or longer. Typical acceptable criteria for stability are as follows: No more than 10%, preferably no more than 5% or no more than 1%, or no more than 0.5% of Compound 1 is degraded as measured by HPLC. For example, in some embodiments, the formulation generated from the amorphous solid dispersion herein after storage at 25° C. and 60% relative humidity or 40° C. and 75% relative humidity for one week or longer, such as up to 6 months or longer, in comparison to the reference (the formulation generated from the fresh prepared amorphous solid dispersion), has substantially the same amount of Compound 1.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the present disclosure to a subject in need of such treatment.

The term "therapeutically effective amount," as used herein, refers to that amount of a therapeutic agent (e.g., Compound 1) sufficient to result in amelioration of one or more symptoms of a disorder or condition (e.g., a cancer associated with KRAS G12C mutation), or prevent appearance or advancement of a disorder or condition, or cause regression of or cure from the disorder or condition.

The term "subject" (alternatively referred to herein as "patient") as used herein, refers to an animal, preferably a mammal, most preferably a human, who has been the object of treatment, observation or experiment. In any of the embodiments described herein, the subject can be a human.

EXAMPLES

Example 1. General Methods

The methods described in this example are applicable to Examples 2 and 3 below.

Materials: the starting materials, reagents, solvents, etc. are generally available through commercial sources.

$^1$H NMR was performed using Bruker Advance 300 equipped with automated sampler (B-ACS 120).

POWDER X-RAY DIFFRACTION (XRPD): The solid samples were examined using X-ray diffractometer (Bruker D8 advance). The system is equipped with LynxEye detector. The X-ray wavelength is 1.5418 Å. The samples were scanned from 3 to 40° 2θ, at a step size 0.02° 2θ. The tube voltage and current were 40 KV and 40 mA, respectively.

Polarizing microscope analysis (PLM): Light microscopy was performed using a Polarizing Microscope ECLIPSE LV100POL (Nikon, JPN).

TGA ANALYSIS: TGA was carried out on a TGA Q500 or Discovery TGA 55 (TA Instruments, US). The sample was placed into an open tared aluminum pan, automatically weighed, and inserted into the TGA furnace. The sample was heated at a rate of 10° C./min from room temperature (RT) to the final temperature.

DSC ANALYSIS: DSC was performed using a DSC Q200 or Discovery DSC 250 (TA Instruments, US). The sample was placed into an aluminum pin-hole hermetic pan and the weight was accurately recorded. The sample was heated at a rate of 10° C./min from 25° C. to the final temperature.

Dynamic Moisture Sorption Analysis (DVS)

Moisture sorption/desorption data was collected on IGAsorp Dynamic Moisture Sorption Analyzer. The sample was placed into a tarred sample chamber and automatically weighed. The sample was dried at 50° C. until the humidity was less than 0.3% and cooled to 25° C. The instrument parameters were set as given below.

Sample temperature: 25° C.

Temperature stability: 0.1° C./min

Flow rate: 250 mL/min

Scans: 2

Mode: F1

Min time: 30 min

Time out: 120 min

Wait until: 98%

Beginning: with adsorption scan

Adsorption: 0, 10, 20, 30, 40, 50, 60, 70, 80, 90

Desorption: 80, 70, 60, 50, 40, 30, 20, 10, 0

HPLC Analysis

Method 1. HPLC analysis was performed with an Agilent HPLC 1260 series instrument. A representative HPLC method used for purity, solubility and stability study for Compound 1 analysis.

| | | | | |
|---|---|---|---|---|
| Column | Diamonsil C18, 4.6*200 mm, 5 μm | | | |
| Mobile Phase | A: 0.01% TFA in water | | | |
| | B: ACN | | | |
| Gradient | Time (min) | 0 | 10 | 20 |
| | Mobil phase B % | 20% | 90% | 90% |
| Column Temperature | 30° C. | | | |
| Detector | DAD; 210 nm | | | |
| Flow Rate | 1.0 mL/min | | | |
| Injection Conc. | 0.4 mg/mL | | | |
| Injection Volume | 2 μL | | | |
| Run Time | 20 minutes | | | |
| Post Time | 5 minutes | | | |
| Diluent | ACN/water (1:1) | | | |

Example 2. Preparation and Solid State Characterization of Compound 1

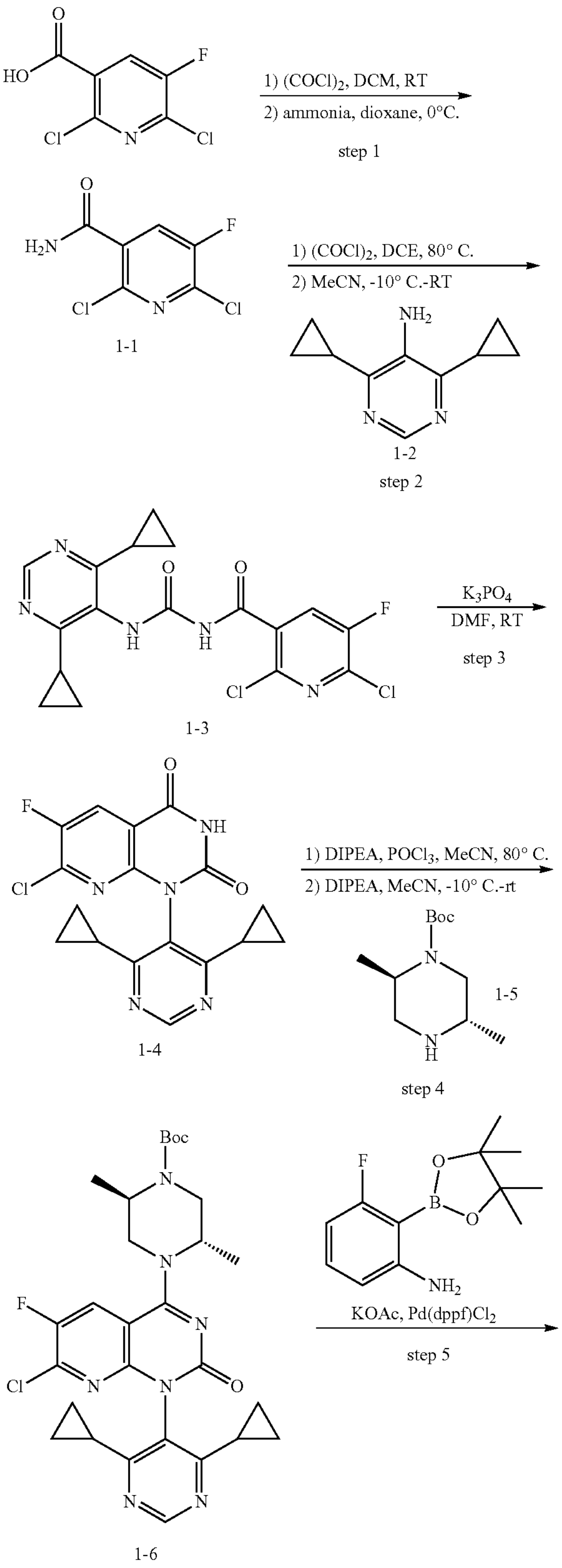

-continued

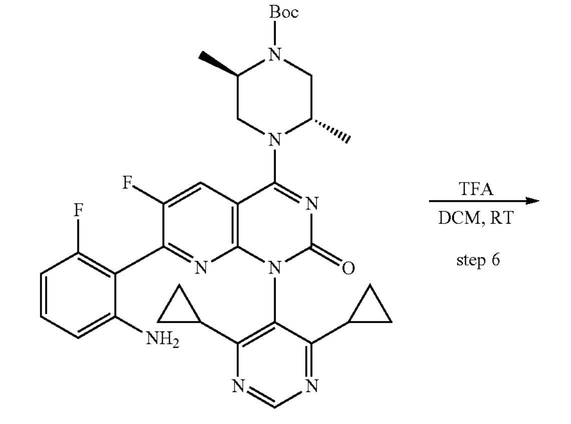

1-7

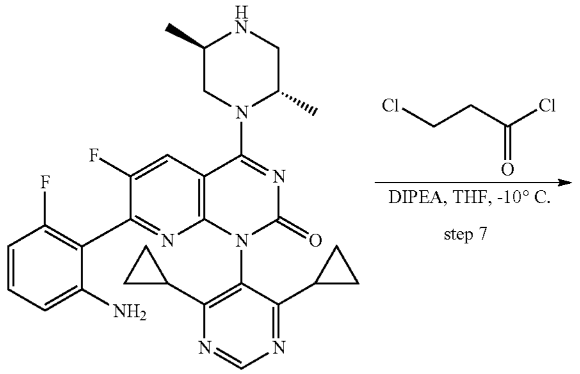

1-8

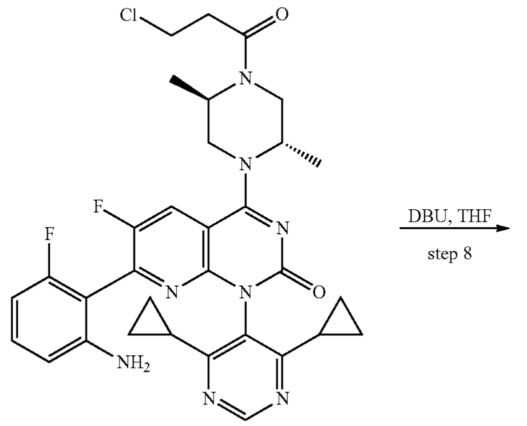

1-9

-continued

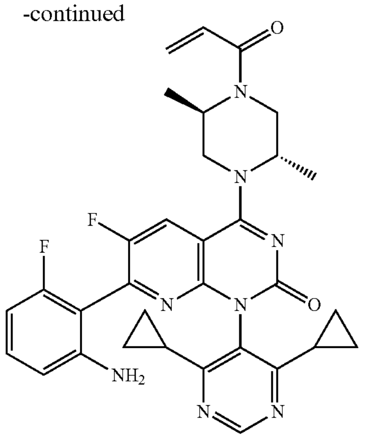

1

Step 1: To a mixture of 2,6-dichloro-5-fluoronicotinic acid (23 g, 0.11 mol) in dichloromethane (300 mL) was added dimethylformamide (0.2 mL). Oxalyl chloride (33 g, 0.26 mol) was then added slowly over 30 minutes at room temperature. The mixture was stirred at room temperature for an hour and then concentrated to give an oil which was dissolved in dioxane (50 mL). The solution was added to ammonium hydroxide (150 mL) at 0° C. over 30 minutes. The resulting mixture was stirred at 0° C. for 30 minutes and then filtered. The filter cake was washed with cooled water (50 mL) and dried to afford 1-1.

Step 2: A solution of 1-1 (11 g, 52.6 mmol) in 1,2-dichloroethane (80 mL) was treated with oxalyl chloride (8.68 g, 68.4 mmol). The mixture was stirred at 80° C. for 45 minutes and the reaction was concentrated. The residue was dissolved in acetonitrile (100 mL), cooled to −10° C., and a solution of 1-2 (9.6 g, 55.2 mmol) in THF (30 mL) was added. The resulting mixture was stirred at room temperature for 2 hours. The solution was diluted with a sat. aqueous $NaHCO_3$ solution and extracted with ethyl acetate. The organic layer was concentrated to a low volume and then heptane was added to precipitate solid. Filtered and the filter cake was washed with heptane to afford 1-3.

Step 3: To a stirred solution of 1-3 (14 g, 34.13 mmol) in DMF (84 mL) at 20-30° C. was added $K_3PO_4$ (8.7 g, 40.99 mmol). The resulting mixture was stirred at room temperature for 16 hours. The reaction was quenched with HCl (1 N) and filtered. The solid was washed with water, and then slurried in MeCN. Filtered, and the filter cake was dried to afford 1-4.

Step 4: To a solution of 1-4 (16.6 g, 44.41 mmol) and DIPEA (8.6 g, 66.54 mmol) in MeCN (83 mL) was added $POCl_3$ (8.2 g, 53.48 mmol) dropwise at room temperature. The resulting mixture was stirred at 80° C. for 45 minutes, followed by addition of DIPEA (8.6 g, 66.54 mmol) and a solution of 1-5 (9.5 g, 44.33 mmol) in MeCN (33 mL) dropwise at −10° C. After stirring at room temperature for 1 hour, the reaction was quenched with aq. $Na_2CO_3$ solution and the mixture was filtered. The solid was slurried in water and then filtered. The solid was dried to afford 1-6.

Step 5: A mixture of 1-6 (50 g, 87.71 mmol), 3-fluoro-2-(4,4,5,5-tetramethyl-1,3,2-dioxaborolan-2-yl)aniline (25 g, 105.45 mmol), Pd(dppf)$Cl_2$ (1.3 g, 0.18 mmol), KOAc (17.2 g, 175.26 mmol) and water (1.6 g) in dioxane (500 mL) was stirred at 80° C. for 2 hours under nitrogen atmosphere. The mixture was cooled and filtered. The filtrated was added to water to precipitate, and then filtered.

The solid was dissolved in DMC and was washed with aq $Na_2CO_3$ solution. The organic phase was performed solvent switch into toluene by distillation for several times. The mixture was heated in toluene at 80° C. and then cooled to 20° C. to crystallize. Filtered, and the filter cake was dried to afford 1-7.

Step 6: A mixture of 1-7 (10 g, 15.51 mmol) in DCM (50 mL) was treated with TFA (21.2 g), and the mixture was stirred at 25° C. for 3 hours. The reaction was quenched with an aq. $Na_2CO_3$ solution and the mixture was separated. The organic layer was washed with water twice and then concentrated. The residue was dissolved in EtOH and a solution of fumaric acid in EtOH was added. The mixture was filtered and the solid was washed with EtOH. The solid was added to an aq. $Na_2CO_3$ solution and the mixture was extracted with DCM. The organic layer was washed with water and then concentrated. The residue was performed a solvent switch in heptane by distillation for several times, and filtered. The filter cake was washed with heptane and dried to afford 1-8.

Step 7: To a mixture of 1-8 (10 g, 18.36 mmol) and DIPEA (2.6 g, 20.12 mmol) in THF (100 mL) was added a solution of 3-chloropropionyl chloride (2.28 g, 17.96 mmol) in THF (100 mL) at −10° C. The mixture was stirred for 1 hour and quenched with an aq. citric acid solution. The mixture was extracted with EtOAc, and the organic layer was washed with water. The organic layer was performed a solvent switch in heptane by distillation for several times, and filtered. The filter cake was washed with heptane and dried to afford 1-9.

Step 8: A mixture of 1-9 (10 g, 15.75 mmol) and DBU (4.79 g, 31.26 mmol) in THF (70 mL) and DMSO (30 mL) was stirred at 20° C. for 1 hour. EtOAc (100 mL) and an aq. citric acid solution (3%, 100 mL) were added. The mixture was separated and the organic layer was washed with water (100 mL) twice. The organic layer was performed a solvent switch in isopropanol by distillation for several times, filtered and dried to afford crude Compound 1. To the crude Compound 1 (8.5 g) was added MeOH (50 mL), and the mixture, which is a suspension, was heated at 65° C. for 30 min. Water (150 mL) was added at 65° C. and the mixture was then cooled to 25° C. at a rate of 5-10° C./hour. The mixture was stirred at 25° C. for 2-24 hours, then filtered and dried to afford Compound 1 (8.0 g, purity 99.9%, yield 84%), the solid form of which was analyzed by XRPD and DSC and was found to be consistent with crystalline Form B prepared according to the procedures shown in PCT/CN2020/137276, filed Dec. 17, 2020 and PCT/CN2019/126230, filed Dec. 18, 2019, see also Example 3 below. Representative analytical data of Compound 1 is below: LCMS (ESI, m/z): $[M+H]^+$=599.1; HNMR (400 MHz, methanol-$d_4$, ppm): δ8.73 (s, 1H), 8.26-8.22 (m, 1H), 7.15-7.09 (m, 1H), 6.84-6.74 (m, 1H), 6.53 (d, J=8.4 Hz, 1H), 6.42-6.38 (m, 1H), 6.30-6.24 (m, 1H), 5.83-5.78 (m, 1H), 5.01 (brs, 1H), 4.91-4.83 (m, 1H), 4.53-4.29 (m, 2H), 3.96-3.89 (m, 1.5H), 3.54-3.50 (m, 0.5H), 1.82-1.75 (m, 1H), 1.73-1.66 (m, 1H), 1.47 (d, J=6.8 Hz, 3H), 1.37-1.27 (m, 3H), 1.16-1.05 (m, 4H), 1.03-0.97 (m, 2H), 0.88-0.83 (m, 2H). FNMR (376 MHz, methanol-d 4, ppm): δ-114.9 (1F), −125.6 (1F).

Example 3. Alternative Method of Preparation of Form B of Compound 1

In this Example, a method of preparing Form B of Compound 1 from Compound 1 in Form A is described.

Form A: In an initial study, Compound 1 prepared via the procedure of Example 5 of PCT/CN2019/126230, filed Dec. 18, 2019 (or Example 16 of PCT/CN2020/091274, filed May 20, 2020, published as WO2020/233592), was slurried in EtOAc, and filtered to provide Compound 1 in a crystalline form A. About 1.1% of residual EtOAc was detected by $^1$H-NMR, corresponding to weight loss at 120-290° C. in TGA (FIG. 1B). Two overlapped endothermic peaks were observed by DSC (FIG. 1B). Compound 1 in Form A was heated to 250° C. and DSC profile of the residual solid was unchanged, suggesting the overlapped peak was due to melting with crystal form transformation. Thus, the starting material was an anhydrate.

Form A was very soluble in DCM (>92 mg/mL) and soluble (20-33 mg/mL) in MeOH, butanone, THF, ACN and acetone. In other solvents, Form A was practically insoluble.

Representative XRPD and DSC spectra of Form A are shown in FIG. 1A-1B. A table of XRPD peaks are shown below in Table 1.

TABLE 1

XRPD peak table for Form A

| Angle 2-Theta ° | Intensity % | Intensity Count | d value Angstrom |
|---|---|---|---|
| 6.236 | 100 | 1978 | 14.1623 |
| 7.951 | 11.7 | 232 | 11.1101 |
| 10.241 | 7.2 | 143 | 8.63058 |
| 11.636 | 6.6 | 130 | 7.59894 |
| 12.226 | 16.3 | 322 | 7.2337 |
| 12.614 | 30.8 | 610 | 7.01205 |
| 13.759 | 20.8 | 411 | 6.4308 |
| 14.761 | 31.9 | 631 | 5.99658 |
| 15.128 | 19.6 | 387 | 5.85189 |
| 17.74 | 17.6 | 348 | 4.99561 |
| 18.033 | 20.5 | 406 | 4.91521 |
| 18.975 | 7.8 | 155 | 4.67329 |
| 19.646 | 22.8 | 450 | 4.51518 |
| 19.882 | 42.7 | 844 | 4.46203 |
| 20.612 | 7.6 | 150 | 4.30569 |
| 21.24 | 16.7 | 331 | 4.17978 |
| 21.913 | 7.9 | 156 | 4.05285 |
| 22.558 | 7.2 | 143 | 3.93849 |
| 23.06 | 15.4 | 305 | 3.85385 |
| 23.428 | 8.9 | 177 | 3.79407 |
| 24.589 | 11.7 | 231 | 3.61753 |
| 25.36 | 10.5 | 207 | 3.50922 |
| 26.39 | 10.1 | 200 | 3.37458 |
| 27.447 | 7.2 | 143 | 3.24701 |
| 29.958 | 4.9 | 96 | 2.98033 |
| 30.666 | 5.8 | 114 | 2.91305 |
| 31.233 | 4.2 | 84 | 2.86149 |
| 31.999 | 4.7 | 92 | 2.79467 |
| 33.19 | 5.1 | 100 | 2.69706 |

Form B: Compound 1 in Form A was added into different methanol to provide a suspension with a concentration of 100 mg/mL. The suspensions were kept stirring at 50° C. for 1 day. Solid samples were collected by filtration and analyzed by XRPD, DSC, and TGA. No weight loss at 60-280° C. was observed by TGA, and the melting endothermic peak was at 289-290° C. with enthalpy of 95 J/g by DSC (FIG. 2B). The sample was an anhydrate, and assigned as Form B.

Figure 2C:
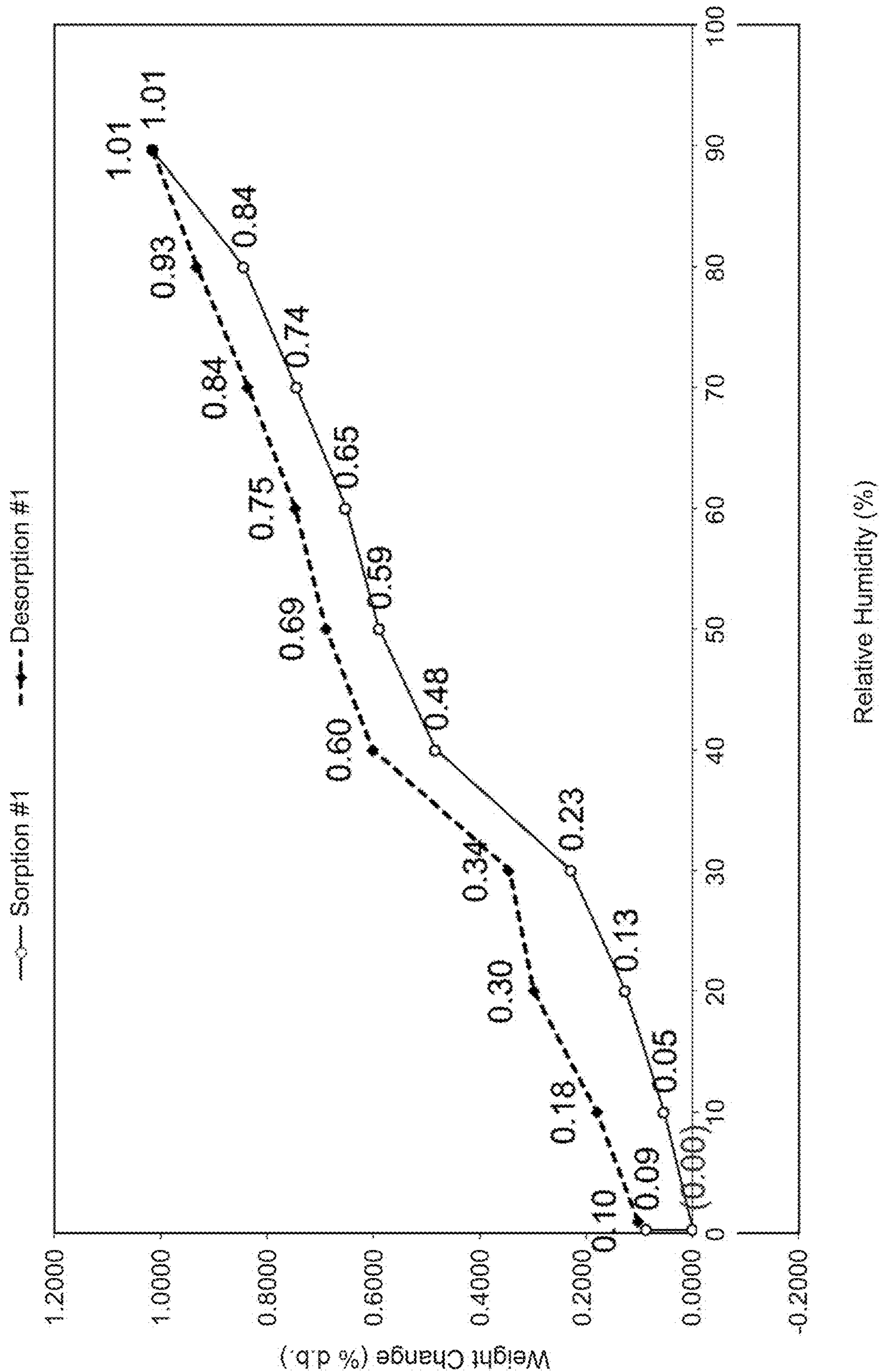
Figure 2D:
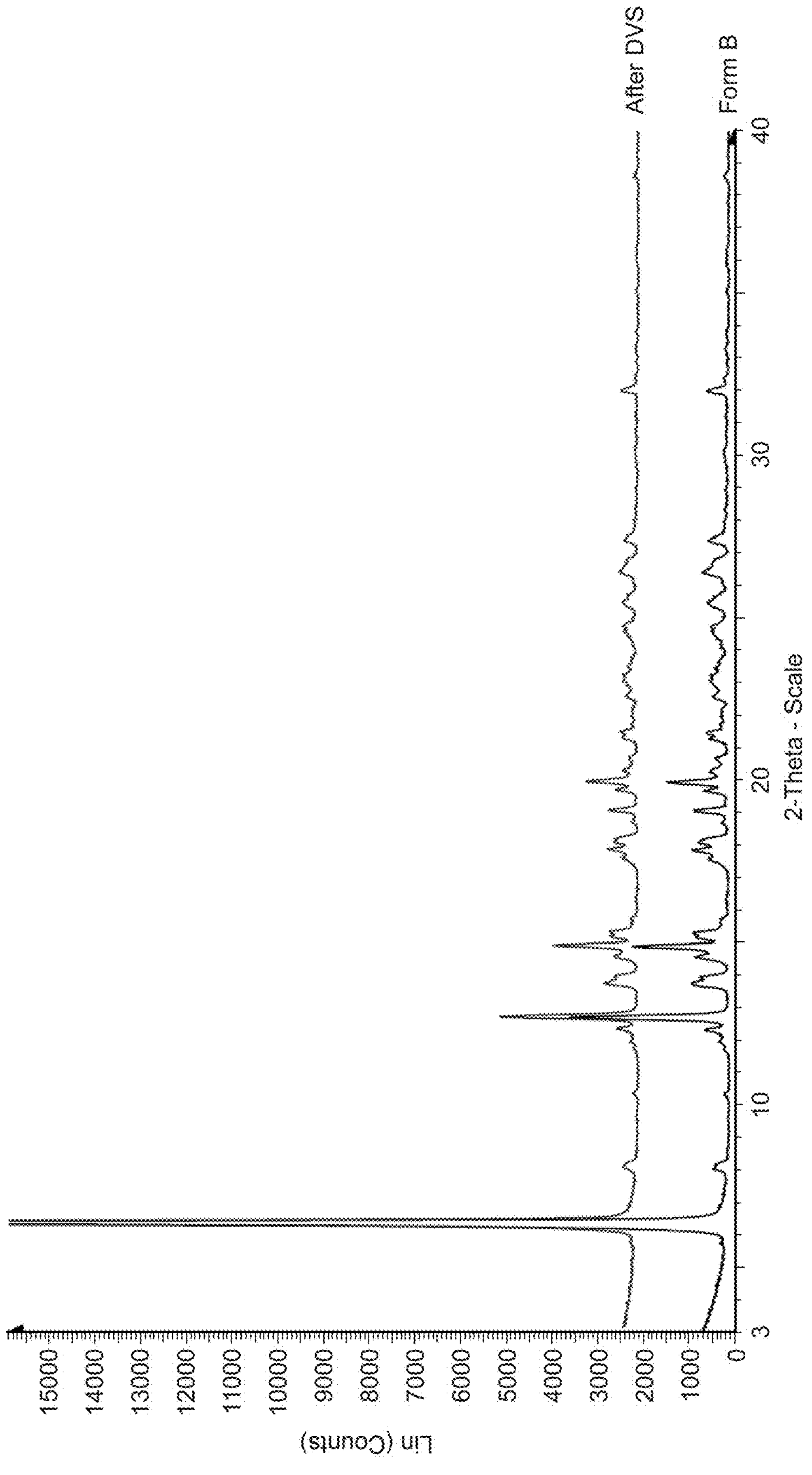

Small scale up of Form B: Form B was small scaled up for DVS analysis, solubility and stability studies. 103.02 mg of Compound 1 in Form A was dissolved in 5 mL of MeOH (48V) at RT. After filtration, 10 mL of water was added into the filtrate. Precipitation occurred quickly. The suspension was kept stirring at RT for about 2 hours. Solid samples were collected by filtration, dried under vacuum at 50° C. overnight. 94.16 mg solid was obtained with a yield of 91%. This solid was used for the DVS testing. Form B was slightly hygroscopic and absorbed ~0.84% water at 0-80% RH (FIG. 2C) without changing of crystal form after DVS testing (FIG. 2D).

Representative XRPD and DSC spectra of Form B are shown in FIG. 2A-2B. A table of XRPD peaks are shown below in Table 2.

TABLE 2

XRPD peak table for Form B.

| Angle 2-Theta ° | Intensity % | Intensity Count | d value Angstrom |
|---|---|---|---|
| 5.69 | 8.2 | 382 | 15.5188 |
| 6.249 | 100 | 4660 | 14.1315 |
| 7.983 | 6.4 | 300 | 11.0664 |
| 10.224 | 3.4 | 159 | 8.64514 |
| 10.562 | 2.3 | 107 | 8.36905 |
| 11.622 | 3.3 | 152 | 7.60784 |
| 11.861 | 3.8 | 176 | 7.45548 |
| 12.213 | 6.9 | 320 | 7.24107 |
| 12.617 | 87.7 | 4086 | 7.01017 |
| 13.639 | 11.9 | 556 | 6.48694 |
| 13.832 | 7.8 | 362 | 6.39688 |
| 14.472 | 11.1 | 516 | 6.11544 |
| 14.799 | 24 | 1118 | 5.98135 |
| 15.19 | 8.6 | 400 | 5.82825 |
| 15.599 | 3.8 | 177 | 5.67608 |
| 16.236 | 2.3 | 107 | 5.45499 |
| 17.501 | 6 | 281 | 5.06339 |
| 17.76 | 10.6 | 492 | 4.99 |
| 18.044 | 7.7 | 357 | 4.91227 |
| 18.614 | 3.9 | 181 | 4.76309 |
| 18.992 | 22.8 | 1063 | 4.66909 |
| 19.627 | 7.8 | 362 | 4.5195 |
| 19.863 | 19.8 | 923 | 4.46617 |
| 20.222 | 8.2 | 382 | 4.38775 |
| 20.597 | 5.9 | 276 | 4.30877 |
| 21.243 | 7 | 327 | 4.17919 |
| 21.403 | 10.1 | 470 | 4.14823 |
| 22.043 | 3.9 | 184 | 4.02928 |
| 22.514 | 6.3 | 292 | 3.94595 |
| 22.978 | 7.6 | 353 | 3.86739 |
| 23.13 | 7 | 324 | 3.84236 |
| 23.61 | 4.8 | 226 | 3.76525 |
| 24.37 | 5.8 | 271 | 3.64959 |
| 24.614 | 5.5 | 257 | 3.61396 |
| 25.42 | 9.8 | 456 | 3.50109 |
| 26.333 | 10.7 | 500 | 3.38178 |
| 26.674 | 7.9 | 369 | 3.33928 |
| 27.314 | 9 | 419 | 3.26247 |
| 28.271 | 2.9 | 135 | 3.15423 |
| 28.895 | 2.8 | 130 | 3.08743 |
| 29.943 | 3.4 | 159 | 2.98172 |
| 31.175 | 2.9 | 135 | 2.86664 |
| 31.948 | 16.6 | 772 | 2.79904 |
| 32.323 | 3.3 | 152 | 2.7674 |
| 33.731 | 2.3 | 109 | 2.65502 |
| 35.027 | 2.3 | 107 | 2.55972 |
| 35.958 | 2.8 | 131 | 2.49556 |
| 36.25 | 2.4 | 112 | 2.47612 |
| 37.268 | 2.2 | 103 | 2.41081 |
| 38.577 | 5.2 | 241 | 2.33197 |

Solid State Stability of Form B: About 10 mg of Form B was open placed at 40° C./75% RH and 60° C. for 7 days and at 25° C./92.5% RH for 10 days, respectively. Prepare samples in duplicate (n =2) per condition. The solids were analyzed by XRPD and HPLC (only for 40° C./75% RH and 60° C.).

The results were summarized in Table 3. Form B was physically stable at test conditions; crystal form was unchanged. Form B was chemically stable at 40° C./75% RH for 7 days, however, slight degradation was observed at 60° C. for 7 days, purity decreased by 0.16% and two new impurities (RRT 0.86 and RRT 0.93) were detected.

TABLE 3

Stability Evaluation Results

| Initial Purity (Area %) | Purity-7 d (Area %) 40° C./ 75% RH | Purity-7 d (Area %) 60° C. | XRPD 40° C./ 75% RH After 7 d | XRPD 60° C. After 7 d | XRPD 25° C./ 92.5% RH After 10 d |
|---|---|---|---|---|---|
| 98.98 | 98.97 | 98.82 | Unchanged | Unchanged | Unchanged |

Example 4. Preparation of Amorphous Solid Dispersion of Compound 1 with 20% Drug Load This example prepares spray dried amorphous solid dispersion of compound 1 in various polymers using a 20% drug load.

In particular, PVP-VA64, PVP-K30, Eudragit E100, Soluplus, P188, HPMC-AS HG, HPMC-AS MG, HPMC-E3 LV and HPC SSL were used as polymer carriers to prepare spray dried solid dispersions ("SDDs"), with a drug load of 20%. The polymers used for this study were commercially available:

| Name | Manufacturer | Batch No. |
|---|---|---|
| Kollidon VA64 (PVP-VA 64) | BASF | 95086647G0 |
| Kollidon ® 30 (PVP K30) | BASF | 05815688Q0 |
| HPMC-AS MG | Ashland | SF60G410004 |
| HPMC-AS HG | Ashland | 65G-510006 |
| Poloxamer 188 (Kolliphor ® P188) | BASF | GNA19221B |
| Soluplus | BASF | 20747936W0 |
| HPMC E3 LV | Colorcon | PDR463794 |
| Eudragit ® E100 | EVONIK industries | B160401554 |
| Hydroxypropyl cellulose HPC-SSL | Nisso | NHC-0431 |

Compound 1 (in Form B) and different polymer (1:4, w/w) with the concentration of Compound 1 of 10 mg/mL were dissolved in organic solvents as spray drying solution for solid dispersion preparation. As a control, Compound 1 without any polymer was also used to prepare a spray dried powder. The formulation details and solvents used to prepare the spray drying solution are shown in the table below:

| Spray Dried Dispersion Nos. | Formulation composition (w/w) | Compound 1 concentration (mg/mL) | Solvents |
|---|---|---|---|
| SDD-0 | Compound 1 (100%) | 10 | Acetone |
| SDD-1 | Compound 1/PVP-VA64 = 20:80 | 10 | Acetone |
| SDD-2 | Compound 1/PVP-K30 = 20/80 | 10 | MeOH |
| SDD-3 | Compound 1/Eudragit E100 = 20/80 | 10 | MeOH |
| SDD-4 | Compound 1/Soluplus = 20/80 | 10 | Acetone |

-continued

| Spray Dried Dispersion Nos. | Formulation composition (w/w) | Compound 1 concentration (mg/mL) | Solvents |
|---|---|---|---|
| SDD-5 | Compound 1/HPMC-AS HG = 20/80 | 10 | Acetone |
| SDD-6 | Compound 1/HPMC-AS MG = 20/80 | 10 | Acetone |
| SDD-7 | Compound 1/HPMC E3 LV = 20/80 | 10 | MeOH:DCM = 1:1 |
| SDD-8 | Compound 1/HPC = 20/80 | 10 | MeOH:DCM = 1:1 |

The solutions were spray dried by BUCHI B290. Spray drying parameters: Nozzle size (mm), 0.7; Settings: Inlet, ° C., 90; Aspirator, %; 100; Pump, %, 50; Q-flow, mm, 40. The actual inlet and outlet temperatures as well as yields for solid dispersion preparation were listed in Tables 4A and 4B below. The collected powders were dried under vacuum at 40° C. overnight and then stored at 2-8° C.

TABLE 4A

Spray drying parameters for solid dispersion preparation

| | Solvent | Acetone | Acetone | MeOH | MeOH | Acetone |
|---|---|---|---|---|---|---|
| Actual | Inlet, ° C. | | | 87-93 | | |
| | Outlet, ° C. | 58-62 | 57-62 | 50-55 | 54-58 | 50-58 |
| Spray Dried Dispersion Nos. | | SDD-0 | SDD-1 | SDD-2 | SDD-3 | SDD-4 |
| Yield (%) | | 43.6% | 64.1% | 53.9% | 53.9% | 52.5% |

TABLE 4B

Spray drying parameters for solid dispersion preparation

| | Solvent | Acetone | Acetone | MeOH:DCM = 1:1 | MeOH:DCM = 1:1 |
|---|---|---|---|---|---|
| Actual | Inlet, ° C. | | | 87-93 | |
| | Outlet, ° C. | 58-62 | 57-62 | 50-55 | 54-58 |
| Spray Dried Dispersion Nos. | | SDD-5 | SDD-6 | SDD-7 | SDD-8 |
| Yield (%) | | 49.1% | 49.8% | 27.6% | 58.8% |

Figure 3:
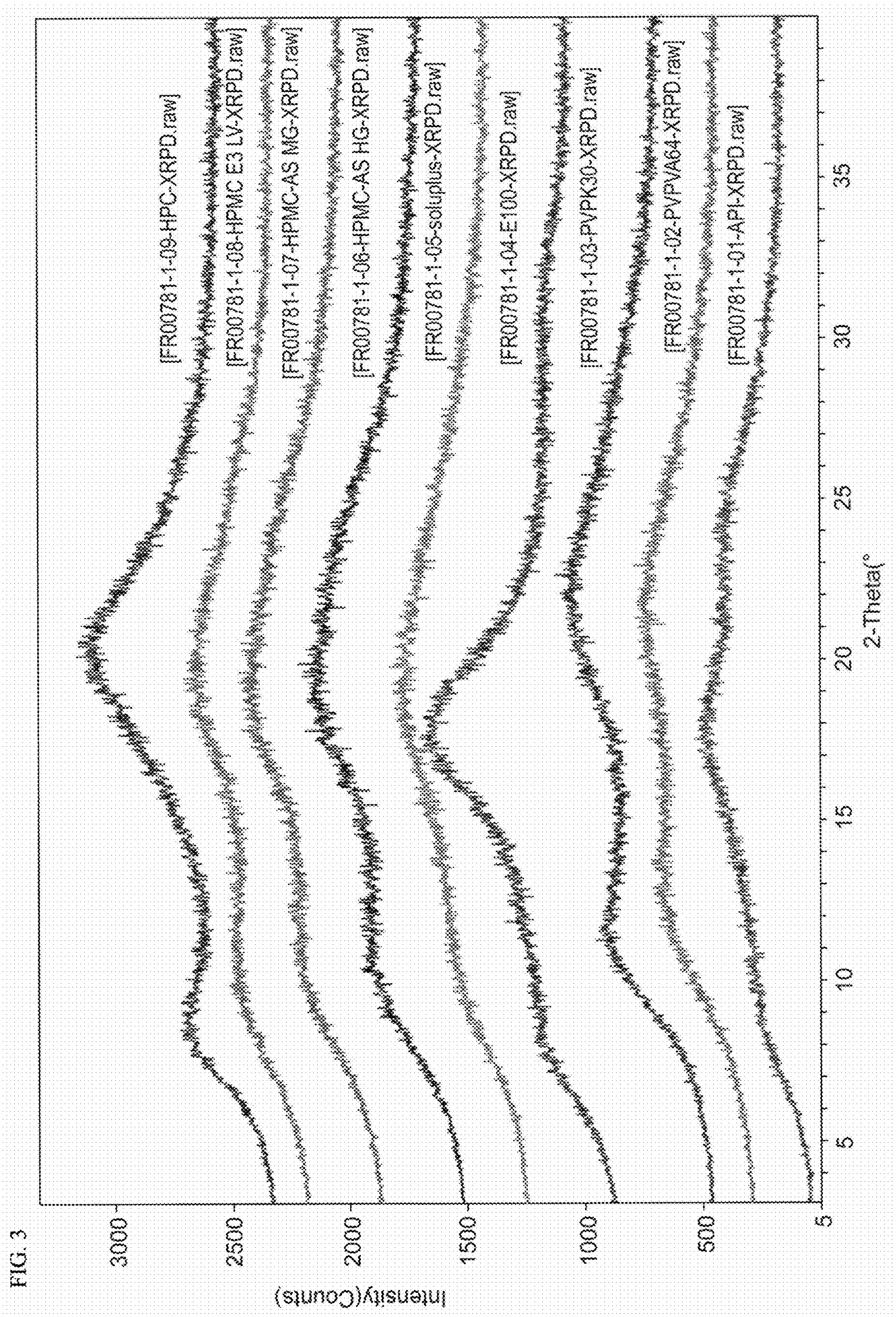
FIG. 3 shows an overlay of representative XRPD spectrum for SDD-0 to SDD-8, the spectra are arranged with the following order, from the bottom up, sequentially, SDD-0, SDD-1, SDD-2, SDD-3, SDD-4, SDD-5, SDD-6, SDD-7, and SDD-8, with the XRPD spectrum for SDD-8 on the top.

The spray dried powders were analyzed by PLM, XRPD, UPLC (Ultra-performance liquid chromatography) and mDSC (modulated DSC). Based on XRPD (see FIG. 3) and PLM results, all spray dried products were amorphous solid dispersions. The analytical results are summarized in the table below:

TABLE 5

Characterization of SDD

| Spray Dried Dispersion Nos. | XRPD | PLM | mDSC | Drug load (w %) | Purity (%) |
|---|---|---|---|---|---|
| SDD-0 | Amorphous | Amorphous | 156.0 | 98.7 | 98.83 |
| SDD-1 | Amorphous | Amorphous | 118.4 | 20.8 | 98.84 |
| SDD-2 | Amorphous | Amorphous | 166.0 | 18.6 | 98.77 |
| SDD-3 | Amorphous | Amorphous | 67.8 | 20.5 | 98.8 |
| SDD-4 | Amorphous | Amorphous | 108.1 | 20.8 | 98.82 |
| SDD-5 | Amorphous | Amorphous | 123.7 | 20.9 | 98.77 |
| SDD-6 | Amorphous | Amorphous | 123.7, 149.6 | 20.9 | 98.74 |
| SDD-7 | Amorphous | Amorphous | 135.8 | 20.8 | 98.82 |
| SDD-8 | Amorphous | Amorphous | 87.1 | 20.1 | 98.74 |

A brief description of the methods used for PLM, XRPD, Purity and mDSC analysis of the above SDD samples is shown below.

PLM analysis of the SDD samples were conducted using Nikon LV100POL equipped with 5 megapixel CCD, with the physical lens set at 20×.

For XRPD analysis, samples were spread onto the Si-substrate for XRPD test using the parameters as below: Tube: Cu: K-Alpha (λ=1.5418 Å); Generator: Voltage: 40 kV; Current: 40 mA; Scan Scope: 2 or 3 to 40 deg; Time/step(s) 0.06 s; Total time(s) 120 s or 117.36 s.

For mDSC analysis, SDD powders were weighed into Tzero aluminum sample pan from TA Instruments covered by pinhole lid for mDSC test using the parameters as below: Start temperature at 30° C.; Modulate +/−1° C. every 60 seconds; Ramp 2° C./min to 300° C.

The UPLC method used for the assay and purity analysis above is UPLC Method 1, which is shown below:

| Instrument | Agilent 1290 infinityII | | |
|---|---|---|---|
| Column | ACQUITY UPLC ® BEH C18, 1.7 um 2.1*100 mm | | |
| Gradient | Time (min) | A %: 0.05% TFA in water (v/v) | B %: 0.05% TFA in ACN (v/v) |
| | 0 | 90 | 10 |
| | 13 | 63 | 37 |
| | 15 | 63 | 37 |
| | 19 | 10 | 90 |
| | 22 | 10 | 90 |
| | 22.1 | 90 | 10 |
| | 25 | 90 | 10 |
| Injection volume | 2 μL | | |
| Flow rate | 0.5 mL/min | | |
| Column Temp. | 30° C. | | |
| Wavelength | 220 nm | | |
| Diluent | ACN | | |
| Concentration | 0.2 mg/mL | | |

Dissolution evaluation in FaSSIF medium: To evaluate in-vitro release performance of SDDs, dissolution in FaSSIF (pH=6.5±0.05) was performed, and the crystalline Compound 1 (Form B) was also tested as control.

Appropriate amount of Compound 1 or SDD (SDD-0 to SDD-8) was weighed into 40-mL glass vials respectively, and then added 10 mL of FaSSIF medium to a target API concentration of 1 mg/mL, followed by hand shake to suspend well. Place the glass bottle on 37° C. hot-stage by stirring magnetically at 200 rpm. At each time point of 10 min, 20 min, 40 min, 60 min and 120 min, 500 μL suspension was pipetted respectively and centrifuged (14,000 rpm, 3 min) to isolate supernatant and dilute with diluent for UPLC analysis. Finally, the pH value of solution (120 min) were measured by pH meter. The dissolution results were shown in Table 6.

TABLE 6

Dissolution test of API (Compound 1) and SDD in FaSSIF (10 mL)

| | API concentration in dissolution medium (μg/mL) | | | | | |
|---|---|---|---|---|---|---|
| Sample | 10 min | 20 min | 40 min | 60 min | 120 min | pH |
| Compound 1 (Form B) | 12.5 | 13.8 | 15.0 | 15.5 | 15.9 | 6.42 |
| SDD-0 | 219.4 | 247.6 | 31.5 | 32.2 | 28.5 | 6.47 |
| SDD-1 | 423.4 | 265.3 | 47.9 | 42.3 | 34.4 | 6.47 |
| SDD-2 | 315.9 | 45.6 | 41.4 | 40.4 | 28.8 | 6.45 |
| SDD-3 | 738.8 | 724.3 | 669.3 | 641.4 | 575.1 | 6.90 |
| SDD-4 | 248.3 | 246.1 | 242.1 | 243.6 | 238.2 | 6.41 |
| SDD-5 | 271.2 | 260.6 | 262.4 | 262.5 | 261.3 | 6.32 |
| SDD-6 | 492.5 | 494.5 | 487.2 | 491.8 | 503.9 | 6.05 |
| SDD-7 | 392.9 | 146.8 | 90.1 | 74.7 | 63.5 | 6.42 |
| SDD-8 | 401.9 | 379.7 | 346.7 | 150.0 | 93.2 | 6.42 |

The UPLC method used for the dissolution analysis above is UPLC Method 2, which is shown below:

| | |
|---|---|
| Instrument | Agilent 1290 infinityII |
| Column | ACQUITY UPLC BEH C18, 1.7 um 2.1*50 mm (PDS-HPLC-231) |

-continued

| Gradient | Time (min) | A %: 0.1% TFA in water (v/v) | B %: 0.1% TFA in ACN (v/v) |
|---|---|---|---|
| | 0 | 90 | 10 |
| | 2.5 | 40 | 60 |
| | 4.5 | 10 | 90 |
| Post-time | 0.5 min | | |
| Injection volume | 1 μL | | |
| Flow rate | 0.5 mL/min | | |
| Column Temp. | 40° C. | | |
| Wavelength | 220 nm | | |
| Diluent | ACN | | |
| Concentration | 0.2 mg/mL | | |

1-week stability evaluation of SDD: The conditions of stability test were shown in Table 7. Appropriate quantity of SDDs and crystalline Compound 1 (Form B) were placed into 40-mL vials respectively.

TABLE 7

The conditions for stability of API and SDDs

| Conditions | 1-week |
|---|---|
| 4° C. (closed) | Appearance and XRPD |
| 25° C./60% RH (open) | Appearance and XRPD |
| 40° C./75% RH (open) | Appearance and XRPD |

The samples (closed) were covered by plastic cap tightly and sealed by parafilm and samples (open) were just covered by aluminum foil with pinholes. Then they were stored at 2-8° C., 25° C./60% RH and 40° C./75% RH stability chamber respectively for 1 week. The samples were analyzed by XRPD to check the physical stability, and meanwhile dissolved with diluent for UPLC analysis (UPLC Method 1) to check the chemical stability. The results were summarized in Table 8 below.

TABLE 8

Summary of 1-week stability test for SDD

| Sample | Initial purity (%) | Storage condition | Appearance | XRPD | Purity (%) |
|---|---|---|---|---|---|
| Compound 1 (Form B) | 98.75 | 2-8° C., closed | Yellow powder | Crystal | 98.81 |
| | | 25° C./60% RH, open | Yellow powder | Crystal | 98.86 |
| | | 40° C./75% RH, open | Yellow powder | Crystal | 98.79 |
| SDD-0 | 98.83 | 2-8° C., closed | Yellow powder | Amorphous | 98.75 |
| | | 25° C./60% RH, open | Yellow powder | Amorphous | 98.77 |
| | | 40° C./75% RH, open | Yellow powder | Amorphous | 98.77 |
| SDD-1 | 98.84 | 2-8° C., closed | Yellow powder | Amorphous | 98.77 |
| | | 25° C./60% RH, open | Yellow powder | Amorphous | 98.84 |
| | | 40° C./75% RH, open | Yellow solid, serious agglomeration | Amorphous | 98.63 |
| SDD-2 | 98.77 | 2-8° C., closed | Yellow powder | Amorphous | 98.75 |
| | | 25° C./60% RH, open | Yellow powder | Amorphous | 98.74 |
| | | 40° C./75% RH, open | Yellow solid, agglomeration | Amorphous | 98.47 |
| SDD-3 | 98.80 | 2-8° C., closed | Yellow powder | Amorphous | 98.74 |
| | | 25° C./60% RH, open | Yellow powder | Amorphous | 98.68 |
| | | 40° C./75% RH, open | Yellow powder | Amorphous | 98.46 |

TABLE 8-continued

| Summary of 1-week stability test for SDD | | | | | |
|---|---|---|---|---|---|
| Sample | Initial purity (%) | Storage condition | Appearance | XRPD | Purity (%) |
| SDD-4 | 98.82 | 2-8° C., closed | Yellow powder | Amorphous | 98.81 |
| | | 25° C./60% RH, open | Yellow powder | Amorphous | 98.88 |
| | | 40° C./75% RH, open | Yellow solid, serious agglomeration | Amorphous | 98.71 |
| SDD-5 | 98.77 | 2-8° C., closed | Yellow powder | Amorphous | 98.78 |
| | | 25° C./60% RH, open | Yellow powder | Amorphous | 98.69 |
| | | 40° C./75% RH, open | Yellow powder | Amorphous | 97.99 |
| SDD-6 | 98.74 | 2-8° C., closed | Yellow powder | Amorphous | 98.72 |
| | | 25° C./60% RH, open | Yellow powder | Amorphous | 98.53 |
| | | 40° C./75% RH, open | Yellow powder | Amorphous | 97.26 |
| SDD-7 | 98.82 | 2-8° C., closed | Yellow powder | Amorphous | 98.84 |
| | | 25° C./60% RH, open | Yellow powder | Amorphous | 98.83 |
| | | 40° C./75% RH, open | Yellow powder | Amorphous | 98.64 |
| SDD-8 | 98.74 | 2-8° C., closed | Yellow powder | Amorphous | 98.84 |
| | | 25° C./60% RH, open | Yellow powder | Amorphous | 98.81 |
| | | 40° C./75% RH, open | Yellow solid, agglomeration | Amorphous | 98.58 |

Example 5. Preparation of Amorphous Solid Dispersion of Compound 1 With 30-50% Drug Load In this example, amorphous solid dispersion by spray dry method with 30%, 40% and 50% drug loads were prepared similar to the methods described in Example 4. The details of formulations were shown in Table 9. The physical characterization, in vitro dissolution performance and 1-week stability were carried out to evaluate the different drug load of SDD formulations, similar to those described in Example 4.

TABLE 9

| Information of formulations with different drug loads | | | |
|---|---|---|---|
| Spray Dried Dispersion No. | Formulation composition (w/w) | Compound 1 concentration (mg/mL) | Solvents |
| SDD-9 | Compound 1/Soluplus = 30/70 | 10 | Acetone |
| SDD-10 | Compound 1/Soluplus = 40/60 | 10 | Acetone |
| SDD-11 | Compound 1/Soluplus = 50/50 | 10 | Acetone |
| SDD-12 | Compound 1/HPC = 30/70 | 10 | MeOH:DCM = 1:1 |
| SDD-13 | Compound 1/HPC = 40/60 | 10 | MeOH:DCM = 1:1 |
| SDD-14 | Compound 1/HPC = 50/50 | 10 | MeOH:DCM = 1:1 |
| SDD-15 | Compound 1/HPMC E3 LV = 30/70 | 10 | MeOH:DCM = 1:1 |
| SDD-16 | Compound 1/HPMC E3 LV = 40/60 | 10 | MeOH:DCM = 1:1 |
| SDD-17 | Compound 1/HPMC E3 LV = 50/50 | 10 | MeOH:DCM = 1:1 |
| SDD-18 | Compound 1/Eudragit E100 = 30/70 | 10 | MeOH |
| SDD-19 | Compound 1/Eudragit E100 = 40/60 | 10 | MeOH |
| SDD-20 | Compound 1/Eudragit E100 = 50/50 | 10 | MeOH |

The solid dispersions prepared were characterized with methods similar to those described in Example 4. The results are shown in the Table 10 below.

TABLE 10

| Characterization of SDD-9 to SDD-20 | | | | | | |
|---|---|---|---|---|---|---|
| Sample Nos. | XRPD | PLM | Tg (° C.) wet | Tg (° C.) dry | Drug load (w %) | Purity (%) |
| SDD-9 | Amorphous | Amorphous | No obvious Tg | 101.4 | 32.0 | 98.96 |
| SDD-10 | Amorphous | Amorphous | No obvious Tg | No obvious Tg | 42.0 | 98.96 |
| SDD-11 | Amorphous | Amorphous | No obvious Tg | No obvious Tg | 53.2 | 99.02 |
| SDD-12 | Amorphous | Amorphous | No obvious Tg | 92.0 | 33.1 | 98.95 |
| SDD-13 | Amorphous | Amorphous | No obvious Tg | 96.8 | 43.9 | 99.02 |
| SDD-14 | Amorphous | Amorphous | No obvious Tg | 105.4 | 51.8 | 98.98 |
| SDD-15 | Amorphous | Amorphous | No obvious Tg | 137.4 | 31.9 | 99.03 |
| SDD-16 | Amorphous | Amorphous | No obvious Tg | 138.2 | 40.7 | 98.94 |
| SDD-17 | Amorphous | Amorphous | 139.8 | 140.2 | 55.4 | 98.91 |
| SDD-18 | Amorphous | Amorphous | 154.6 | 74.4, 156.0 | 31.1 | 98.73 |
| SDD-19 | Amorphous | Amorphous | 96.7, 154.7 | 86.0, 154.5 | 41.8 | 99.02 |
| SDD-20 | Amorphous | Amorphous | 101.4, 156.7 | 95.0, 151.8 | 54.0 | 98.98 |

Figure 4A:
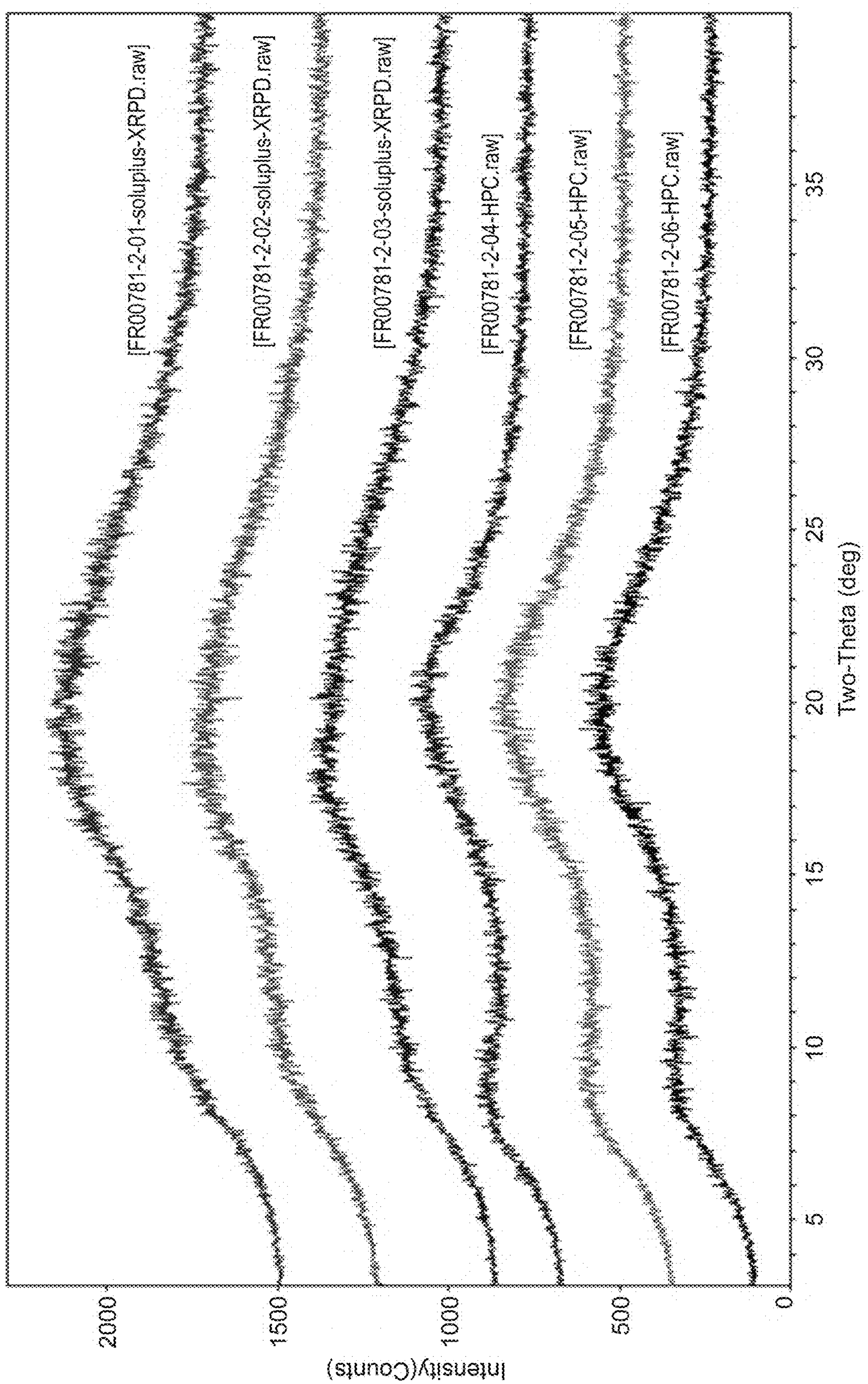
FIG. 4A shows an overlay of representative XRPD spectrum for SDD-9 to SDD-14, the spectra are arranged with the following order, from the bottom up, sequentially, SDD-14, SDD-13, SDD-12, SDD-11, SDD-10, and SDD-9, with the XRPD spectrum for SDD-9 on the top.
Figure 4B:
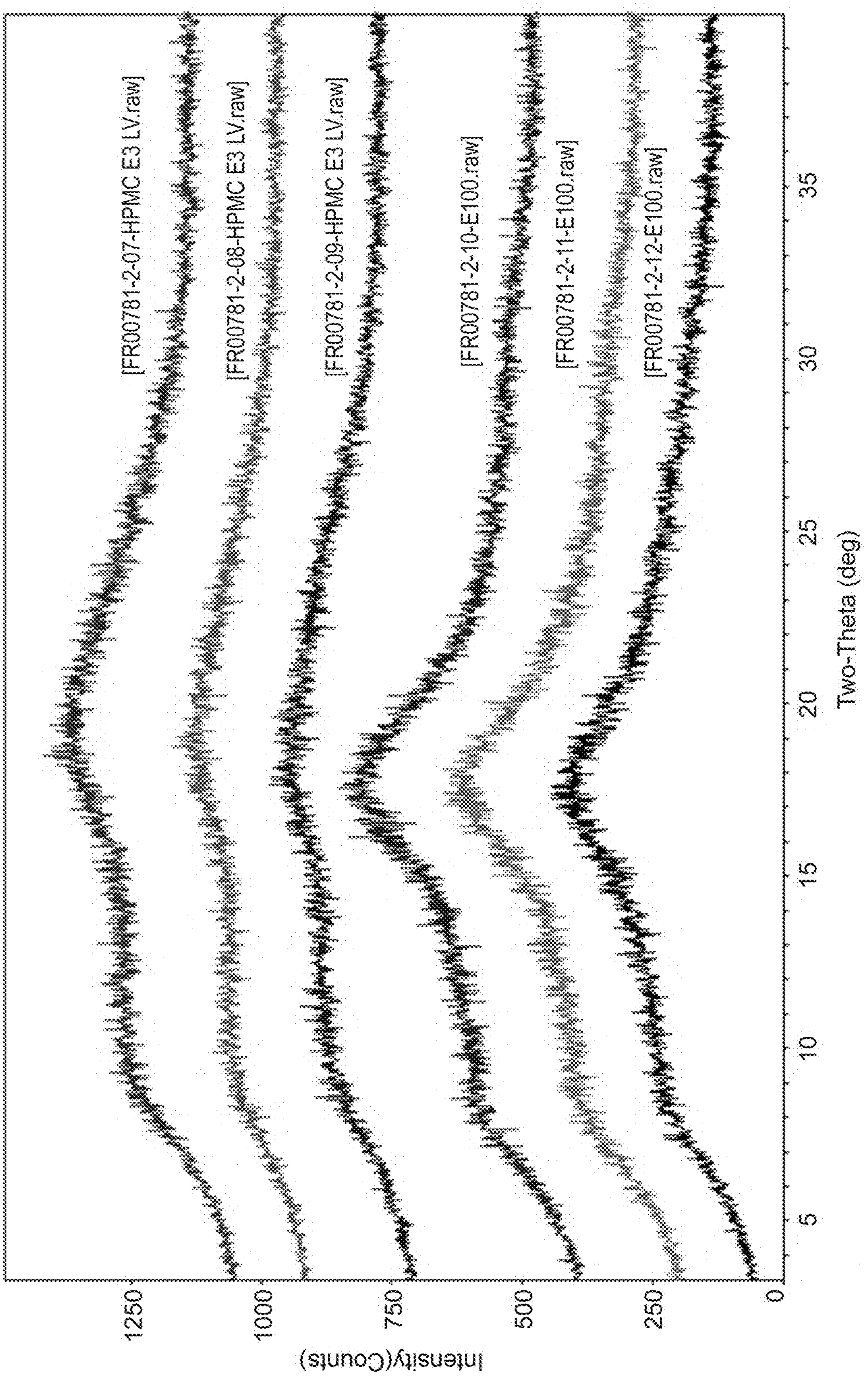
FIG. 4B shows an overlay of representative XRPD spectrum for SDD-15 to SDD-20, the spectra are arranged with the following order, from the bottom up, sequentially, SDD-20, SDD-19, SDD-18, SDD-17, SDD-16, and SDD-15, with the XRPD spectrum for SDD-15 on the top.
Figure 5A:
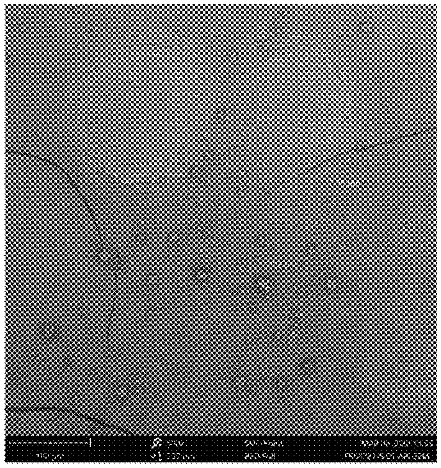
FIG. 5A shows the SEM images of SDD-0A, SDD-10A, SDD-13A, and SDD-19A.
Figure 5A:
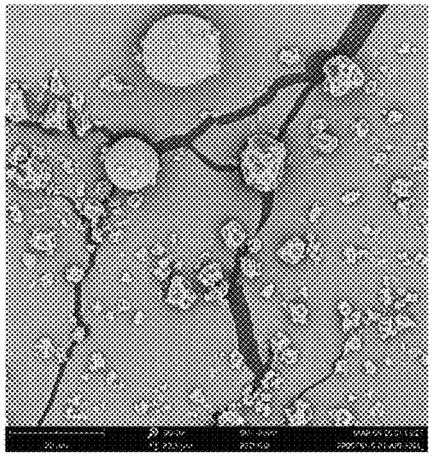
Figure 5A:
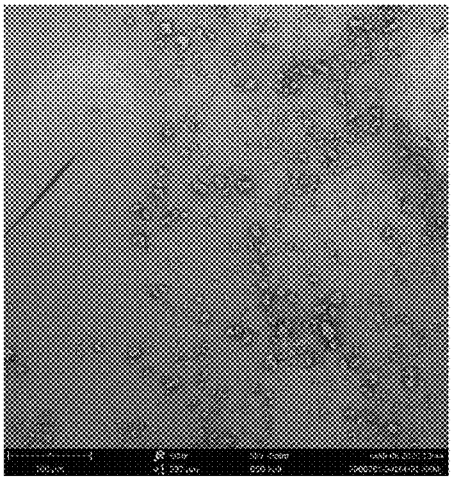
Figure 5A:
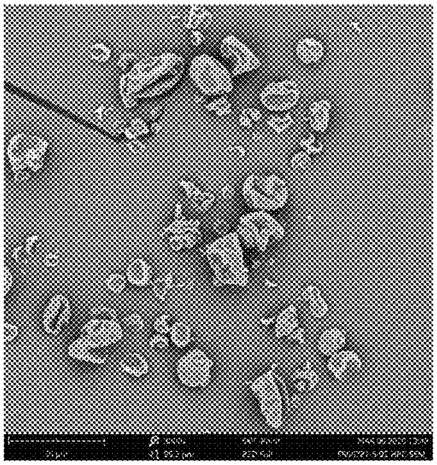
Figure 5A:
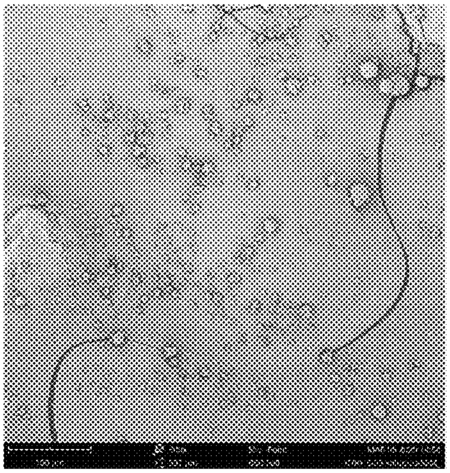
Figure 5A:
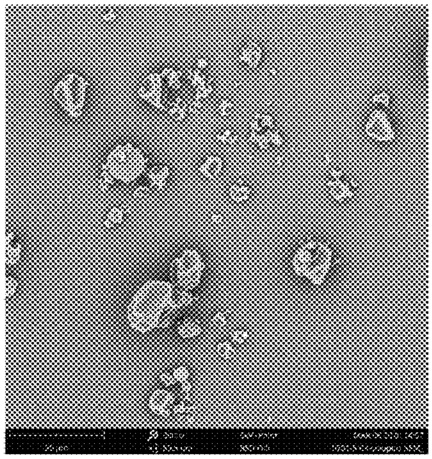
Figure 5A:
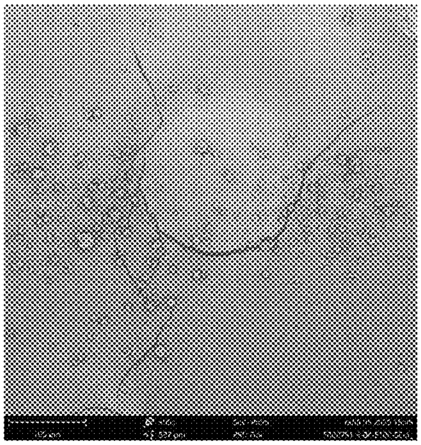
Figure 5A:
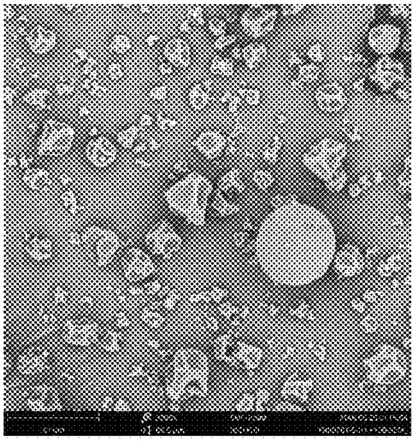
Figure 5B:
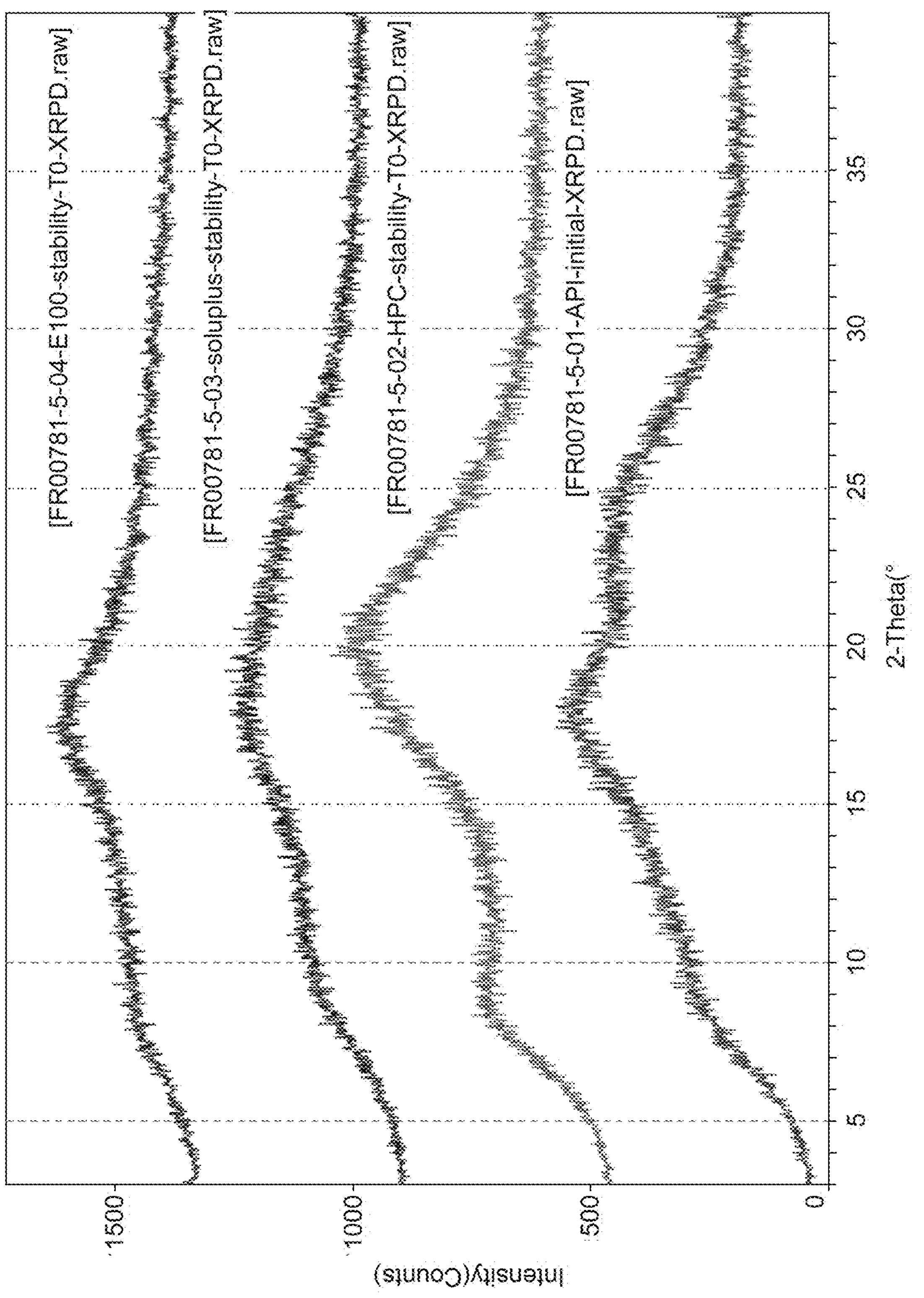
FIG. 5B shows an overlay of representative XRPD spectrum for SDD-0A, SDD-10A, SDD-13A, and SDD-19A, the spectra are arranged with the following order, from the bottom up, sequentially, SDD-0A, SDD-13A, SDD-10A, and SDD-19A, with the XRPD spectrum for SDD-19A on the top.
Figure 5C:
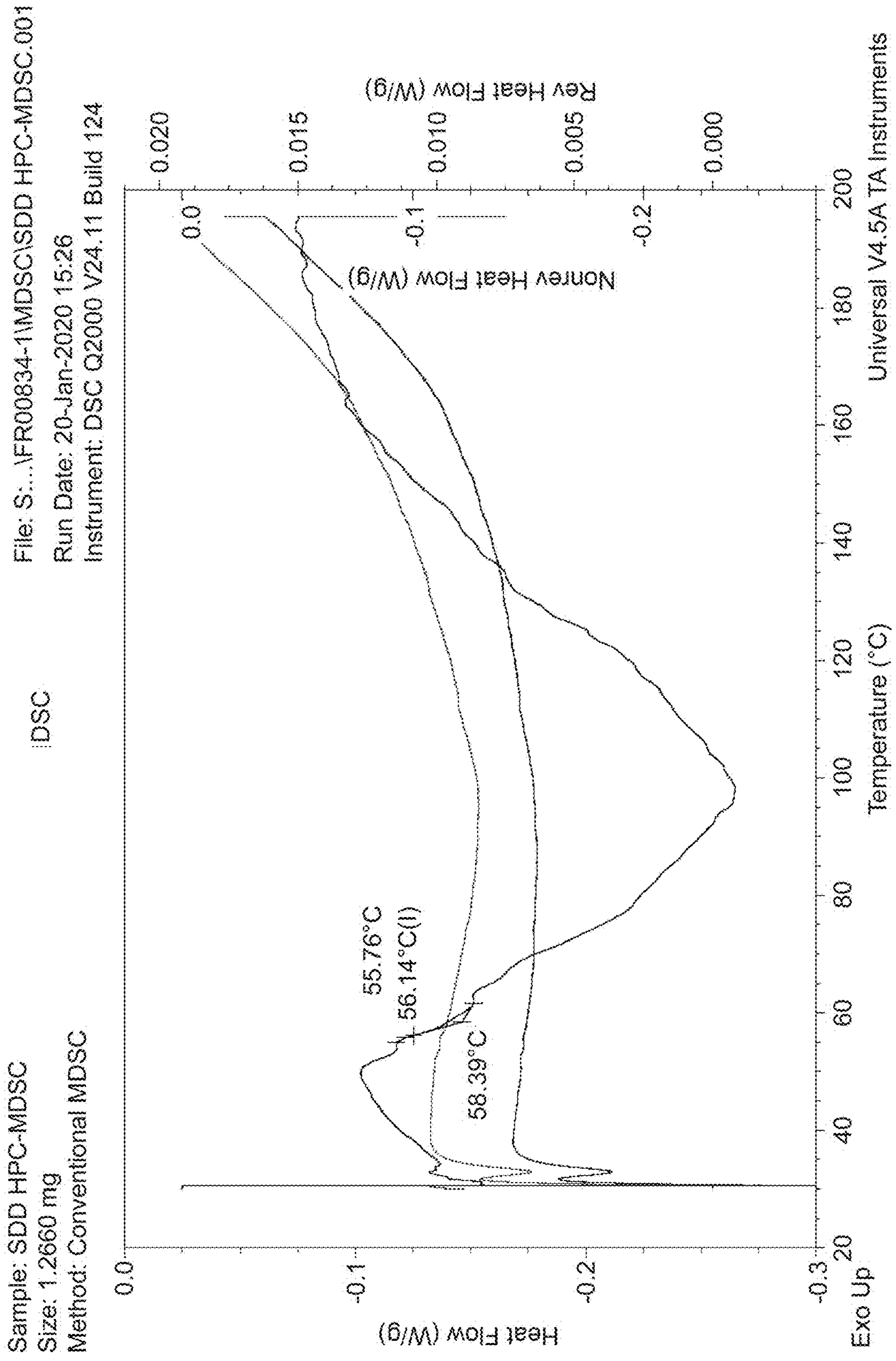
FIG. 5C shows a representative mDSC (modulated DSC) spectrum of SDD-13A.
Figure 5D:
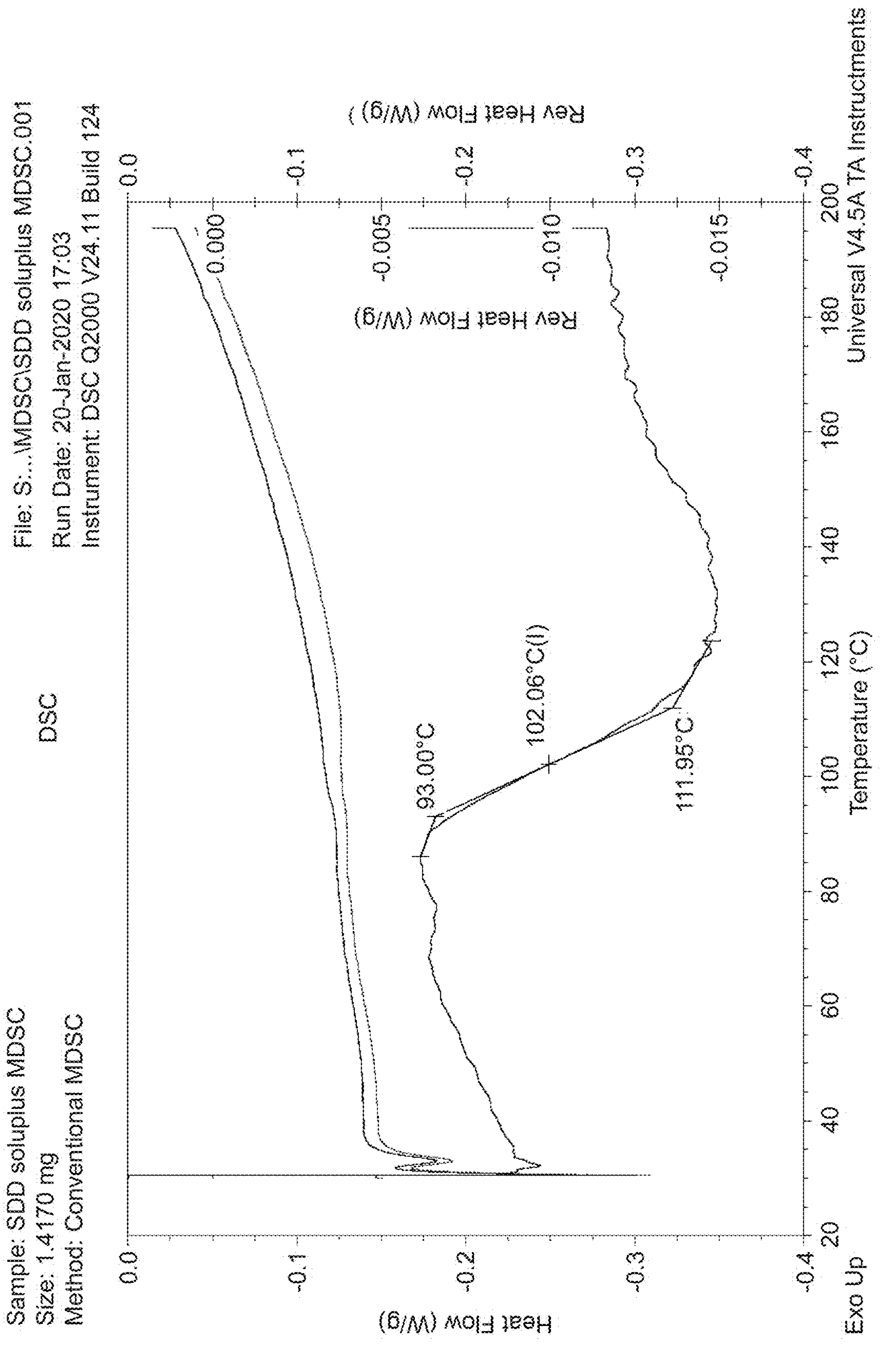
FIG. 5D shows a representative mDSC spectrum of SDD-10A.
Figure 5E:
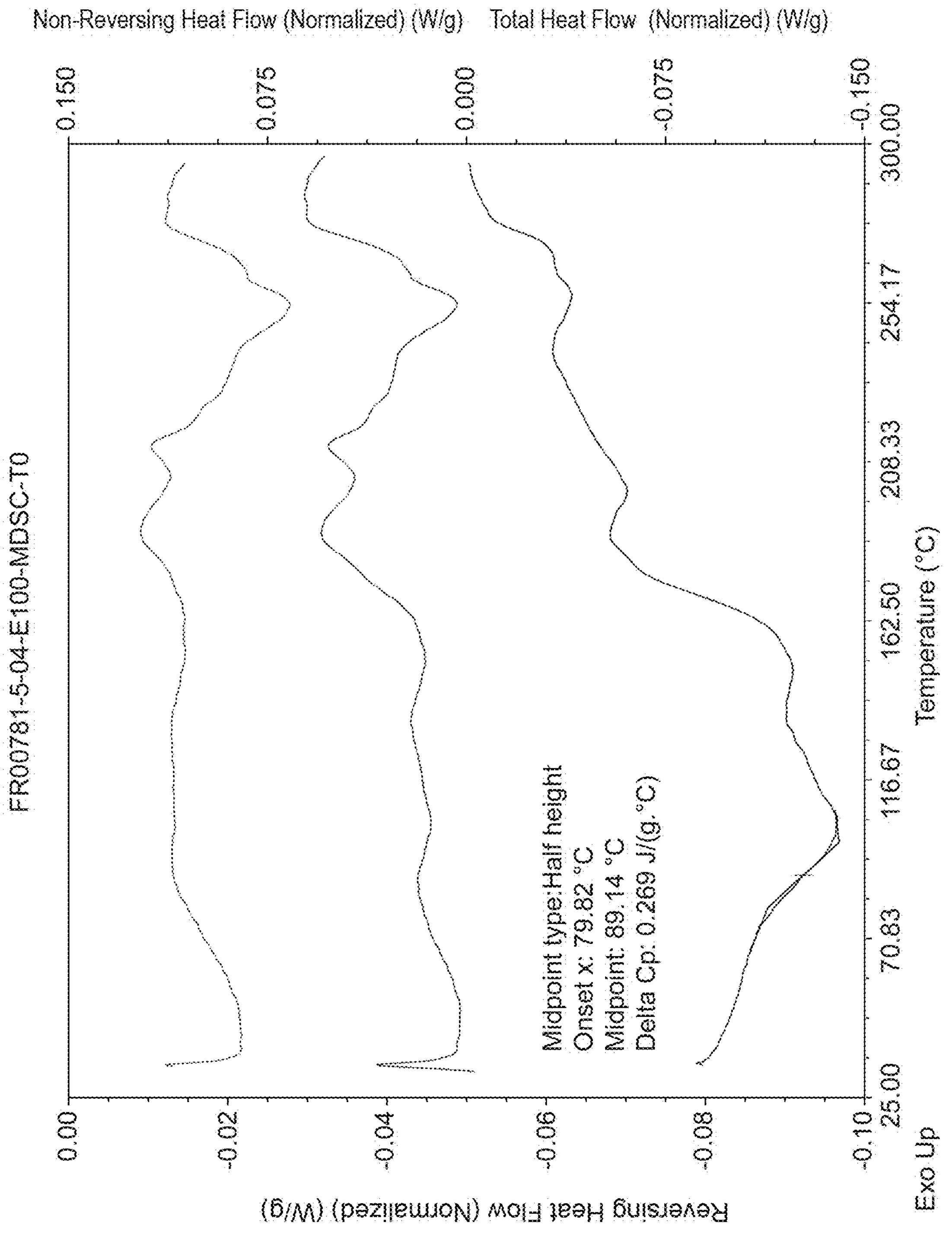
FIG. 5E shows a representative mDSC spectrum of SDD-19A.

The XRPD analysis of the solid dispersions are shown in FIGS. 4A and 4B.

To evaluate in-vitro release performance of SDDs, dissolution in FaSSIF (pH=6.5±0.05) was performed using the methods similar to those shown in Example 4. The dissolution results were shown in Table 11.

TABLE 11

| Dissolution test of API and SDD in FaSSIF (10 mL) | | | | | | |
|---|---|---|---|---|---|---|
| | API concentration in dissolution medium (μg/mL) | | | | | |
| Sample | 10 min | 20 min | 40 min | 60 min | 120 min | pH |
| SDD-9 | 292.6 | 278.6 | 288.8 | 281.8 | 289.2 | 6.43 |
| SDD-10 | 305.0 | 295.7 | 306.1 | 298.6 | 307.5 | 6.47 |
| SDD-11 | 321.4 | 312.2 | 320.5 | 312.7 | 323.1 | 6.51 |
| SDD-12 | 405.2 | 392.1 | 240.6 | 123.8 | 88.0 | 6.49 |
| SDD-13 | 395.7 | 391.0 | 323.5 | 129.9 | 84.7 | 6.42 |

TABLE 11-continued

| Dissolution test of API and SDD in FaSSIF (10 mL) | | | | | | |
|---|---|---|---|---|---|---|
| | API concentration in dissolution medium (μg/mL) | | | | | |
| Sample | 10 min | 20 min | 40 min | 60 min | 120 min | pH |
| SDD-14 | 378.0 | 390.2 | 372.1 | 156.5 | 87.0 | 6.44 |
| SDD-15 | 406.4 | 259.3 | 90.7 | 73.6 | 62.8 | 6.44 |
| SDD-16 | 398.3 | 126.6 | 81.7 | 70.7 | 65.1 | 6.44 |
| SDD-17 | 388.9 | 118.5 | 77.5 | 68.6 | 61.0 | 6.46 |
| SDD-18 | 535.0 | 530.3 | 516.9 | 512.1 | 507.6 | 6.78 |
| SDD-19 | 434.9 | 438.9 | 433.5 | 430.8 | 429.3 | 6.66 |
| SDD-20 | 387.7 | 393.1 | 386.7 | 385.7 | 383.8 | 6.6 |
| Compound 1 (Form B) | 10.8 | 12.5 | 14.3 | 14.2 | 14.9 | 6.41 |

1-week stability evaluation of SDD was also conducted using the same methods described in Example 4. The results are shown in Table 12.

TABLE 12

| Summary of 1-week stability test for SDD | | | | | |
|---|---|---|---|---|---|
| Sample No. | Initial purity (%) | Storage condition | Appearance | XRPD | Purity (%) |
| Compound 1 (Form B) | 98.75 | 2-8° C., closed | Yellow powder | Crystal | 98.81 |
| | | 25° C./60% RH, open | Yellow powder | Crystal | 98.86 |
| | | 40° C./75% RH, open | Yellow powder | Crystal | 98.79 |
| SDD-9 | 98.96 | 2-8° C., closed | Yellow powder | Amorphous | 98.87 |
| | | 25° C./60% RH, open | Yellow powder | Amorphous | 99.01 |
| | | 40° C./75% RH, open | Yellow solid, agglomeration | Amorphous | 98.77 |
| SDD-10 | 98.96 | 2-8° C., closed | Yellow powder | Amorphous | 99.01 |
| | | 25° C./60% RH, open | Yellow powder | Amorphous | 99.01 |
| | | 40° C./75% RH, open | Yellow solid, agglomeration | Amorphous | 98.77 |
| SDD-11 | 99.02 | 2-8° C., closed | Yellow powder | Amorphous | 99.01 |
| | | 25° C./60% RH, open | Yellow powder | Amorphous | 98.94 |
| | | 40° C./75% RH, open | Yellow powder | Amorphous | 98.86 |
| SDD-12 | 98.95 | 2-8° C., closed | Yellow powder | Amorphous | 98.95 |
| | | 25° C./60% RH, open | Yellow powder | Amorphous | 99.01 |
| | | 40° C./75% RH, open | Yellow solid, agglomeration | Amorphous | 98.82 |
| SDD-13 | 99.02 | 2-8° C., closed | Yellow powder | Amorphous | 99.02 |
| | | 25° C./60% RH, open | Yellow powder | Amorphous | 98.94 |
| | | 40° C./75% RH, open | Yellow powder | Amorphous | 98.76 |
| SDD-14 | 98.98 | 2-8° C., closed | Yellow powder | Amorphous | 98.97 |
| | | 25° C./60% RH, open | Yellow powder | Amorphous | 98.95 |
| | | 40° C./75% RH, open | Yellow powder | Amorphous | 98.84 |
| SDD-15 | 99.03 | 2-8° C., closed | Yellow powder | Amorphous | 98.99 |
| | | 25° C./60% RH, open | Yellow powder | Amorphous | 98.96 |
| | | 40° C./75% RH, open | Yellow powder | Amorphous | 98.82 |

TABLE 12-continued

| Summary of 1-week stability test for SDD | | | | | |
|---|---|---|---|---|---|
| Sample No. | Initial purity (%) | Storage condition | Appearance | XRPD | Purity (%) |
| SDD-16 | 98.94 | 2-8° C., closed | Yellow powder | Amorphous | 98.95 |
| | | 25° C./60% RH, open | Yellow powder | Amorphous | 98.97 |
| | | 40° C./75% RH, open | Yellow powder | Amorphous | 98.83 |
| SDD-17 | 98.91 | 2-8° C., closed | Yellow powder | Amorphous | 98.94 |
| | | 25° C./60% RH, open | Yellow powder | Amorphous | 98.95 |
| | | 40° C./75% RH, open | Yellow powder | Amorphous | 98.92 |
| SDD-18 | 98.73 | 2-8° C., closed | Yellow powder | Amorphous | 98.93 |
| | | 25° C./60% RH, open | Yellow powder | Amorphous | 99.01 |
| | | 40° C./75% RH, open | Yellow powder | Amorphous | 98.77 |
| SDD-19 | 99.02 | 2-8° C., closed | Yellow powder | Amorphous | 98.96 |
| | | 25° C./60% RH, open | Yellow powder | Amorphous | 98.98 |
| | | 40° C./75% RH, open | Yellow powder | Amorphous | 98.77 |
| SDD-20 | 98.98 | 2-8° C., closed | Yellow powder | Amorphous | 98.96 |
| | | 25° C./60% RH, open | Yellow powder | Amorphous | 98.97 |
| | | 40° C./75% RH, open | Yellow powder | Amorphous | 98.82 |

Example 6. Preparation of Amorphous Solid Dispersion of Compound 1 With 40% Drug Load In this example, Compound 1 and polymer (2:3, w/w) with Compound 1 concentration of 50 mg/mL were dissolved in organic solvents as spray drying solution for solid dispersion preparation. The solutions were spray dried using BUCHI B290. Detail process parameters for solid dispersion preparation were listed in Table 13. The collected powders (SDD-13A and SDD-10A) were dried under vacuum at 60° C. about 8 hours and the collected powders (SDD-0A and SDD-19A) were dried under vacuum at 40° C. about 8 hours, then all powders were stored at 2-8° C.

TABLE 13

| Spray drying parameters for solid dispersion preparation | | | | | |
|---|---|---|---|---|---|
| API concentration (mg/mL) | | 50 | | | |
| Solvent | | DCM:MeOH (1:1, v/v) | | | |
| Nozzle size (mm) | | 0.7 | | | |
| Settings | Inlet, ° C. | 88 | 88 | 88 | 88 |
| | Aspirator, % | 100 | 100 | 100 | 100 |
| | Pump, % | 40 | 40 | 40 | 40 |
| | Q-flow*, mm | 40 | 50 | 50 | 50 |
| Actual | Inlet, ° C. | 86-90 | 86-90 | 86-90 | 86-90 |
| | Outlet, ° C. | 52-57 | 50-58 | 52-57 | 52-57 |
| Spray Dried Dispersion No. | | SDD-0A | SDD-13A | SDD-10A | SDD-19A |

The SDD powders obtained were characterized by KF, XRFD, SEM, mDSC and HPLC. The XRPD and mDSC analysis were performed using the same methods described in Example 4. SEM analysis was conducted using Phenom ProX, Phenom World, with the following settings: Magnification: 400×, 500×, 1000×, 3000×; Detector: BSD Full; Voltage: 5 kV; and Current: Point. Moisture content of samples were determined by Coulometric KF Titrator. Briefly, place enough Honeywell coulomat AG in the titration vessel to immerge the electrode. When the drift value was ≤25 μg/min, quickly add accurately measured sample of appropriate weight to the vessel, mix, enter "weight (g)" and correlative sample information, and then titrate to the endpoint. The HPLC analysis were conducted using HPLC Method 2:

| | | | |
|---|---|---|---|
| Instrument | Agilent 1260 | | |
| Column | Waters Sunfire C18, 4.6 × 150 mm, 3.5 μm | | |
| Gradient | Time (min) | A %: 0.1% TFA in water (v/v) | B %: 0.1% TFA in ACN (v/v) |
| | 0 | 90 | 10 |
| | 4 | 70 | 30 |
| | 12 | 60 | 40 |
| | 24 | 57 | 43 |
| | 40 | 10 | 90 |
| | 45.1 | 90 | 10 |
| | 50 | 90 | 10 |
| Injection volume | 5 μL | | |
| Flow rate | 0.8 mL/min | | |
| Column Temp. | 10° C. | | |
| Wavelength | 220 nm | | |
| Diluent | ACN:water = 8:2 (v/v) or MeOH or ACN:water = 1:1 (v/v) | | |
| Concentration | 0.5 mg/mL | | |

The results were summarized in Table 14, and raw data were shown in FIGS. 5A-5E. Based on XRPD results, all spray dried products were amorphous solid dispersions.

TABLE 14

| Characterization of initial SDD | | | | | |
|---|---|---|---|---|---|
| Sample No. | XRPD | mDSC/Tg (° C.) | Drug load (%) | Purity (%) | KF (%) |
| SDD-0A | Amorphous | N/A | N/A | 98.85 | N/A |
| SDD-13A | Amorphous | 56.1 | 40.0 | N/A | 1.571 |
| SDD-10A | Amorphous | 102.1 | 39.9 | 98.88 | 1.602 |
| SDD-19A | Amorphous | 89.1 (accompanied with recrystallization) | 39.9 | 98.83 | 0.669 |

Note:
the purity of initial Compound 1 for preparing the SDD powders was 98.88%.

The SDD powders were also evaluated for dissolution in accordance with the methods shown in Example 4. The dissolution results were shown in Table 15.

TABLE 15

| Dissolution test of API and SDD in FaSSIF (10 mL) | | | | | | |
|---|---|---|---|---|---|---|
| | API concentration in dissolution medium (μg/mL) | | | | | |
| Sample No. | 10 min | 20 min | 40 min | 60 min | 120 min | pH |
| Compound 1 (Form B) | 8.1 | 8.4 | 9.0 | 9.1 | 9.7 | 6.48 |
| SDD-13A | 393.3 | 380.9 | 337.1 | 121.0 | 74.8 | 6.47 |
| SDD-10A | 297.6 | 293.5 | 293.0 | 291.0 | 289.0 | 6.46 |
| SDD-19A | 417.2 | 417.7 | 413.0 | 411.2 | 412.0 | 6.78 |

Example 7. Scale-up of Amorphous Solid Dispersion of Compound 1 With 40% Drug Load This examples shows an exemplary scale up of amorphous solid dispersion of Compound 1 with polymer Eudragit E100 (Evonik, lot no. B181201866). The ingredients used for this examples and relative amounts are shown in Table 16 below:

TABLE 16

| Ingredients for Scale-up Process | | |
|---|---|---|
| Ingredient | %(w/w)Level | Theoretical Amount Dispensed per sublot/g |
| Methanol | 33.51 | 7912.0 |
| Dichloromethane | 55.90 | 13200.0 |
| Compound 1 | 4.24 | 1000.0 |
| Eudragit E100 | 6.35 | 1500.0 |
| Total solid weight (g) | | 2500.0 |

The detailed process is as following: Weighed and prepared the mixed solvents using target amounts of methanol and dichloromethane. Then added target amounts of Compound 1 into mixed solvents slowly, sealed and stirred until dissolved. After which, the solution was filtered with 0.22 μm filter and the filter was rinsed using 200 g solvents. Target amounts of Eudragit E100 were then added into the filtered solution slowly, stirred until dissolved completely to obtain the final active solution. The active solution was filtered using 20 μm filter before spray drying. The spray drying was conducted using GEA PSD-1 spray dryer, using the following suggested parameters: nozzle size, 1 mm; nozzle type, Two-fluid nozzle; circulation gas flow, 100 kg/h; inlet temperature, 100.0(95.0-105.0)° C.; outlet temperature, 55.0(50.0-60.0) ° C.; atomization gas flow rate, 80(70-90) NL/min; B1R62 atomization pressure, 3.0±0.5 bar; B1P62 gun atomization pressure, 1.2±0.2 bar, condenser temperature, −5 (−10-0)° C. During spray drying, key parameters were monitored. The inlet temperature and outlet temperature were stable. The spray rate was maintained at 80-100 g/min. Once spray drying was finished, the obtained wet cake was spread evenly on the tray of vacuum dryer. The wet cake was dried for 6 h at a drying temperature of 50° C. and vacuum degree was set at less than −80 kpa. The product was collected after the results of residue solvent were qualified. All collected products were placed in a bin and blended for 20 min at 20 rpm, and obtained the final solid dispersion of Compound 1.

The obtained solid dispersion was analyzed using SEM, HPLC, GC, XRPD. A representative analytical result and specification is shown below in Table 17.

TABLE 17

| Representative Specification of Solid Dispersion and Analytical Results | | | | | | |
|---|---|---|---|---|---|---|
| | Specification | | | Result | | |
| Identification by UV | The difference of the maximum absorption wavelength for main peak between sample solution and standard solution should be within ±2 nm | | | The difference of the maximum absorption wavelength for main peak between sample solution and standard solution is 0 nm | | |
| Identification by HPLC | Retention time of sample is within ±5% of standard | | | Retention time of sample is 0% of standard (i.e., same) | | |
| Assay by HPLC | 36.0%-44.0% | | | 40.2% | | |
| Related substances by HPLC (w/w %) | Specified impurities | RRT 1.03 | ≤0.29% | Specified impurities | RRT 1.03 | <0.05% |
| | | RRT 1.15 | ≤0.34% | | RRT 1.15 | <0.05% |
| | | RRT 1.66 | ≤0.21% | | RRT 1.66 | <0.05% |
| | Unspecified impurity | | ≤0.15% | Unspecified impurity | RRT 0.53 | 0.07% |
| | | | | | RRT 0.84 | <0.05% |
| | Total impurities | | ≤2.0% | Total impurities | | 0.07% |
| Water Content (KF, w/w %) | Report results | | | 0.9% | | |
| Residual solvents(GC): Methanol Dichloromethane | Methanol | | ≤3000 ppm | Methanol | | N.D. |
| | Dichloromethane | | ≤600 ppm | Dichloromethane | | <LOQ (LOQ = 101 ppm) |
| Solid state from by XRPD | Amorphous | | | Amorphous | | |
| Particle Size Distribution | Report $D_{10}$, $D_{50}$, $D_{90}$ | | | $D_{10}$: 1.568 μm<br>$D_{50}$: 6.316 μm<br>$D_{90}$: 13.844 μm | | |

Example 8. Preparing Tablets With Amorphous Solid Dispersion of Compound 1

This example shows exemplary procedures for preparing tablets using the amorphous solid dispersion prepared in Example 7. The manufacturing process included roller compaction and tablet compression, optionally coating process after tablet compression. The ingredients for the tablet formulations are shown in the Table 18 below:

TABLE 18

| Composition of a Table Formulation | |
|---|---|
| Ingredient | % by weight |
| Intra-granular | |
| Solid Dispersion of Compound 1 (40% drug loading) | 62.50 |
| Microcrystalline Cellulose PH-101 | 19.50 |
| Mannitol 100SD | 10.00 |
| Croscarmellose Sodium | 2.00 |
| Colloidal Silica Dioxide Aerosil 200 Pharma | 1.50 |
| Sodium stearyl fumarate | 0.75 |
| Intra-granular total | 96.25 |
| Extra-granular | |
| Croscarmellose Sodium | 3.00 |
| Sodium stearyl fumarate | 0.75 |
| Core-tablet Total | 100.00 |
| Opadry ®Complete Film Coating System 03K620011-CN Yellow | 3.00 |

The detailed process is shown below: Dispensing the ingredients in the order of excipients and the solid dispersion. Pre-blending: Screened the microcrystalline cellulose PH-101 using Comil and put it into a bin. Then put the solid dispersion of Compound 1 (40% drug loading), prepared from Example 7, into the bin. Blend the mannitol 100SD and intra-granular target amount of croscarmellose sodium in the colloidal silica dioxide bag and screened the blend. Used a small amount of screened blend to rinse the solid dispersion bag repeatedly and put it into the bin, then blended. Screened the blend once again and put it into the bin. Weighed the intra-granular sodium stearyl fumarate screened through 40 mesh screen and blended with the above blend, and the final pre-blending powder was obtained.

Roller compaction: Roller compacted the pre-blending powder which was fed appropriately. In roller compaction process, kept the roll gap at 2.0 mm and final granules were obtained.

Blending: Charged the obtained roller compacted granules into the bin. Weighed and put the target amount of extra-granular croscarmellose sodium and sodium stearyl fumarate, which were screened through 40 mesh screen, into the bin and blended following the set parameters. Finally, the granules after blending were obtained.

Tablet compression: Divided the common granules into two parts, one part was used for the compression of 50 mg tablets and others was used for 200 mg tablets.

Tablet coating: Only 200 mg tablets were coated by using the gastro-soluble opaday coating system.

The tablets were bottled in white HDPE bottle. The bottles were screwed tightly and induction sealed using child safe caps.

The tablets prepared were found to meet specifications.

Stability data show that tablets prepared according to this example are stable up to 6 months at accelerated storage condition (40° C./75% RH) and long term condition (25° C./60% RH). No significant changes were observed in terms of appearance, solid state of Compound 1, drug release profile, related substance and assay for Compound 1 after storage under either normal or accelerated stability testing conditions. For example, Compound 1 remains in an amorphous state throughout the storage period up to 6 months. The release profile of the tablets were also not changed during the testing period.

Example 9. Six-Month Stability Data of Amorphous Solid Dispersion

This example studies long term stability of amorphous solid dispersion prepared according to the procedure shown in Example 7.

The stability test was conducted similar to the procedure described in Example 4, except with longer duration. Briefly, the solid dispersion prepared according to Example 7 was sealed in aluminum foil bag and placed under long term (25° C.±2° C./60% RH±5% RH) and accelerated stability testing conditions (40° C.±2° C./75% RH±5% RH), and samples were analyzed at different time points, including time 0 (initial), 1 month, 2 months, 3 months, and 6 months. The samples were analyzed for their appearances, solid states (using XRPD), dissolutions, related substance of Compound 1, and assay for Compound 1. The dissolution tests were conducted similar to those described in Example 4. The methods for analyzing related substance and assay for Compound 1 are described below.

The following reversed phase HPLC method was used in this example for assay determination of Compound 1 for amorphous solid dispersion.

| | |
|---|---|
| Instrument | HPLC system with UV detector or equivalent |
| Column | Waters Sunfire C18, 4.6 × 150 mm, 3.5 μm |
| Wavelength | 360 nm |
| Column oven Temperature | 30° C. |
| Flow Rate | 0.8 mL/min |
| Injection Volume | 5 μL |
| Mobile Phase A | 0.1% TFA in purified water |
| Mobile Phase B | 0.1% TFA in ACN |
| Gradient program | MA:MB = 40:60 (V/V), Isocratic |
| Run Time | 6 min |
| Diluent | Acetonitrile:Water = 80:20 (v/v) |
| Needle Wash | Acetonitrile:Water = 50:50 (v/v) |

The following method was used for related substance of Compound 1 determination in this example for the solid dispersions, a reversed phase HPLC method using UV detector at 220 nm:

| | | | |
|---|---|---|---|
| Instrument | HPLC system with UV detector or equivalent | | |
| Column | Waters Sunfire C18, 4.6 × 250 mm, 5 μm | | |
| Wavelength | 220 nm | | |
| Column oven Temperature | 10° C. | | |
| Flow Rate | 1.0 mL/min | | |
| Injection Volume | 7 μL | | |
| A Mobile Phase A | 0.1% TFA in purified water | | |
| B Mobile Phase B | 0.1% TFA in ACN | | |
| Gradient program | Time (min) | MPA | MPB |
| | 0.00 | 90 | 10 |
| | 5.33 | 70 | 30 |
| | 16.00 | 60 | 40 |
| | 32.00 | 57 | 43 |

-continued

| | | | |
|---|---|---|---|
| | 36.00 | 55 | 45 |
| | 45.00 | 10 | 90 |
| | 50.00 | 10 | 90 |
| | 50.10 | 90 | 10 |
| | 55.00 | 90 | 10 |
| Run Time | 55 min | | |
| Diluent | Acetonitrile:Water = 80:20 (v/v) | | |
| Needle Wash | Acetonitrile:Water = 50:50 (v/v) | | |

The stability results under accelerated storage conditions were shown in Tables 19 (including tables 19-1 to 19-5) below:

TABLE 19

Accelerated stability dada for 6 months under 40° C. ± 2° C./75% RH ± 5% RH

| Tests | Acceptance Criteria | Initial | 1M | 2M | 3M | 6M |
|---|---|---|---|---|---|---|
| Appearance | Yellow powder. | Yellow powder. | Yellow powder. | Yellow powder. | Yellow powder. | Yellow powder. |
| Crystal form | Amorphous | Amorphous | Amorphous | Amorphous | Amorphous | Amorphous |
| Dissolution | Report results | See Table 19-1 | See Table 19-2 | See Table 19-3 | See Table 19-4 | See Table 19-5 |
| Related Substance | Specified impurities<br>RRT 1.03 ≤ 0.29%<br>RRT 1.15 ≤ 0.34%<br>RRT 1.66 ≤ 0.21% | RRT 1.03: 0.06%<br>RRT 1.24: ND<br>RRT 1.67: <0.05% | RRT 1.03: <0.05%<br>RRT 1.23: <0.05%<br>RRT 1.67: <0.05% | RRT 1.03: <0.05%<br>RRT 1.24: ND<br>RRT 1.66: <0.05% | RRT 1.03: <0.05%<br>RRT 1.21: ND<br>RRT 1.67: <0.05% | RRT 1.03: <0.05%<br>RRT 1.23: ND<br>RRT 1.66: ND |
| | Unspecified impurity ≤0.15% | RRT 0.55: 0.07%<br>RRT 1.56: 0.09% | RRT 0.56: 0.06%<br>RRT 1.56: 0.08% | RRT 0.55: 0.07%<br>RRT 1.55: 0.08% | RRT 0.55: 0.08%<br>RRT 1.56: 0.08% | RRT 0.52: 0.05%<br>RRT 0.55: 0.09%<br>RRT 0.57: <0.05%<br>RRT 1.56: 0.11% |
| | Total impurities ≤2.0% | 0.22% | 0.14% | 0.15% | 0.16% | 0.25% |
| Assay | 36.0%-44.0% | 40.0% | 40.1% | 39.7% | 39.9% | 39.8% |

TABLE 19-1

| T/min | 10 | 20 | 40 | 60 | 120 |
|---|---|---|---|---|---|
| 1 | 421.2 | 435.9 | 406.9 | 403.0 | 403.9 |
| 2 | 411.4 | 432.8 | 407.3 | 401.4 | 396.0 |
| 3 | 399.3 | 426.0 | 393.8 | 391.7 | 396.1 |
| Mean(μg/mL) | 410.6 | 431.6 | 402.7 | 398.7 | 398.7 |
| % RSD | 2.7 | 1.2 | 2.0 | 1.6 | 1.2 |

TABLE 19-2

| T/min | 10 | 20 | 40 | 60 | 120 |
|---|---|---|---|---|---|
| 1 | 421.5 | 403.7 | 405.5 | 393.8 | 392.2 |
| 2 | 392.0 | 394.8 | 393.2 | 393.1 | 400.8 |
| 3 | 408.2 | 405.0 | 393.7 | 401.0 | 404.3 |
| Mean(μg/mL) | 407.2 | 401.2 | 397.5 | 396.0 | 399.1 |
| % RSD | 3.7 | 1.4 | 1.8 | 1.2 | 1.6 |

TABLE 19-3

| T/min | 10 | 20 | 40 | 60 | 120 |
|---|---|---|---|---|---|
| 1 | 375.3 | 393.7 | 400.9 | 397.2 | 406.6 |
| 2 | 360.8 | 387.8 | 398.6 | 393.5 | 413.1 |
| 3 | 303.5 | 371.5 | 381.1 | 383.5 | 409.3 |
| Mean(μg/mL) | 346.5 | 384.3 | 393.5 | 391.4 | 409.7 |
| % RSD | 11.0% | 3.0% | 2.8% | 1.9% | 0.8% |

TABLE 19-5

| T/min | 10 | 20 | 40 | 60 | 120 |
|---|---|---|---|---|---|
| 1 | 384.5 | 400.3 | 396.9 | 407.1 | 415.5 |
| 2 | 348.0 | 388.4 | 401.9 | 402.5 | 436.4 |
| 3 | 414.0 | 390.0 | 402.9 | 391.2 | 445.2 |
| Mean(μg/mL) | 382.2 | 392.9 | 400.6 | 400.3 | 432.4 |
| % RSD | 8.7% | 1.7% | 0.9% | 2.1% | 3.6% |

TABLE 19-4

| T/min | 10 | 20 | 40 | 60 | 120 |
|---|---|---|---|---|---|
| 1 | 388.9 | 412.6 | 422.0 | 408.0 | 407.8 |
| 2 | 340.5 | 377.9 | 406.6 | 401.8 | 388.9 |
| 3 | 338.9 | 375.7 | 375.9 | 372.6 | 393.0 |
| Mean(μg/mL) | 356.1 | 388.7 | 401.5 | 394.1 | 396.6 |
| % RSD | 8.0% | 5.4% | 5.9% | 4.8% | 2.6% |

The stability results under normal storage conditions were shown in Tables 20 (including tables 20-1 to 20-3) below:

TABLE 20

Long term stability data for 6 months under 25° C. ± 2° C./60% RH ± 5% RH

| Tests | Acceptance Criteria | Initial | 3 M | 6 M |
|---|---|---|---|---|
| Appearance | Yellow powder. | Yellow powder. | Yellow powder. | Yellow powder. |
| Crystal form | Amorphous | Amorphous | Amorphous | Amorphous |
| Dissolution | Report results | See Table 20-1 | See Table 20-2 | See Table 20-3 |
| Related | Specified impurities* | RRT 1.03: 0.06% | RRT 1.03: <0.05% | RRT 1.03: <0.05% |

TABLE 20-continued

| Long term stability data for 6 months under 25° C. ± 2° C./60% RH ± 5% RH | | | | |
|---|---|---|---|---|
| Tests | Acceptance Criteria | Initial | 3 M | 6 M |
| Substance | RRT 1.03 ≤0.29%<br>RRT 1.15 ≤0.34%<br>RRT 1.66 ≤0.21% | RRT 1.24: ND<br>RRT 1.67: <0.05% | RRT 1.21: ND<br>RRT 1.67: <0.05% | RRT 1.23: ND<br>RRT 1.66: ND |
| | Unspecified impurity ≤0.15% | RRT 0.55: 0.07%<br>RRT 1.56: 0.09% | RRT 0.55: 0.10%<br>RRT 1.56: 0.09% | RRT 0.55: 0.06%<br>RRT 1.56: 0.11% |
| | Total impurities ≤2.0% | 0.22% | 0.19% | 0.17% |
| Assay | 36.0%-44.0% | 40.0% | 40.0% | 40.2% |

TABLE 20-1

| T/min | 10 | 20 | 40 | 60 | 120 |
|---|---|---|---|---|---|
| 1 | 421.2 | 435.9 | 406.9 | 403.0 | 403.9 |
| 2 | 411.4 | 432.8 | 407.3 | 401.4 | 396.0 |
| 3 | 399.3 | 426.0 | 393.8 | 391.7 | 396.1 |
| Mean(μg/mL) | 410.6 | 431.6 | 402.7 | 398.7 | 398.7 |
| % RSD | 2.7 | 1.2 | 2.0 | 1.6 | 1.2 |

TABLE 20-2

| T/min | 10 | 20 | 40 | 60 | 120 |
|---|---|---|---|---|---|
| 1 | 321.9 | 392.1 | 404.0 | 402.9 | 410.2 |
| 2 | 290.8 | 360.3 | 392.6 | 418.1 | 401.4 |
| 3 | 359.5 | 362.4 | 375.5 | 404.4 | 399.7 |
| Mean(μg/mL) | 324.1 | 371.6 | 390.7 | 408.5 | 403.8 |
| % RSD | 10.7% | 4.8% | 3.7% | 2.1% | 1.4% |

TABLE 20-3

| T/min | 10 | 20 | 40 | 60 | 120 |
|---|---|---|---|---|---|
| 1 | 399.5 | 401.6 | 408.0 | 415.2 | 405.1 |
| 2 | 371.2 | 395.9 | 408.3 | 410.6 | 410.1 |
| 3 | 362.2 | 380.2 | 399.8 | 413.8 | 417.0 |
| Mean(μg/mL) | 377.6 | 392.6 | 405.4 | 413.2 | 410.7 |
| % RSD | 5.2% | 2.9% | 1.2% | 0.6% | 1.5% |

Based on the results shown above, it can be seen that the amorphous solid dispersion prepared according to Example 7 was storage stable for at least 6 months. No significant changes were observed in terms of appearance, solid state, dissolution profile, related substance and assay after storage under either normal or accelerated stability testing conditions.

Example 10. Preparing Capsules With Amorphous Solid Dispersion of Compound 1

This example shows exemplary procedures for preparing capsules using the amorphous solid dispersion. The solid dispersion of Compound 1 (40% drug loading and Eudragit E100) was prepared according to procedures similar to Example 7.

Direct mixing: Silicified microcrystalline cellulose SMCC50 with good flowability was selected as diluent. Croscarmellose sodium was used as disintegrant and sodium stearyl fumarate was used as lubricant. The excipients amounts used in the formulation are generally within standard quantities of usage. Gelatin capsule shells were used in formulation and process development. The theoretical batch size of this batch was 15.00 g. The ingredients used for the capsules from direct mixing are shown in the Table 21 below:

TABLE 21

| Composition of a Capsule Formulation for Direct Mixing | |
|---|---|
| Ingredient | % weight |
| Solid Dispersion of Compound 1 (40% drug loading) | 62.50 |
| Silicified Microcrystalline Cellulose Prosolv SMCC50 | 36.00 |
| Croscarmellose Sodium | 1.00 |
| Sodium Stearyl Fumarate | 0.50 |
| Total | 100.00 |

Capsules from roller compaction granules. Capsules were also prepared by using the roller compaction granules, which was obtained from similar procedures described in Example 8. The ingredients used for capsules using this method are shown in the Tables 22A and 22B below:

TABLE 22A

| Composition of a Capsule Formulation for Roller Compaction | |
|---|---|
| Ingredient | % weight |
| Intra-granular | |
| Solid Dispersion of Compound 1 (40% drug loading) | 62.50 |
| Microcrystalline Cellulose PH-101 | 19.50 |
| Mannitol 100SD | 10.00 |
| Croscarmellose Sodium | 2.00 |
| Colloidal Silica Dioxide Aerosil 200 Pharma | 1.50 |
| Sodium Stearyl Fumarate | 0.75 |
| Intra-granular total | 96.25 |
| Extra-granular | |
| Croscarmellose Sodium | 3.00 |
| Sodium Stearyl Fumarate | 0.75 |
| Total | 100.00 |

TABLE 22B

| Composition of additional Capsule Formulations for Roller Compaction | | | |
|---|---|---|---|
| Ingredient | % weight | % weight | % weight |
| Intra-granular | | | |
| Solid Dispersion of Compound 1 (40% drug loading) | 80.00 | 75 | 70.00 |
| Silicified Microcrystalline Cellulose Prosolv SMCC50 | 15.00 | 20 | 25.00 |

TABLE 22B-continued

| Composition of additional Capsule Formulations for Roller Compaction | | | |
|---|---|---|---|
| Ingredient | % weight | % weight | % weight |
| Croscarmellose Sodium | 2.00 | 2.00 | 2.00 |
| Sodium Stearyl Fumarate | 0.75 | 0.75 | 0.75 |
| Intra-granular total | 97.75 | 97.75 | 97.75 |
| Extra-granular | | | |
| Croscarmellose Sodium | 2.00 | 2.00 | 2.00 |
| Sodium Stearyl Fumarate | 0.25 | 0.25 | 0.25 |
| Total | 100.00 | 100.00 | 100.00 |

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A solid dispersion comprising Compound 1 in an amorphous form and a matrix polymer, wherein Compound 1 has the following formula:

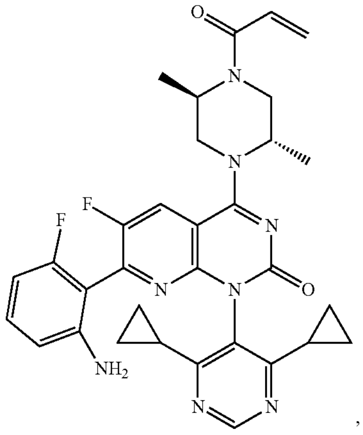 [SMILES: C=CC(=O)N1C[C@H](C)N(c2nc(=O)n(-c3c(C4CC4)ncnc3C3CC3)c3nc(-c4c(N)cccc4F)c(F)cc23)C[C@H]1C]

, wherein the matrix polymer is selected from cellulose esters and cellulose ethers, polyalkylene oxides, polyacrylates and polymethacrylates, homopolymers and copolymers of N-vinyl lactams, polyacrylamides, vinyl acetate polymers, graft copolymers of polyethylene glycol, polyvinyl caprolactam and polyvinyl acetate, polyvinyl acetate phthalate, oligo- and polysaccharides, and mixtures of two or more thereof.

2. The solid dispersion of claim 1, which is essentially free of Compound 1 in a crystalline form.

3. The solid dispersion of claim 1, which does not include Compound 1 in a crystalline form in an amount detectable by XRPD.

4. The solid dispersion of claim 1, wherein the matrix polymer comprises a polyacrylate or polymethacrylate.

5. The solid dispersion of claim 1, wherein the matrix polymer is poly((2-dimethylaminoethyl) methacrylate, butyl methacrylate, methyl methacrylate) (2:1:1).

6. The solid dispersion of claim 1, wherein the matrix polymer comprises one or more polymers selected from vinyl pyrrolidone polymers and vinyl caprolactam polymers.

7. The solid dispersion of claim 1, wherein the matrix polymer comprises one or more polymers selected from povidone, copovidone, and a graft copolymer of polyethylene glycol, polyvinyl acetate and polyvinylcaprolactam.

8. The solid dispersion of claim 1, wherein the matrix polymer comprises a graft copolymer of polyethylene glycol 6000, polyvinyl acetate and polyvinylcaprolactam, with a weight average molecular weight (Mw) of about 90,000 g/mol to about 140,000 g/mol.

9. The solid dispersion of claim 1, wherein the matrix polymer comprises a graft copolymer of polyethylene glycol 6000, polyvinyl acetate and polyvinylcaprolactam, with a weight ratio of about 13:30:57, wherein the graft copolymer has a weight average molecular weight (Mw) of about 118,000 g/mol.

10. The solid dispersion of claim 1, wherein the matrix polymer comprises one or more cellulose selected from hydroxypropylmethyl cellulose, hydroxypropylmethyl cellulose acetate succinate, hydroxypropyl methylcellulose phthalate (HPMCP), and hydroxypropyl cellulose.

11. The solid dispersion of claim 1, wherein the weight ratio of Compound 1 to the matrix polymer ranges from about 1:50 to 10:1.

12. The solid dispersion of claim 1, wherein Compound 1 is present in the solid dispersion in an amount ranging from about 10-80% by weight.

13. The solid dispersion of claim 1, which is a solid dispersion comprising Compound 1 in an amorphous form dispersed in a copolymer, wherein the copolymer is poly ((2-dimethylaminoethyl) methacrylate, butyl methacrylate, methyl methacrylate) (2:1:1), wherein the solid dispersion comprises about 30-50% by weight of Compound 1 and about 50-70% by weight of the copolymer.

14. The solid dispersion of claim 1, which is a solid dispersion comprising Compound 1 in an amorphous form dispersed in a graft copolymer of polyethylene glycol, polyvinyl acetate and polyvinylcaprolactam, wherein the solid dispersion comprises about 30-50% by weight of Compound 1 and about 50-70% by weight of the graft copolymer.

15. The solid dispersion of claim 1, which is a solid dispersion comprising Compound 1 in an amorphous form dispersed in hydroxypropylmethyl cellulose (HPMC), wherein the solid dispersion comprises about 30-50% by weight of Compound 1 and about 50-70% by weight of HPMC.

16. The solid dispersion of claim 1, which is a solid dispersion comprising Compound 1 in an amorphous form dispersed in hydroxypropyl cellulose, wherein the solid dispersion comprises about 30-50% by weight of Compound 1 and about 50-70% by weight of hydroxypropyl cellulose.

17. A pharmaceutical composition comprising the solid dispersion of claim 1.

18. A method of preparing a pharmaceutical composition comprising mixing the solid dispersion according to claim 1 with a pharmaceutical excipient.

19. A pharmaceutical composition comprising the solid dispersion of claim 13 and a pharmaceutically acceptable excipient.

20. A pharmaceutical composition comprising the solid dispersion of claim 14 and a pharmaceutically acceptable excipient.

21. A pharmaceutical composition comprising the solid dispersion of claim 15 and a pharmaceutically acceptable excipient.

22. A pharmaceutical composition comprising the solid dispersion of claim 16 and a pharmaceutically acceptable excipient.

23. A process for making a solid dispersion comprising:

(a) mixing Compound 1, a polymer, and a solvent to form a solution, wherein the polymer comprises an acrylate based polymer, an N-vinyl lactam polymer, or a cellulose; and (b) spray-drying the solution of step (a), thereby obtaining the solid dispersion, wherein Compound 1 has the following formula:

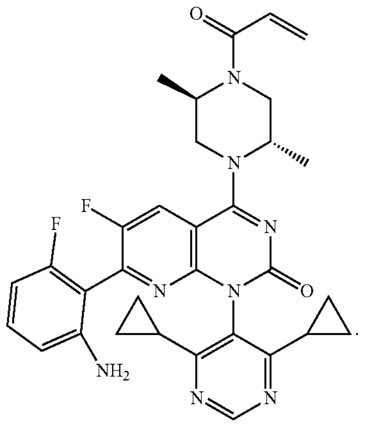 [SMILES: C=CC(=O)N1C[C@H](C)N(c2nc(=O)n(-c3c(C4CC4)ncnc3C3CC3)c3nc(-c4c(N)cccc4F)c(F)cc23)C[C@H]1C]

24. A method of treating cancer comprising a KRAS G12C mutation in a subject, the method comprising administering to the subject a therapeutically effective amount of the solid dispersion of claim 1, wherein the cancer is pancreatic cancer, endometrial cancer, colorectal cancer, or lung cancer.

25. The method of claim 24, wherein the cancer is non-small cell lung cancer.

* * * * *